United States Patent
Dunn-Coleman et al.

(10) Patent No.: US 7,691,617 B2
(45) Date of Patent: *Apr. 6, 2010

(54) ACID-STABLE ALPHA AMYLASES HAVING GRANULAR STARCH HYDROLYZING ACTIVITY AND ENZYME COMPOSITIONS

(75) Inventors: Nigel Dunn-Coleman, Palo Alto, CA (US); Susan M. Fiske, Palo Alto, CA (US); Suzanne E. Lantz, Palo Alto, CA (US); Paulien Neefe-Kruithof, Leiden (NL); Michael J. Pepsin, Palo Alto, CA (US); Jayarama K. Shetty, Palo Alto, CA (US)

(73) Assignee: Danisco US Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/022,365

(22) Filed: Jan. 30, 2008

(65) Prior Publication Data
US 2008/0153136 A1    Jun. 26, 2008

Related U.S. Application Data

(63) Continuation of application No. 11/136,244, filed on May 24, 2005, now Pat. No. 7,354,752.

(60) Provisional application No. 60/575,175, filed on May 27, 2004, provisional application No. 60/605,437, filed on Aug. 30, 2004, provisional application No. 60/647,925, filed on Jan. 28, 2005.

(30) Foreign Application Priority Data

Nov. 30, 2004    (WO) ............... PCT/US2004/040040
Dec. 9, 2004     (WO) ............... PCT/US2004/041276

(51) Int. Cl.
*C12N 9/30*     (2006.01)
*C12N 9/24*     (2006.01)
*C12Q 1/40*     (2006.01)
*C12P 21/06*    (2006.01)
*C12P 19/20*    (2006.01)
*C12N 1/00*     (2006.01)
*C07H 21/04*    (2006.01)

(52) U.S. Cl. .................. 435/203; 435/200; 435/22; 435/69.1; 435/96; 435/99; 435/175; 435/254.3; 435/254.6; 435/254.11; 435/484; 536/23.2

(58) Field of Classification Search .............. None
See application file for complete search history.

(56) References Cited

U.S. PATENT DOCUMENTS

| | | | |
|---|---|---|---|
| 3,249,514 A | 5/1966 | Bode | |
| 4,092,434 A | 5/1978 | Yoshizumi et al. | |
| 4,316,956 A | 2/1982 | Lützen | 435/96 |
| 4,460,687 A | 7/1984 | Ehnström | 435/161 |
| 4,514,496 A | 4/1985 | Yoshizumi et al. | |
| RE32,153 E | 5/1986 | Tamura et al. | |
| 4,587,215 A | 5/1986 | Hirsh | |
| 4,618,579 A | 10/1986 | Dwiggins et al. | |
| 4,727,026 A | 2/1988 | Sawada et al. | 435/96 |
| 4,863,864 A | 9/1989 | Ashikari et al. | |
| 5,246,853 A | 9/1993 | Clarkson et al. | |
| 5,475,101 A | 12/1995 | Ward et al. | |
| 5,650,322 A | 7/1997 | Clarkson et al. | |
| 5,874,276 A | 2/1999 | Fowler et al. | |
| 6,022,725 A | 2/2000 | Fowler et al. | |
| 6,268,328 B1 | 7/2001 | Mitchinson et al. | |
| 6,361,989 B1 | 3/2002 | Svendsen et al. | |
| 7,205,138 B2 | 4/2007 | Dunn-Coleman et al. | |

FOREIGN PATENT DOCUMENTS

| | | |
|---|---|---|
| EP | 0 171 218 B1 | 10/1993 |
| EP | 0 625 577 A1 | 11/1994 |
| EP | 0 244 234 B2 | 11/2001 |
| EP | 0 215 594 B2 | 10/2003 |
| WO | WO 84/02921 | 8/1984 |
| WO | WO 92/00381 | 1/1992 |
| WO | WO 92/06209 | 4/1992 |
| WO | WO 99/28488 | 7/1999 |
| WO | WO 99/60136 | 11/1999 |
| WO | WO 00/04136 | 1/2000 |
| WO | WO 02/38787 A2 | 5/2002 |
| WO | WO 02/074895 | 9/2002 |
| WO | WO 03/066826 A2 | 8/2003 |
| WO | WO 03/068976 A2 | 8/2003 |
| WO | WO 2004/113551 A1 | 12/2004 |

OTHER PUBLICATIONS

Guo et al., Protein tolerance to random amino acid change. PNAS., 2004, vol. 101 (25): 9205-9210.*

Seffernick et al., Melamine deaminase and Atrazine chlorohydrolase: 98 percent identical but functionally different. J. Bacteriol.,2001, vol. 183 (8): 2405-2410.*

(Continued)

*Primary Examiner*—Ganapathirama Raghu

(57) ABSTRACT

The present invention relates to an acid-stable alpha amylase (asAA) derived from a strain of *Aspergillus kawachi*, which has granular starch hydrolyzing (GSH) activity, the heterologous expression of the asAA having GSH activity in filamentous fungal host cells and enzyme compositions including the same which optionally include glucoamylase.

17 Claims, 14 Drawing Sheets

OTHER PUBLICATIONS

Witkowski et al., Conversion of b-ketoacyl synthase to a malonyl decarboxylase by replacemnt of the active-site cysteine with glutamine. Biochemistry, 1999, vol. 38: 11643-11650.*

Allison, Daniel S. et al., << Transformation of the thermophilic fungus *Humicola grisea* var. *thermoidea* and overproduction of *Humicola* glucoamylase, >> Current Genetics, vol, 21, pp. 225-229, 1992.

Altshul, Stephen F. et al., << Gapped BLAST and PSI-BLAST: a new generation of protein database search programs, >> Nucleic Acids Research, vol. 25, No. 17, pp. 3389-3402, 1997.

Ashikari, Toshihiko et al., << *Rhizopus* Raw-Starch-Degrading Glucoamylase : Its Cloning and Expression in Yeast, >> Agric. Biol. Chem., vol. 50, No. 4, pp. 957-964, 1986.

Ausubel et al., eds., Current Protocols in Molecular Biology, 1994.

Benneft, J. W. et al., ed., << *More Gene Manipulations in Fungi*, Academic Press, San Diego, pp, 70-76, 1991.

Bhikhabhai, Ramagauri et al., << Isolation of Culluoytic Enzymes from *Trichoderma reesei*, QM 9414, >> Journal of Applied Biochemistry, vol. 6, pp. 336-345, 1984.

Boel, E. et al., << Glucoamylases G1 and G2 from *Aspergillus niger* are synthesized from two different but closely related mRNAs, >> The EMBO Journal, vol. 3, No. 5, pp. 1097-1102, 1984.

Boel, E. et al., << Two different types of intervening sequences in the glucoamylase gene from *Aspergillus niger*, >> The EMBO Journal, vol. 3, No. 7, pp. 1581-1585, 1984.

Boel et al., "Calcium binding in alpha-amylases : an X-ray diffraction study at 2.1 angstrom," *Biochemistry*, 1990, V. 29, pp. 6244-6249.

Brumbauer, Aniko et al., << Fractionation of cellulase and β-glucosidase in a *Trichoderma reesei*, Bioseparation, vol. 7, pp. 287-295, 1999.

Campbell, Edward I. et al., << Improved transformation efficiency of *Aspergillus niger*, Current Genetics, vol. 16, pp. 53-56, 1989.

Cao, Qing-Na et al., << Penicillopepsin-JT2, a recombinant enzyme from *Penicillium janthinellum* and the contribution of a hydrogen bond in subsite $S_3$ to $k_{cat}$, >> Protein Science, vol. 9, pp. 991-1001, 2000.

Cees, A. M. et al., << Heterologous Gene Expression in Filamentous Fungi, >> *More Gene Manipulations in Fungi*, Bennett, J.W. et al., ed., pp. 396-428, Academic Press, 1991.

Chen, Hsiu-mei et al., << Identification and elimination by site-directed mutagenesis of thermolabile aspartyl bonds in *Aspergillus awamori* glucoamylase, >> Protein Engineering, vol. 8, No. 6, pp. 575-582, 1995.

Chen, Hsiu-mei et al., << Effect of replacing helical glycine residues with alanines on reversible and irreversible stability and production of *Aspergillus awamori* glucoamylase, Protein Engineering, vol. 9, No. 6, pp, 499-505, 1996.

Chen, Frank Y. et al., << Regulation of mammalian ribonucleotide reductase R1 mRNA stability is mediated by a ribonucleotide reductase R1 mRNA 3-untranslated region cis-trans interaction through a protein kinase C-controlled pathway, >> Biochem. J., vol. 302, pp, 125-132, 1994.

Davis, Rowland H. et al., Genetic and Microbiological Research Techniques for *Neurospora crassa*, << *Methods in Enzymology*, 17A, pp. 79-143, 1970.

Ellouz, S. et al., << Analaytical Separation of *Trichoderma reesei*, Cellulases by Ion-Exchange Fast Protein Liquid Chromatography, >> Journal of Chromatography, vol. 396, pp. 307-327, 1987.

Finkelstein, David B. et al., ed., *Biotechnology of Filamentous Fungi, Technology and Products*, Chapter 6, pp. 113-156, Butterworth-Heinemann, Boston, MA, 1992.

Fliess, A. et al., << Characterization of Cellulases by HPLC Separation, >> Eur. J. Appl. Microbiol. Biotechnol., vol. 17, pp. 314-318, 1983.

Flor, Perfecto Q. et al., << Production and Characteristics of Raw Starch-Digesting Glucoamylase O from a Protease-Negative, Glycosidase-Negative *Aspergillus awamori* var. *kawachi* Mutant, Applied and Environmental Microbiology, vol. 34, No. 3, pp. 905-912, Mar. 1983.

Foreman, Pamela K. et al., << Transcriptional Regulation of Biomass-degrading Enzymes in the Filamentous Fungus *Trichoderma reesei*, Journal of Biological Chemistry, vol. 278, No. 34, pp. 31988-31997, Aug. 22, 2003.

Fujii, Michihiro et al., << Synergism of α-Amylase and Glucoamylase on Hydrolysis of Native Starch Granules, >> Biotechnology and Bioengineering, vol. 32, pp. 910-915, 1988.

Goedegebuur, Frits et al., << Cloning and relational analysis of 15 novel fungal endoglucanases from family 12 glycosyl hydrolase, >> Current Genetics, vol. 41, pp. 89-98, 2002.

Goto, Masatoshi et al., <<0 The Mechanism of Binding of Glucoamylase I from *Aspergillus awamori* var. *kawachi* to Cyclodextrins and Raw Starch, >> Biosci. Biotech. Biochem., vol. 58, No. 1, pp. 49-54, 1994.

Goyal, Anil et al., << Characteristics of Fungal Cellulases, << Bioresource Technology, vol. 36, pp. 37-50, 1991.

Harkki, A. et al., << A Novel Fungal Expression System : Secretion of Active Calf Chymosin from the Filamentous Fungus *Trichoderma reesei*, << Bio/Technology, vol. 7, pp. 596-603, Jun. 1989.

Harkki, Anu et al., << Genetic engineering of *Trichoderma* to produce strains with novel cellulase profiles, >> Enzyme Microb. Technol., vol. 13, pp, 227-233, Mar. 1991.

Hata, Yoji et al., << The Glucoamylase cDNA from *Aspergillus oryzae* : Its Cloning, Nucleotide Sequence, and Expression in *Saccharomyces cerevisiae*, >> Agric. Biol. Chem., vol. 55, No. 4, pp. 941-949, 1991.

Hayashida, Shinsaku et al., << Molecular Cloning of the Glucoamylase I Gene of *Aspergillus awamori* var. *kawachi* for Localization of the Raw-starch-affinity Site, >> Agric. Biol. Chem., vol. 53, No. 4, pp. 923-929, 1989.

Ilmen, Marja et al., << Regulation of Cellulase Gene Expression in the Filamentous Fungus *Trichoderma reesei*, >> Applied and Environmental Microbiology, vol. 63, No, 4, pp. 1298-1306, Apr. 1997.

Innis, M. A. et al., << Expression, Glycosylation, and Secretion of an *Aspergillus* Glucoamylase by *Saccharomyces cerevisiae*, >> Science, vol, 228, pp. 21-26, 1985.

Jacques, K. et al., ed., *The Alcohol Textbook, A Reference for the Beverage, Fuel and Industrial Alcohol Industries*, 3rd ed., Nottingham University Press, 1999.

Jensen, Bo et al., << Purification of extracellular amylotic enzymes from the thermophilic fungus *Thermomyces lanuginosus*, Can. J. Microbiol., vol. 34, pp. 218-223, 1988.

Kaneko, Akihiro et al., << Molecular Cloning and Determination of the Nucleotide Sequence of a Gene Encoding an Acid-Stable α-Amylase from *Aspergillus kawachii*, Journal of Fermentation and Bioengineering, vol. 81, No. 4, pp. 292-298, 1996.

Kelly, Joan M. et al., << Transformation of *Aspergillus niger* by the *amd*S gene of *Aspergillus nidulans*, >> The EMBO Journal, vol. 4, No. 2, pp. 475-479, 1985.

Medve, Jozsef et al., << Ion-exchange chromatogaphic purification and quantitative analysis of *Trichoderma reesei* cellulases cellabiohydrolase I, II and endoglucanase II by fast protein liquid chromatography, >> Journal of Chromatography A, vol. 808, pp. 153-165, 1998.

Miller, Gail L., Use of Dinitrosalicyclic Acid Reagent for Determination of Reducing Sugar, >> Analytical Chemistry, vol. 31, pp. 426-428, 1959.

Nevalainen, K. M. Helena et al., >> The Moleclar Biology of *Trichoderma* and Its Application to the Expression of Both Homologous and Heterologous Genes, >> *Molecular Industrial Mycology*, Leong and Berka, ed., Marcel Dekker, Inc., NY, pp. 129-148, 1992.

Nunberg, Jack H. et al., << Molecular Cloning and Characterization of the Glucoamylase Gene of *Aspergillus awamori*, Molecular and Cellular Biology, pp. 2306-2315, Nov. 1984.

Pearson, William R. et al., << Improved tools for biological sequence comparison, >> Proc. Natl. Acad. Sci., U.S.A., vol. 85, pp. 2444-2448, Apr. 1988.

Penttila, Merja et al., << A versatile transformation system for the cellulolytic filamentous fungus *Trichoderma reesei*, >> Gene, vol. 61, pp. 155-164, 1987.

Pourquie, J. et al., << Scale Up of Cellulase Production and Utilization, >> *Biochemistry and Genetics of Cellulose Degradation*, Aubert, J. P. et al., ed., Academic Press, pp. 71-86, 1988.

Sambrook et al., *Molecular Cloning : A Laboratory Manual*, $2^{nd}$ ed., chapters 9 and 11, 1989.

Sheir-Neiss, G. et al., << Characterization of the secreted cellulases of *Trichoderma reesei* wild type and mutants during controlled fermentations, >> Appl. Microbiol. Biotechnol., vol. 20, pp. 46-53, 1984.

Shibuya, Ichiro et al., Molecular Cloning of the Glucoamylase Gene of *Aspergillus shirousami* and Its Expression in *Aspergillus oryzae*, << Agric. Biol. Chem., vol. 54, No. 8, pp. 1905-1914, 1990.

Singleton et al., << Dictionary of Microbiology and Molecular Biology, $2^{nd}$ ed., John Wiley and Sons, New York, 1994.

Swinkels, J. J. M., *Starch Conversion Technology*, van Beynum et al. ed., Marcel Dekker, Inc., New York, pp. 15-45, 1985.

Takahashi, Tomoko et al., << Different Behavior towards Raw Starch of Three Forms of Glucoamylase from a *Rhizopus* sp., >> J. Biochem., vol. 98, pp. 663-671, 1985.

Taylor, Pamela M. et al., << Some Properties of a Glucoamylase Produced by the Thermophilic Fungus *Humicola lanuginosa*, >>Carbohydrate Research, vol. 61, pp. 301-308, 1978.

Tomaz, Candida T. et al., << Studies on the chromatographic fractionation of *Trichoderma reesei* cellulases by hydrophobic interaction, >> Journal of Chromatography A, vol. 866, pp. 123-128, 1999.

Tosi, Luis Ricardo Orsini et al., << Purification and characterization of an extracellular glycoamylase from the thermophilic fungus *Humicola grisea* var. *thermoidea*, >>Can J. Microbiol., vol. 39, pp. 846-855, 1993.

Van Tilbeurgh, Herman et al., << Separation of endo- and exo-type cellulases using a new affinity chromatography method, vol. 169, No. 2, pp. 216-218, FEBS, vol. 169, No. 2, Apr. 1984.

Ward, Michael et al., << Use of *Aspergillus* overproducing mutants, cured for integrated plasmid, to overproduce heterologous proteins, >> Appl. Microbiol. Biotechnol., vol. 39, pp, 738-743, 1993.

Takahasi, Tomoko et al., << Different Behavior towards Raw Starch of Three Forms of Glucoamylase from a *Rhizopus* sp., >> J. Biochem., vol. 98, pp. 663-671, 1985.

Taylor, Pamela M. et al., << Some Properties of a Glucoamylase Produced by the Thermophilic Fungus *Humicola ianuginosa*, >>Carbohydrate Research, vol. 61, pp, 301-308, 1978.

Tomaz, Candida T. et al., << Studies on the chromatographic fractionation of *Trichoderma reesei* cellulases by hydrophobic interaction, >> Journal of Chromatography A, vol. 865, pp. 123-128, 1999.

Tosi, Luis Ricardo Orsini et al., << Purification and characterization of an extracellular glycoamylase from the thermophilic fungus *Humicola grisea* var. *thermoidea*. >>Can J. Microbiol., vol. 39, pp. 846-855, 1993.

Van Tilbeurgh, Herman et al., << Separation of endo- and exo-type cellulases using a new affinity chromatography method, >> vol. 169, No. 2, pp, 215-218, FEBS, vol. 169, No. 2, Apr. 1984.

Ward, Michael et al., << Use of *Aspergillus* overproducing mutants, cured for integrated plasmid, to overproduce heterologous proteins, >> Appl. Microbiol. Biotechnol., vol. 39, pp. 738-743, 1993.

Fagerstrom, Richard, << Purification and specificity of recombinant *Hormoconis resinae* glucoamylase P and endogenous glucoamylase from *Trichoderma reesei*, Enzyme Microb. Technol., vol. 16, pp. 36-42, 1994.>>.

Wiebe, Marilyn G. et al., << Growth-Rate-Independent Production of Recombinant Glucoamylase by *Fusarium venenatum* JeRS 325, Biotechnology and Bioengineering, vol. 68, No. 3, pp. 245-251, May 5, 2000.>>.

Withers, Julie M. et al., << Optimization and Stability of Glucoamylase Production by Recombinant Strains of *Aspergillus niger* in Chemostat Culture, Biotechnology and Bioengineering, vol. 59, No. 4, pp. 407-418, Aug. 20, 1998.>>.

Database UniProt 'Online !, Nov. 1, 1994, Glucoamylase, >> XP002325133, retrieved from EBI accession No. UNIPROT:Q12623.

Brown, S. W. and Oliver, S. G., "The Effect of Temperature on the Ethanol Tolerance of the Yeast," *Biotechnology Letters*, 4:269-274 (1982).

Casey, G. P. and Ingledew, W. M., "Reevaluation of Alcohol Synthesis and Tolerance in Brewer's Yeast," *Journal of the American Society of Brewing Chemists*, Inc. 43(2):75-83 (1985).

Han, I et al.,t "Amylolysis of Raw Corn by *Aspergillus niger* for Simultaneous Ethanol Fermentation," *Biotechnology and Bioengineering*, 30:225-233 (1987).

Hayashida, S., "Selective Submerged Productions of Three Types of Glucoamylases by a Black-koji Mold," *Agr. Biol. Chem.*, 39(11):2093-2099 (1975).

Jones, A. M. and Ingledew, W. M., "Fuel Alcohol Production: Optimization of Temperature for Efficient Very-High-Gravity Fermentation," *Appl. Environ. Microbiol.*, 60(3):1048-1051 (1994).

Lewis, S. M., "Fermentation Alcohol". Chapter 2.1 in *Industrial Enzymology* ($2^{nd}$ Ed. 1996).

Matsumoto, N. et al., "Industrialization of a Noncooking System for Alcoholic Fermentation from Grains," *Agric. Biol. Chem.*, 46(6):1549-1558 (1982).

Matsuoka, H. et al., "Alcoholic Fermentation of Sweet Potato without Cooking," *Journal of Fermentation Technology*, 60(6):599-602 (1982).

Medda, S. et al., "Glucoamylase I of Black *Aspergillus*," *J. Fac. Agr., Kyushu Univ.*, 26 (2.3), 139-149 (1982).

Sa-Correia, I. and Van Uden, N., "Effects of Ethanol on Thermal Death and on the Maximum Temperature for Growth of the Yeast *Kluyveromyces fragilis*," *Biotechnol. Lett.*, 4(12):805-808 (1982).

Saha, B. et al., "Alcoholic Fermentation of Raw Sweet Potato by a Nonconventional Method Using *Endomycopsis fibuligera* Glucoamylase Preparation," *Biotechnology and Bioengineering*, 25:1181-1186 (1983).

Ueda, S. et al., "Alcoholic Fermentation of Raw Starch without Cooking by Using Black-*koji* Amylase," *Ferment. Technol.*, 58(3):237-242 (1980).

Ueda, S. et al., "Direct Hydrolysis of Raw Starch," *Microbiological Sciences*, 1(1):21-24 (1984).

Van Uden, N. and da Cruz Duarte, H., Effects of Ethanol on the Temperature Profile of *Saccharomyces cerevisiae, Zeitsch. Allg. Mikrobiol.*, 21(10):743-750 (1981).

Van Uden, N. et al., "Effects of Ethanol on Yeast Performance: Targets and Underlying Mechanisms," *Proceedings of the 19th Congress of European Brewery Convention*, pp. 137-144 (1983).

Bergquist, Peter et al., << Expression of xylanase enzymes from thermophilic microorganisms in fungal hosts, >> Extremophiles, vol. 6, pp. 177-184, 2002.

Cheng, Cheng et al., << Efficient Production of Taka-amylase A by *Trichoderma viride*, >> Agric. Biol. Chem., vol. 55, No. 7, pp. 1817-1822, 1991.

Kajiwara, Yasuhiro et al., << Production of Acid-Stable α-Amylase by *Aspergillus kawachii* during Barley *Shochu-Koji* Production, >> Journal of Fermentation and Bioengineering, vol. 84, No. 3, pp. 224-227, 1997.

Morimura, Shigeru et al., << Genetic Engineering of White *Shochu-Koji* to Achieve Higher Levels of Acid-Stable α-Amylase and Glucoamylase and Other Properties When Used for *Shochu* Making on a Laboratory Scale, >> Journal of the Institute of Brewing, vol. 105, No. 5, pp, 309-314, Sep. 1999.

\* cited by examiner (SEQ ID NO: 1)

ATGAGAGTGTCGACTTCAAGTATTGCCCTTGCTGTGTCCCTTTTTGGGAAGCTGGCCCTTGGGC
TGTCAGCTGCAGAATGGCGCACTCAATCCATCTACTTCCTTTTGACGGATCGGTTCGGTAGGAC
GGACAATTCGACTACAGCTACGTGCAATACGGGTGACCAA<u>GTATGGTATTGCTGTACTTCCGTC
ATTCATCTGCTGACTTGGATAG</u>ATCTACTGTGGTGGAAGTTGGCAAGGAATTATCAACCAT<u>GTT
CGTATCTCACTTCATACCATCCATGCTGGGCGCTTCTGACTATTGCTCCAGCTGGACTATATCC</u>
AGGGCATGGGATTCACAGCTATCTGGATCTCGCCTATCACTGAGCAGCTACCCCAGGATACTTC
GGATGGTGAAGCCTACCATGGATACTGGCAGCAGAAGAT<u>GTATGCCCTCATTGCATTCATATTT
TATGCTTACTCGCAGACTGCAGCTGACTTGGCAG</u>ATACAATGTGAACTCCAACTTCGGCACGGC
AGATGATCTGAAGTCCCTCTCCGATGCTCTTCACGCCCGCGGAATGTACCTCATGGTCGACGTC
GTCCCTAACCACAT<u>GGTAAGTACTGCTTTACCTCTATATTAGTAAACCCAATGCGAACAATGAC
TGTATCAG</u>GGCTACGCAGGTAACGGCAACGATGTGGATTACAGCGTCTTCGACCCCTTCGACTC
CTCCTCCTACTTCCATCCATACTGCCTCATCACAGATTGGGACAACTTGACCATGGTCCAAGAC
TGTTGGGAGGGTGACACCATCGTGTCTCTGCCAGATCTGAACACCACGGAAACCGCCGTGAGAA
CCATTTGGTACGATTGGGTAGCCGACCTGGTATCCAACTACTCAG<u>GTGCGACCCCAACCCACTA
AAACAAGCCACATACTAAAAAATTGCTCAG</u>TCGACGGCCTCCGTATCGACAGTGTCGAAGAAGT
CGAACCCGACTTCTTCCCGGGCTACCAAGAAGCAGCAGGAGTCTACTGCGTCGGTGAAGTCGAC
AACGGCAACCCTGCTCTCGACTGCCCATACCAAAAATATCTAGATGGTGTTCTCAACTATCCCA
T<u>GTACATACCCCCTTCTACCTTCTCGAACCCATCACTAACTCAATTGCTGCAG</u>CTACTGGCAAC
TCCTCTACGCCTTTGAATCCTCCAGCGGCAGCATCAGCAACCTCTACAACATGATCAAATCCGT
CGCCAGCGACTGCTCCGATCCGACCCTCCTGGGCAACTTTATCGAAAACCACGACAACCCCCGC
TTCGCCCTC<u>GTATGTCCCTTCCATCACTGCCCCCTTTTAAAGTAAACCCCACTGACAGGCAAAGC</u>
TACACATCCGACTACTCCCAAGCCAAAAACGTCCTCAGCTACATCTTCCTCTCCGACGGCATCC
CCATCGTCTACGCCGGCGAAGAACAGCACTACTCCGGCGGCGACGTGCCCTACAACCGCGAAGC
TACCTGGCTATCAGGCTACGACACCTCCGCGGAGCTCTACACCTGGATAGCCACCACAAACGCG
ATCCGGAAACTAGCTATCTCAGCAGACTCGGACTACATTACTTACGCGG<u>TTTGCCCTTTCCCTT
CCCCCCACCCAGAGCTCAACCCCCATTCTAACAAAATATTTCAATG</u>GTAGAACGACCCAATCTA
CACAGACAGCAACACCATCGCGATGCGCAAAGGCACCTCCGGCTCCCAAATCATCACCGTCCTC
TCCAACAAAGGCTCCTCCGGAAGCAGCTACACCCTCACCCTCAGCGGAAGCGGCTACACGTCCG
GCACGAAGCTCATCGAAGCGTACACCTGCACGTCCGTGACGGTGGACTCGAACGGGGATATCCC
TGTGCCGATGGCTTCGGGATTACCTAGAGTTCTCCTCCCTGCTTCGGTGGTTGATAGTTCTTCG
CTTTGTGGGGGGAGTGGTAACACAACCACGACCACAACTGCTGCTACCTCCACATCCAAAGCCA
CCACCTCCTCTTCTTCTTCTTCTGCTGCTGCTACTACTTCTTCATCATGCACCGCAACAAGCAC
CACCCTCCCCATCACCTTCGAAGAACTCGTCACCACTACCTACGGGGAAGAAGTCTACCTCAGC
GGATCTATCTCCCAGCTCGGAGAGTGGGATACGAGTGACGCGGTGAAGTTGTCCGCGGATGATT
ATACCTCGAGTAACCCCGAGTGGTCTGTTACTGTGTCGTTGCCGGTGGGGACGACCTTCGAGTA
TAAGTTTATTAAGGTCGATGAGGGTGGAAGTGTGACTTGGGAAAGTGATCCGAATAGGGAGTAT
ACTGTGCCTGAATGTGGGAGTGGGAGTGGGGAGACGGTGGTTGATACGTGGAGGTAG

FIG. 1

(SEQ ID NO: 4)

MRVSTSSIALAVSLFGKLALGLSAAEWRTQSIYFLLTDRFGRTDNSTTATCNTGDQIYCGGS
WQGIINHLDYIQGMGFTAIWISPITEQLPQDTSDGEAYHGYWQQKIYNVNSNFGTADDLKSL
SDALHARGMYLMVDVVPNHMGYAGNGNDVDYSVFDPFDSSSYFHPYCLITDWDNLTMVQDCW
EGDTIVSLPDLNTTETAVRTIWYDWVADLVSNYSVDGLRIDSVEEVEPDFFPGYQEAAGVYC
VGEVDNGNPALDCPYQKYLDGVLNYPIYWQLLYAFESSSGSISNLYNMIKSVASDCSDPTLL
GNFIENHDNPRFASYTSDYSQAKNVLSYIFLSDGIPIVYAGEEQHYSGGDVPYNREATWLSG
YDTSAELYTWIATTNAIRKLAISADSDYITYANDPIYTDSNTIAMRKGTSGSQIITVLSNKG
SSGSSYTLTLSGSGYTSGTKLIEAYTCTSVTVDSNGDIPVPMASGLPRVLLPASVVDSSSLC
GGSGN<u>TTTTTTAATSTSKATTSSSSSSAAATTSSSCTATSTT</u>LPITFEELVTTTYGEEVYLS
GSISQLGEWDTSDAVKLSADDYTSSNPEWSVTVSLPVGTTFEYKFIKVDEGGSVTWESDPNR
EYTVPECGSGSGETVVDTWR

FIG. 2

(SEQ ID NO: 5)

CTGCAGCCACTTGCAGTCCCGTGGAATTCTCACGGTGAATGTAGGCCTTTTGTAGGGTAGGAAT
TGTCACTCAAGCACCCCCAACCTCCATTACGCCTCCCCCATAGAGTTCCCAATCAGTGAGTCAT
GGCACTGTTCTCAAATAGATTGGGGAGAAGTTGACTTCCGCCCAGAGCTGAAGGTCGCACAACC
GCATGATATAGGGTCGGCAACGGCAAAAAGCACGTGGCTCACCGAAAAGCAAGATGTTTGCGA
TCTAACATCCAGGAACCTGGATACATCCATCATCACGCACGACCACTTTGATCTGCTGGTAAAC
TCGTATTCGCCCTAAACCGAAGTGCGTGGTAAATCTACACGTGGGCCCCTTTCGGTATACTGCG
TGTGTCTTCTCTAGGTGCCATTCTTTTCCCTTCCTCTAGTGTTGAATTGTTTGTGTTGGAGTCC
GAGCTGTAACTACCTCTGAATCTCTGGAGAATGGTGGACTAACGACTACCGTGCACCTGCATCA
TGTATATAATAGTGATCCTGAGAAGGGGGGTTTGGAGCAATGTGGGACTTTGATGGTCATCAAA
CAAAGAACGAAGACGCCTCTTTTGCAAAGTTTTGTTTCGGCTACGGTGAAGAACTGGATACTTG
TTGTGTCTTCTGTGTATTTTTGTGGCAACAAGAGGCCAGAGACAATCTATTCAAACACCAAGCT
TGCTCTTTTGAGCTACAAGAACCTGTGGGGTATATATCTAGAGTTGTGAAGTCGGTAATCCCGC
TGTATAGTAATACGAGTCGCATCTAAATACTCCGAAGCTGCTGCGAACCCGGAGAATCGAGATG
TGCTGGAAAGCTTCTAGCGAGCGGCTAAATTAGCATGAAAGGCTATGAGAAATTCTGGAGACGG
CTTGTTGAATCATGGCGTTCCATTCTTCGACAAGCAAAGCGTTCCGTCGCAGTAGCAGGCACTC
ATTCCCGAAAAACTCGGAGATTCCTAAGTAGCGATGGAACCGGAATAATATAATAGGCAATAC
ATTGAGTTGCCTCGACGGTTGCAATGCAGGGGTACTGAGCTTGGACATAACTGTTCCGTACCCC
ACCTCTTCTCAACCTTTGGCGTTTCCCTGATTCAGCGTACCCGTACAAGTCGTAATCACTATTA
ACCCAGACTGACCGGACGTGTTTTGCCCTTCATTTGGAGAAATAATGTCATTGCGATGTGTAAT
TTGCCTGCTTGACCGACTGGGGCTGTTCGAAGCCCGAATGTAGGATTGTTATCCGAACTCTGCT
CGTAGAGGCATGTTGTGAATCTGTGTCGGGCAGGACACGCCTCGAAGGTTCACGGCAAGGGAAA
CCACCGATAGCAGTGTCTAGTAGCAACCTGTAAAGCCGCAATGCAGCATCACTGGAAAATACAA
ACCAATGGCTAAAAGTACATAAGTTAATGCCTAAAGAAGTCATATACCAGCGGCTAATAATTGT
ACAATCAAGTGGCTAAACGTACCGTAATTTGCCAACGGCTTGTGGGGTTGCAGAAGCAACGGCA
AAGCCCCACTTCCCCACGTTTGTTTCTTCACTCAGTCCAATCTCAGCTGGTGATCCCCCAATTG
GGTCGCTTGTTTGTTCCGGTGAAGTGAAAGAAGACAGAGGTAAGAATGTCTGACTCGGAGCGTT
TTGCATACAACCAAGGGCAGTGATGGAAGACAGTGAAATGTTGACATTCAAGGAGTATTTAGCC
AGGGATGCTTGAGTGTATCGTGTAAGGAGGTTTGTCTGCCGATACGACGAATACTGTATAGTCA
CTTCTGATGAAGTGGTCCATATTGAAATGTAAGTCGGCACTGAACAGGCAAAAGATTGAGTTGA
AACTGCCTAAGATCTCGGGCCCTCGGGCCTTCGGCCTTTGGGTGTACATGTTTGTGCTCCGGGC
AAATGCAAAGTGTGGTAGGATCGAACACACTGCTGCCTTTACCAAGCAGCTGAGGGTATGTGAT
AGGCAAATGTTCAGGGGCCACTGCATGGTTTCGAATAGAAAGAGAAGCTTAGCCAAGAACAATA
GCCGATAAAGATAGCCTCATTAAACGGAATGAGCTAGTAGGCAAAGTCAGCGAATGTGTATATA
TAAAGGTTCGAGGTCCGTGCCTCCCTCATGCTCTCCCCATCTACTCATCAACTCAGATCCTCCA
GGAGACTTGTACACCATCTTTTGAGGCACAGAAACCCAATAGTCAACCATCACAAGTTTGTACA
AAAAAGCAGGCTCCGCGGCCGCCCCCTTCAcCATGAGAGTGTCGACTTCAAGTATTGCCCTTGC
TGTGTCCCTTTTTGGGAAGCTGGCCCTTGGGCTGTCAGCTGCAGAATGGCGCACTCAATCCATC
TACTTCCTTTTGACGGATCGGTTCGGTAGGACGGACAATTCGACTACAGCTACGTGCAATACGG
GTGACCAAGTATGGTATTGCTGTACTTCCGTCATTCATCTGCTGACTTGGATAGATCTACTGTG
GTGGAAGTTGGCAAGGAATTATCAACCATGTTCGTATCTCACTTCATACCATCCATGCTGGGCG
CTTCTGACTATTGCTCCAGCTGGACTATATCCAGGGCATGGGATTCACAGCTATCTGGATCTCG
CCTATCACTGAGCAGCTACCCCAGGATACTTCGGATGGTGAAGCCTACCATGGATACTGGCAGC
AGAAGATGTATGCCCTCATTGCATTCATATTTTATGCTTACTCGCAGACTGCAGCTGACTTGGC
AGATACAATGTGAACTCCAACTTCGGCACGGCAGATGATCTGAAGTCCCTCTCCGATGCTCTTC
ACGCCCGCGGAATGTACCTCATGGTCGACGTCGTCCCTAACCACATGGTAAGTACTGCTTTACC

*FIG. 3A*

```
TCTATATTAGTAAACCCAATGCGAACAATGACTGTATCAGGGCTACGCAGGTAACGGCAACGAT
GTGGATTACAGCGTCTTCGACCCCTTCGACTCCTCCTCCTACTTCCATCCATACTGCCTCATCA
CAGATTGGGACAACTTGACCATGGTCCAAGACTGTTGGGAGGGTGACACCATCGTGTCTCTGCC
AGATCTGAACACCACGGAAACCGCCGTGAGAACCATTTGGTACGATTGGGTAGCCGACCTGGTA
TCCAACTACTCAGGTGCGACCCCAACCCACTAAAACAAGCCACATACTAAAAAATTGCTCAGTC
GACGGCCTCCGTATCGACAGTGTCGAAGAAGTCGAACCCGACTTCTTCCCGGGCTACCAAGAAG
CAGCAGGAGTCTACTGCGTCGGTGAAGTCGACAACGGCAACCCTGCTCTCGACTGCCCATACCA
AAAATATCTAGATGGTGTTCTCAACTATCCCATGTACATACCCCCTTCTACCTTCTCGAACCCA
TCACTAACTCAATTGCTGCAGCTACTGGCAACTCCTCTACGCCTTTGAATCCTCCAGCGGCAGC
ATCAGCAACCTCTACAACATGATCAAATCCGTCGCCAGCGACTGCTCCGATCCGACCCTCCTGG
GCAACTTTATCGAAAACCACGACAACCCCGCTTCGCCTCGTATGTCCCTTCCATCACTGCCCC
CTTTTAAAGTAAACCCCACTGACAGGCAAAGCTACACATCCGACTACTCCCAAGCCAAAAACGT
CCTCAGCTACATCTTCCTCTCCGACGGCATCCCCATCGTCTACGCCGGCGAAGAACAGCACTAC
TCCGGCGGCGACGTGCCCTACAACCGCGAAGCTACCTGGCTATCAGGCTACGACACCTCCGCGG
AGCTCTACACCTGGATAGCCACCACAAACGCGATCCGGAAACTAGCTATCTCAGCAGACTCGGA
CTACATTACTTACGCGGTTTGCCCTTTCCCTTCCCCCCACCCAGAGCTCAACCCCCATTCTAAC
AAAATATTTCAATGGTAGAACGACCCAATCTACACAGACAGCAACACCATCGCGATGCGCAAAG
GCACCTCCGGCTCCCAAATCATCACCGTCCTCTCCAACAAAGGCTCCTCCGGAAGCAGCTACAC
CCTCACCCTCAGCGGAAGCGGCTACACGTCCGGCACGAAGCTCATCGAAGCGTACACCTGCACG
TCCGTGACGGTGGACTCGAACGGGGATATCCCTGTGCCGATGGCTTCGGGATTACCTAGAGTTC
TCCTCCCTGCTTCGGTGGTTGATAGTTCTTCGCTTTGTGGGGGGAGTGGTAACACAACCACGAC
CACAACTGCTGCTACCTCCACATCCAAAGCCACCACCTCCTCTTCTTCTTCTGCTGCTGCT
ACTACTTCTTCATCATGCACCGCAACAAGCACCACCCTCCCCATCACCTTCGAAGAACTCGTCA
CCACTACCTACGGGGAAGAAGTCTACCTCAGCGGATCTATCTCCCAGCTCGGAGAGTGGGATAC
GAGTGACGCGGTGAAGTTGTCCGCGGATGATTATACCTCGAGTAACCCCGAGTGGTCTGTTACT
GTGTCGTTGCCGGTGGGGACGACCTTCGAGTATAAGTTTATTAAGGTCGATGAGGGTGGAAGTG
TGACTTGGGAAAGTGATCCGAATAGGGAGTATACTGTGCCTGAATGTGGGAGTGGGAGTGGGGA
GACGGTGGTTGATACGTGGAGGTAGAAGGGTGGGCGCGCCGACCCAGCTTTcttgtacaaagtg
gtgatcgcgccAGCTCCGTGCGAAAGCCTGACGCACCGGTAGATTCTTGGTGAGCCCGTATCAT
GACGGCGGCGGGAGCTACATGGCCCCGGGTGATTTATTTTTTTGTATCTACTTCTGACCCTTT
TCAAATATACGGTCAACTCATCTTTCACTGGAGATGCGGCCTGCTTGGTATTGCGATGTTGTCA
GCTTGGCAAATTGTGGCTTTCGAAAACACAAAACGATTCCTTAGTAGCCATGCATTTTAAGATA
ACGGAATAGAAGAAGAGGAAATTAAAAAAAAAAAAAAAACAAACATCCCGTTCATAACCCGTA
GAATCGCCGCTCTTCGTGTATCCCAGTACCAGTTTATTTTGAATAGCTCGCCCGCTGGAGAGCA
TCCTGAATGCAAGTAACAACCGTAGAGGCTGACACGGCAGGTGTTGCTAGGGAGCGTCGTGTTC
TACAAGGCCAGACGTCTTCGCGGTTGATATATATGTATGTTTGACTGCAGGCTGCTCAGCGACG
ACAGTCAAGTTCGCCCTCGCTGCTTGTGCAATAATCGCAGTGGGGAAGCCACACCGTGACTCCC
ATCTTTCAGTAAAGCTCTGTTGGTGTTTATCAGCAATACACGTAATTTAAACTCGTTAGCATGG
GGCTGATAGCTTAATTACCGTTTACCAGTGCCATGGTTCTGCAGCTTTCCTTGGCCCGTAAAAT
TCGGCGAAGCCAGCCAATCACCAGCTAGGCACCAGCTAAACCCTATAATTAGTCTCTTATCAAC
ACCATCCGCTCCCCGGGATCAATGAGGAGAATGAGGGGGATGCGGGGCTAAAGAAGCCTACAT
AACCCTCATGCCAACTCCCAGTTTACACTCGTCGAGCCAACATCCTGACTATAAGCTAACACAG
AATGCCTCAATCCTGGGAAGAACTGGCCGCTGATAAGCGCGCCCGCCTCGCAAAAACCATCCCT
GATGAATGGAAAGTCCAGACGCTGCCTGCGGAAGACAGCGTTATTGATTTCCCAAAGAAATCGG
GGATCCTTTCAGAGGCCGAACTGAAGATCACAGAGGCCTCCGCTGCAGATCTTGTGTCCAAGCT
```

*FIG. 3B*

```
GGCGGCCGGAGAGTTGACCTCGGTGGAAGTTACGCTAGCATTCTGTAAACGGGCAGCAATCGCC
CAGCAGTTAGTAGGGTCCCCTCTACCTCTCAGGGAGATGTAACAACGCCACCTTATGGGACTAT
CAAGCTGACGCTGGCTTCTGTGCAGACAAACTGCGCCCACGAGTTCTTCCCTGACGCCGCTCTC
GCGCAGGCAAGGGAACTCGATGAATACTACGCAAAGCACAAGAGACCCGTTGGTCCACTCCATG
GCCTCCCCATCTCTCTCAAAGACCAGCTTCGAGTCAAGGTACACCGTTGCCCCTAAGTCGTTAG
ATGTCCCTTTTTGTCAGCTAACATATGCCACCAGGGCTACGAAACATCAATGGGCTACATCTCA
TGGCTAAACAAGTACGACGAAGGGGACTCGGTTCTGACAACCATGCTCCGCAAAGCCGGTGCCG
TCTTCTACGTCAAGACCTCTGTCCCGCAGACCCTGATGGTCTGCGAGACAGTCAACAACATCAT
CGGGCGCACCGTCAACCCACGCAACAAGAACTGGTCGTGCGGCGGCAGTTCTGGTGGTGAGGGT
GCGATCGTTGGGATTCGTGGTGGCGTCATCGGTGTAGGAACGGATATCGGTGGCTCGATTCGAG
TGCCGGCCGCGTTCAACTTCCTGTACGGTCTAAGGCCGAGTCATGGGCGGCTGCCGTATGCAAA
GATGGCGAACAGCATGGAGGGTCAGGAGACGGTGCACAGCGTTGTCGGGCCGATTACGCACTCT
GTTGAGGGTGAGTCCTTCGCCTCTTCCTTCTTTTCCTGCTCTATACCAGGCCTCCACTGTCCTC
CTTTCTTGCTTTTTATACTATATACGAGACCGGCAGTCACTGATGAAGTATGTTAGACCTCCGC
CTCTTCACCAAATCCGTCCTCGGTCAGGAGCCATGGAAATACGACTCCAAGGTCATCCCCATGC
CCTGGCGCCAGTCCGAGTCGGACATTATTGCCTCCAAGATCAAGAACGGCGGGCTCAATATCGG
CTACTACAACTTCGACGGCAATGTCCTTCCACACCCTCCTATCCTGCGCGGCGTGGAAACCACC
GTCGCCGCACTCGCCAAAGCCGGTCACACCGTGACCCGTGGACGCCATACAAGCACGATTTCG
GCCACGATCTCATCTCCCATATCTACGCGGCTGACGGCAGCGCCGACGTAATGCGCGATATCAG
TGCATCCGGCGAGCCGGCGATTCCAAATATCAAAGACCTACTGAACCCGAACATCAAAGCTGTT
AACATGAACGAGCTCTGGGACACGCATCTCCAGAAGTGGAATTACCAGATGGAGTACCTTGAGA
AATGGCGGGAGGCTGAAGAAAGGCCGGGAAGGAACTGGACGCCATCATCGCGCCGATTACGCC
TACCGCTGCGGTACGGCATGACCAGTTCCGGTACTATGGGTATGCCTCTGTGATCAACCTGCTG
GATTTCACGAGCGTGGTTGTTCCGGTTACCTTTGCGGATAAGAACATCGATAAGAAGAATGAGA
GTTTCAAGGCGGTTAGTGAGCTTGATGCCCTCGTGCAGGAAGAGTATGATCCGGAGGCGTACCA
TGGGGCACCGGTTGCAGTGCAGGTTATCGGACGGAGACTCAGTGAAGAGAGGACGTTGGCGATT
GCAGAGGAAGTGGGGAAGTTGCTGGGAAATGTGGTGACTCCATAGCTAATAAGTGTCAGATAGC
AATTTGCACAAGAAATCAATACCAGCAACTGTAAATAAGCGCTGAAGTGACCATGCCATGCTAC
GAAAGAGCAGAAAAAAACCTGCCGTAGAACCGAAGAGATATGACACGCTTCCATCTCTCAAAGG
AAGAATCCCTTCAGGGTTGCGTTTCCAGTCTAGACACGTATAACGGCACAAGTGTCTCTCACCA
AATGGGTTATATCTCAAATGTGATCTAAGGATGGAAAGCCCAGAATATCGATCGCGCGCAGATC
CATATATAGGGCCCGGGTTATAATTACCTCAGGTCGACGTCCCATGGCCATTCGAATTCGTAAT
CATGGTCATAGCTGTTTCCTGTGTGAAATTGTTATCCGCTCACAATTCCACACAACATACGAGC
CGGAAGCATAAAGTGTAAAGCCTGGGGTGCCTAATGAGTGAGCTAACTCACATTAATTGCGTTG
CGCTCACTGCCCGCTTTCCAGTCGGGAAACCTGTCGTGCCAGCTGCATTAATGAATCGGCCAAC
GCGCGGGGAGAGGCGGTTTGCGTATTGGGCGCTCTTCCGCTTCCTCGCTCACTGACTCGCTGCG
CTCGGTCGTTCGGCTGCGGCGAGCGGTATCAGCTCACTCAAAGGCGGTAATACGGTTATCCACA
GAATCAGGGGATAACGCAGGAAGAACATGTGAGCAAAAGGCCAGCAAAAGGCCAGGAACCGTA
AAAAGGCCGCGTTGCTGGCGTTTTTCCATAGGCTCCGCCCCCTGACGAGCATCACAAAAATCG
ACGCTCAAGTCAGAGGTGGCGAAACCCGACAGGACTATAAAGATACCAGGCGTTTCCCCCTGGA
AGCTCCCTCGTGCGCTCTCCTGTTCCGACCCTGCCGCTTACCGGATACCTGTCCGCCTTTCTCC
CTTCGGGAAGCGTGGCGCTTTCTCATAGCTCACGCTGTAGGTATCTCAGTTCGGTGTAGGTCGT
TCGCTCCAAGCTGGGCTGTGTGCACGAACCCCCGTTCAGCCCGACCGCTGCGCCTTATCCGGT
AACTATCGTCTTGAGTCCAACCCGGTAAGACACGACTTATCGCCACTGGCAGCAGCCACTGGTA
ACAGGATTAGCAGAGCGAGGTATGTAGGCGGTGCTACAGAGTTCTTGAAGTGGTGGCCTAACTA
```

FIG. 3C

```
CGGCTACACTAGAAGAACAGTATTTGGTATCTGCGCTCTGCTGAAGCCAGTTACCTTCGGAAAA
AGAGTTGGTAGCTCTTGATCCGGCAAACAAACCACCGCTGGTAGCGGTGGTTTTTTTGTTTGCA
AGCAGCAGATTACGCGCAGAAAAAAAGGATCTCAAGAAGATCCTTTGATCTTTTCTACGGGGTC
TGACGCTCAGTGGAACGAAAACTCACGTTAAGGGATTTTGGTCATGAGATTATCAAAAGGATC
TTCACCTAGATCCTTTTAAATTAAAAATGAAGTTTTAAATCAATCTAAAGTATATATGAGTAAA
CTTGGTCTGACAGTTACCAATGCTTAATCAGTGAGGCACCTATCTCAGCGATCTGTCTATTTCG
TTCATCCATAGTTGCCTGACTCCCCGTCGTGTAGATAACTACGATACGGGAGGGCTTACCATCT
GGCCCCAGTGCTGCAATGATACCGCGAGACCCACGCTCACCGGCTCCAGATTTATCAGCAATAA
ACCAGCCAGCCGGAAGGGCCGAGCGCAGAAGTGGTCCTGCAACTTTATCCGCCTCCATCCAGTC
TATTAATTGTTGCCGGGAAGCTAGAGTAAGTAGTTCGCCAGTTAATAGTTTGCGCAACGTTGTT
GCCATTGCTACAGGCATCGTGGTGTCACGCTCGTCGTTTGGTATGGCTTCATTCAGCTCCGGTT
CCCAACGATCAAGGCGAGTTACATGATCCCCCATGTTGTGCAAAAAAGCGGTTAGCTCCTTCGG
TCCTCCGATCGTTGTCAGAAGTAAGTTGGCCGCAGTGTTATCACTCATGGTTATGGCAGCACTG
CATAATTCTCTTACTGTCATGCCATCCGTAAGATGCTTTTCTGTGACTGGTGAGTACTCAACCA
AGTCATTCTGAGAATAGTGTATGCGGCGACCGAGTTGCTCTTGCCCGGCGTCAATACGGGATAA
TACCGCGCCACATAGCAGAACTTTAAAAGTGCTCATCATTGGAAAACGTTCTTCGGGGCGAAAA
CTCTCAAGGATCTTACCGCTGTTGAGATCCAGTTCGATGTAACCCACTCGTGCACCCAACTGAT
CTTCAGCATCTTTTACTTTCACCAGCGTTTCTGGGTGAGCAAAAACAGGAAGGCAAAATGCCGC
AAAAAAGGGAATAAGGGCGACACGGAAATGTTGAATACTCATACTCTTCCTTTTTCAATATTAT
TGAAGCATTTATCAGGGTTATTGTCTCATGAGCGGATACATATTTGAATGTATTTAGAAAAATA
AACAAATAGGGGTTCCGCGCACATTTCCCCGAAAAGTGCCACCTGACGTCTAAGAAACCATTAT
TATCATGACATTAACCTATAAAAATAGGCGTATCACGAGGCCCTTTCGTCTCGCGCGTTTCGGT
GATGACGGTGAAAACCTCTGACACATGCAGCTCCCGGAGACGGTCACAGCTTGTCTGTAAGCGG
ATGCCGGGAGCAGACAAGCCCGTCAGGGCGCGTCAGCGGGTGTTGGCGGGTGTCGGGGCTGGCT
TAACTATGCGGCATCAGAGCAGATTGTACTGAGAGTGCACCATAAAATTGTAAACGTTAATATT
TTGTTAAAATTCGCGTTAAATTTTTGTTAAATCAGCTCATTTTTTAACCAATAGGCCGAAATCG
GCAAAATCCCTTATAAATCAAAAGAATAGCCCGAGATAGGGTTGAGTGTTGTTCCAGTTTGGAA
CAAGAGTCCACTATTAAAGAACGTGGACTCCAACGTCAAAGGGCGAAAAACCGTCTATCAGGGC
GATGGCCCACTACGTGAACCATCACCCAAATCAAGTTTTTTGGGGTCGAGGTGCCGTAAAGCAC
TAAATCGGAACCCTAAAGGGAGCCCCCGATTTAGAGCTTGACGGGGAAAGCCGGCGAACGTGGC
GAGAAAGGAAGGGAAGAAAGCGAAAGGAGCGGGCGCTAGGGCGCTGGCAAGTGTAGCGGTCACG
CTGCGCGTAACCACCACACCCGCCGCGCTTAATGCGCCGCTACAGGGCGCGTACTATGGTTGCT
TTGACGTATGCGGTGTGAAATACCGCACAGATGCGTAAGGAGAAAATACCGCATCAGGCGCCAT
TCGCCATTCAGGCTGCGCAACTGTTGGGAAGGGCGATCGGTGCGGGCCTCTTCGCTATTACGCC
AGCTGGCGAAAGGGGGATGTGCTGCAAGGCGATTAAGTTGGGTAACGCCAGGGTTTTCCCAGTC
ACGACGTTGTAAAACGACGGCCAGTGCCCAAGCTTACTAGTACTTCTCGAGCTCTGTACATGTC
CGGTCGCGACGTACGCGTATCGATGGCGCCAGCTGCAGGCGGCCGC
```

FIG. 3D

(SEQ ID NO: 11)

SVDDFISTETPIALNNLLCNVGPDGCRAFGTSAGAVIASPSTIDPDYYYMWTRDSALVFKNLID
RFTETYDAGLQRRIEQYITAQVTLQGLSNPSGSLADGSGLGEPKFELTLKPFTGNWGRPQRDGP
ALRAIALIGYSKWLINNNYQSTVSNVIWPIVRNDLNYVAQYWNQTGFDLWEEVNGSSFFTVANQ
HRALVEGATLAATLGQSGSAYSSVAPQVLCFLQRFWVSSGGYVDSNINTNEGRTGKDVNSVLTS
IHTFDPNLGCDAGTFQPCSDKALSNLKVVVDSFRSIYGVNKGIPAGAAVAIGRYAEDVYYNGNP
WYLATFAAAEQLYDAIYVWKKTGSITVTATSLAFFQELVPGVTAGTYSSSSSTFTNIINAVSTY
ADGFLSEAAKYVPADGSLAEQFDRNSGTPLSALHLTWSYASFLTATARRAGIVPPSWANSSAST
IPSTCSGASVVGSYSRPTATSFPPSQTPKPGVPSGTPYTPLPCATPTSVAVTFHELVSTQFGQT
VKVAGNAAALGNWSTSAAVALDAVNYADNHPLWIGTVNLEAGDVVEYKYINVGQDGSVTWESDP
NHTYTVPAVACVTQVVKEDTWQS

FIG. 12

(SEQ ID NO: 12)

AAVDTFINTEKPIAWNKLLANIGPNGKAAPGAAAGVVIASPSRTDPPYFFTWTRDAALVLTGII
ESLGHNYNTTLQTVIQNYVASQAKLQQVSNPSGTFADGSGLGEAKFNVDLTAFTGEWGRPQRDG
PPLRAIALIQYAKWLIANGYKSTAKSVVWPVVKNDLAYTAQYWNETGFDLWEEVPGSSFFTIAS
SHRALTEGAYLAAQLDTECRACTTVAPQVLCFQQAFWNSKGNYVVSNINGGEYRSGKDANSILA
SIHNFDPEAGCDNLTFQPCSERALANHKAYVDSFRNLYAINKGIAQGKAVAVGRYSEDVYYNGN
PWYLANFAAAEQLYDAIYVWNKQGSITVTSVSLPFFRDLVSSVSTGTYSKSSSTFTNIVNAVKA
YADGFIEVAAKYTPSNGALAEQYDRNTGKPDSAADLTWSYSAFLSAIDRRAGLVPPSWRASVAK
SQLPSTCSRIEVAGTYVAATSTSFPSKQTPNPSAAPSPSPYPTACADASEVYVTFNERVSTAWG
ETIKVVGNVPALGNWDTSKAVTLSASGYKSNDPLWSITVPIKATGSAVQYKYIKVGTNGKITWE
SDPNRSITLQTASSAGKCAAQTVNDSWR

FIG. 13

(SEQ ID NO: 13)

ATLDSWLSNEATVARTAILNNIGADGAWVSGADSGIVVASPSTDNPDYFYTWTRDSGLVIKTLV
DLFRNGDTDLLSTIEHYISSQAIIQGVSNPSGDLSSGGLGEPKFNVDETAYTGSWGRPQRDGPA
LRATAMIGFGQWLLDNGYTSAATEIVWPLVRNDLSYVAQYWNQTGYDLWEEVNGSSFFTIAVQH
RALVEGSAFATAVGSSCSWCDSQAPQILCYLQSFWTGSYILANFDSSRSGKDTNTLLGSIHTFD
PEAGCDDSTFQPCSPRALANHKEVVDSFRSIYTLNDGLSDSEAVAVGRYPEDSYYNGNPWFLCT
LAAAEQLYDALYQWDKQGSLEITDVSLDFFKALYSGAATGTYSSSSSTYSSIVSAVKTFADGFV
SIVETHAASNGSLSEQFDKSDGDELSARDLTWSYAALLTANNRRNSVVPPSWGETSASSVPGTC
AATSASGTYSSVTVTSWPSIVATGGTTTTATTTGSGGVTSTSKTTTTASKTSTTTSSTSCTTPT
AVAVTFDLTATTTYGENIYLVGSISQLGDWETSDGIALSADKYTSSNPLWYVTVTLPAGESFEY
KFIRVESDDSVEWESDPNREYTVPQACGESTATVTDTWR

FIG. 14

SEQUENCE LISTING

<160> NUMBER OF SEQ ID NOS: 13

<210> SEQ ID NO 1
<211> LENGTH: 2361
<212> TYPE: DNA
<213> ORGANISM: Aspergillus kawachi

<400> SEQUENCE: 1

```
atgagagtgt cgacttcaag tattgccctt gctgtgtccc tttttgggaa gctggcc ctt        60 gggctgtcag ctgcagaatg gcgcactcaa tccatctact tcctttt gac ggatcggttc       120 ggtaggacgg acaattcgac tacagctacg tgcaatacgg gtgaccaagt atggtattgc       180
tgtacttccg tcattcatct gctgacttgg atagatctac tgtggtggaa gttggcaagg       240
aattatcaac catgttcgta tctcacttca taccatccat gctgggcgct tctgactatt       300
gctccagctg gactatatcc agggcatggg attcacagct atctggatct cgcctatcac       360
tgagcagcta ccccaggata cttcggatgg tgaagcctac catggatact ggcagcagaa       420
gatgtatgcc ctcattgcat tcatatttta tgcttactcg cagactgcag ctgacttggc       480
agatacaatg tgaactccaa cttcggcacg gcagatgatc tgaagtccct ctccgatgct       540
cttcacgccc gcggaatgta cctcatggtc gacgtcgtcc taaccacat ggtaagtact       600 gctttacctc tatattagta aacccaatgc gaacaatgac tgtatcaggg ctacgcaggt       660
aacggcaacg atgtggatta cagcgtcttc gacccctt cg actcctcctc ctacttccat       720
ccatactgcc tcatcacaga ttgggacaac ttgaccatgg tccaagactg ttgggagggt       780
gacaccatcg tgtctctgcc agatctgaac accacggaaa ccgccgtgag aaccatttgg       840
tacgattggg tagccgacct ggtatccaac tactcaggtg cgaccccaac ccactaaaac       900
aagccacata ctaaaaaatt gctcagtcga cggcctccgt atcgacagtg tcgaagaagt       960
cgaacccgac ttcttcccgg gctaccaaga agcagcagga gtctactgcg tcggtgaagt      1020
cgacaacggc aaccctgctc tcgactgccc ataccaaaaa tatctagatg gtgttctcaa      1080
ctatcccatg tacataccccc cttctacctt ctcgaaccca tcactaactc aattgctgca      1140
```

```
gctactggca actcctctac gcctttgaat cctccagcgg cagcatcagc aacctctaca    1200
acatgatcaa atccgtcgcc agcgactgct ccgatccgac cctcctgggc aactttatcg    1260
aaaaccacga caaccccgc ttcgcctcgt atgtcccttc catcactgcc ccctttaaa     1320 gtaaacccca ctgacaggca agctacaca tccgactact cccaagccaa aaacgtcctc    1380
agctacatct tcctctccga cggcatcccc atcgtctacg ccggcgaaga acagcactac    1440
tccggcggcg acgtgcccta caccgcgaa gctacctggc tatcaggcta cgacacctcc    1500
gcggagctct acacctggat agccaccaca aacgcgatcc ggaaactagc tatctcagca    1560
gactcggact acattactta cgcggtttgc ccttccctt cccccaccc agagctcaac    1620 ccccattcta acaaaatatt tcaatggtag aacgacccaa tctacacaga cagcaacacc    1680
atcgcgatgc gcaaaggcac ctccggctcc caaatcatca ccgtcctctc caacaaaggc    1740
tcctccggaa gcagctacac cctcacccctc agcggaagcg gctacacgtc cggcacgaag    1800
ctcatcgaag cgtacacctg cacgtccgtg acggtggact cgaacgggga tatccctgtg    1860
ccgatggctt cggggattacc tagagttctc ctccctgctt cggtggttga tagttcttcg    1920
ctttgtgggg ggagtggtaa cacaaccacg accacaactg ctgctacctc cacatccaaa    1980
gccaccacct cctcttcttc ttcttctgct gctgctacta cttcttcatc atgcaccgca    2040
acaagcacca ccctccccat caccttcgaa gaactcgtca ccactaccta cggggaagaa    2100
gtctacctca gcggatctat ctcccagctc ggagagtggg atacgagtga cgcggtgaag    2160
ttgtccgcgg atgattatac ctcgagtaac cccgagtggt ctgttactgt gtcgttgccg    2220
gtggggacga ccttcgagta taagtttatt aaggtcgatg agggtggaag tgtgacttgg    2280
gaaagtgatc cgaatagga gtatactgtg cctgaatgtg ggagtgggag tggggagacg    2340
gtggttgata cgtggaggta g                                              2361
```

<210> SEQ ID NO 2
<211> LENGTH: 21
<212> TYPE: PRT
<213> ORGANISM: Aspergillus kawachi

<400> SEQUENCE: 2

```
Met Arg Val Ser Thr Ser Ser Ile Ala Leu Ala Val Ser Leu Phe Gly
1               5                   10                  15

Lys Leu Ala Leu Gly
            20
```

<210> SEQ ID NO 3
<211> LENGTH: 619
<212> TYPE: PRT
<213> ORGANISM: Aspergillus kawachi

<400> SEQUENCE: 3

```
Leu Ser Ala Ala Glu Trp Arg Thr Gln Ser Ile Tyr Phe Leu Leu Thr
1               5                   10                  15

Asp Arg Phe Gly Arg Thr Asp Asn Ser Thr Thr Ala Thr Cys Asn Thr
                20                  25                  30

Gly Asp Gln Ile Tyr Cys Gly Gly Ser Trp Gln Gly Ile Ile Asn His
            35                  40                  45

Leu Asp Tyr Ile Gln Gly Met Gly Phe Thr Ala Ile Trp Ile Ser Pro
        50                  55                  60

Ile Thr Glu Gln Leu Pro Gln Asp Thr Ser Asp Gly Glu Ala Tyr His
65                  70                  75                  80
```

```
Gly Tyr Trp Gln Gln Lys Ile Tyr Asn Val Asn Ser Asn Phe Gly Thr
                 85                  90                  95
Ala Asp Asp Leu Lys Ser Leu Ser Asp Ala Leu His Ala Arg Gly Met
            100                 105                 110
Tyr Leu Met Val Asp Val Val Pro Asn His Met Gly Tyr Ala Gly Asn
        115                 120                 125
Gly Asn Asp Val Asp Tyr Ser Val Phe Asp Pro Phe Asp Ser Ser Ser
    130                 135                 140
Tyr Phe His Pro Tyr Cys Leu Ile Thr Asp Trp Asp Asn Leu Thr Met
145                 150                 155                 160
Val Gln Asp Cys Trp Glu Gly Asp Thr Ile Val Ser Leu Pro Asp Leu
                165                 170                 175
Asn Thr Thr Glu Thr Ala Val Arg Thr Ile Trp Tyr Asp Trp Val Ala
            180                 185                 190
Asp Leu Val Ser Asn Tyr Ser Val Asp Gly Leu Arg Ile Asp Ser Val
        195                 200                 205
Glu Glu Val Glu Pro Asp Phe Phe Pro Gly Tyr Gln Glu Ala Ala Gly
    210                 215                 220
Val Tyr Cys Val Gly Glu Val Asp Asn Gly Asn Pro Ala Leu Asp Cys
225                 230                 235                 240
Pro Tyr Gln Lys Tyr Leu Asp Gly Val Leu Asn Tyr Pro Ile Tyr Trp
                245                 250                 255
Gln Leu Leu Tyr Ala Phe Glu Ser Ser Gly Ser Ile Ser Asn Leu
            260                 265                 270
Tyr Asn Met Ile Lys Ser Val Ala Ser Asp Cys Ser Asp Pro Thr Leu
        275                 280                 285
Leu Gly Asn Phe Ile Glu Asn His Asp Asn Pro Arg Phe Ala Ser Tyr
    290                 295                 300
Thr Ser Asp Tyr Ser Gln Ala Lys Asn Val Leu Ser Tyr Ile Phe Leu
305                 310                 315                 320
Ser Asp Gly Ile Pro Ile Val Tyr Ala Gly Glu Gln His Tyr Ser
                325                 330                 335
Gly Gly Asp Val Pro Tyr Asn Arg Glu Ala Thr Trp Leu Ser Gly Tyr
            340                 345                 350
Asp Thr Ser Ala Glu Leu Tyr Thr Trp Ile Ala Thr Asn Ala Ile
        355                 360                 365
Arg Lys Leu Ala Ile Ser Ala Asp Ser Asp Tyr Ile Thr Tyr Ala Asn
    370                 375                 380
Asp Pro Ile Tyr Thr Asp Ser Asn Thr Ile Ala Met Arg Lys Gly Thr
385                 390                 395                 400
Ser Gly Ser Gln Ile Ile Thr Val Leu Ser Asn Lys Gly Ser Ser Gly
                405                 410                 415
Ser Ser Tyr Thr Leu Thr Leu Ser Gly Ser Gly Tyr Thr Ser Gly Thr
            420                 425                 430
Lys Leu Ile Glu Ala Tyr Thr Cys Thr Ser Val Thr Val Asp Ser Asn
        435                 440                 445
Gly Asp Ile Pro Val Pro Met Ala Ser Gly Leu Pro Arg Val Leu Leu
    450                 455                 460
Pro Ala Ser Val Val Asp Ser Ser Leu Cys Gly Gly Ser Gly Asn
465                 470                 475                 480
Thr Thr Thr Thr Thr Thr Ala Ala Thr Thr Ser Lys Ala Thr Thr
                485                 490                 495
Ser Ser Ser Ser Ser Ser Ala Ala Ala Thr Thr Ser Ser Ser Cys Thr
```

-continued

```
            500                 505                 510
Ala Thr Ser Thr Thr Leu Pro Ile Thr Phe Glu Glu Leu Val Thr Thr
        515                 520                 525

Thr Tyr Gly Glu Glu Val Tyr Leu Ser Gly Ser Ile Ser Gln Leu Gly
    530                 535                 540

Glu Trp Asp Thr Ser Asp Ala Val Lys Leu Ser Ala Asp Asp Tyr Thr
545                 550                 555                 560

Ser Ser Asn Pro Glu Trp Ser Val Thr Val Ser Leu Pro Val Gly Thr
                565                 570                 575

Thr Phe Glu Tyr Lys Phe Ile Lys Val Asp Glu Gly Gly Ser Val Thr
            580                 585                 590

Trp Glu Ser Asp Pro Asn Arg Glu Tyr Thr Val Pro Glu Cys Gly Ser
        595                 600                 605

Gly Ser Gly Glu Thr Val Val Asp Thr Trp Arg
    610                 615

<210> SEQ ID NO 4
<211> LENGTH: 640
<212> TYPE: PRT
<213> ORGANISM: Aspergillus kawachi

<400> SEQUENCE: 4

Met Arg Val Ser Thr Ser Ser Ile Ala Leu Ala Val Ser Leu Phe Gly
1               5                   10                  15

Lys Leu Ala Leu Gly Leu Ser Ala Ala Glu Trp Arg Thr Gln Ser Ile
            20                  25                  30

Tyr Phe Leu Leu Thr Asp Arg Phe Gly Arg Thr Asp Asn Ser Thr Thr
        35                  40                  45

Ala Thr Cys Asn Thr Gly Asp Gln Ile Tyr Cys Gly Gly Ser Trp Gln
    50                  55                  60

Gly Ile Ile Asn His Leu Asp Tyr Ile Gln Gly Met Gly Phe Thr Ala
65                  70                  75                  80

Ile Trp Ile Ser Pro Ile Thr Glu Gln Leu Pro Gln Asp Thr Ser Asp
                85                  90                  95

Gly Glu Ala Tyr His Gly Tyr Trp Gln Gln Lys Ile Tyr Asn Val Asn
            100                 105                 110

Ser Asn Phe Gly Thr Ala Asp Asp Leu Lys Ser Leu Ser Asp Ala Leu
        115                 120                 125

His Ala Arg Gly Met Tyr Leu Met Val Asp Val Val Pro Asn His Met
    130                 135                 140

Gly Tyr Ala Gly Asn Gly Asn Asp Val Asp Tyr Ser Val Phe Asp Pro
145                 150                 155                 160

Phe Asp Ser Ser Ser Tyr Phe His Pro Tyr Cys Leu Ile Thr Asp Trp
                165                 170                 175

Asp Asn Leu Thr Met Val Gln Asp Cys Trp Glu Gly Asp Thr Ile Val
            180                 185                 190

Ser Leu Pro Asp Leu Asn Thr Thr Glu Thr Ala Val Arg Thr Ile Trp
        195                 200                 205

Tyr Asp Trp Val Ala Asp Leu Val Ser Asn Tyr Ser Val Asp Gly Leu
    210                 215                 220

Arg Ile Asp Ser Val Glu Glu Val Glu Pro Asp Phe Phe Pro Gly Tyr
225                 230                 235                 240

Gln Glu Ala Ala Gly Val Tyr Cys Val Gly Glu Val Asp Asn Gly Asn
                245                 250                 255
```

-continued

Pro Ala Leu Asp Cys Pro Tyr Gln Lys Tyr Leu Asp Gly Val Leu Asn
        260                 265                 270

Tyr Pro Ile Tyr Trp Gln Leu Leu Tyr Ala Phe Glu Ser Ser Ser Gly
        275                 280                 285

Ser Ile Ser Asn Leu Tyr Asn Met Ile Lys Ser Val Ala Ser Asp Cys
        290                 295                 300

Ser Asp Pro Thr Leu Leu Gly Asn Phe Ile Glu Asn His Asp Asn Pro
305                 310                 315                 320

Arg Phe Ala Ser Tyr Thr Ser Asp Tyr Ser Gln Ala Lys Asn Val Leu
                325                 330                 335

Ser Tyr Ile Phe Leu Ser Asp Gly Ile Pro Ile Val Tyr Ala Gly Glu
                340                 345                 350

Glu Gln His Tyr Ser Gly Gly Asp Val Pro Tyr Asn Arg Glu Ala Thr
            355                 360                 365

Trp Leu Ser Gly Tyr Asp Thr Ser Ala Glu Leu Tyr Thr Trp Ile Ala
        370                 375                 380

Thr Thr Asn Ala Ile Arg Lys Leu Ala Ile Ser Ala Asp Ser Asp Tyr
385                 390                 395                 400

Ile Thr Tyr Ala Asn Asp Pro Ile Tyr Thr Asp Ser Asn Thr Ile Ala
                405                 410                 415

Met Arg Lys Gly Thr Ser Gly Ser Gln Ile Ile Thr Val Leu Ser Asn
                420                 425                 430

Lys Gly Ser Ser Gly Ser Ser Tyr Thr Leu Thr Leu Ser Gly Ser Gly
            435                 440                 445

Tyr Thr Ser Gly Thr Lys Leu Ile Glu Ala Tyr Thr Cys Thr Ser Val
        450                 455                 460

Thr Val Asp Ser Asn Gly Asp Ile Pro Val Pro Met Ala Ser Gly Leu
465                 470                 475                 480

Pro Arg Val Leu Leu Pro Ala Ser Val Val Asp Ser Ser Ser Leu Cys
                485                 490                 495

Gly Gly Ser Gly Asn Thr Thr Thr Thr Thr Ala Ala Thr Ser Thr
            500                 505                 510

Ser Lys Ala Thr Thr Ser Ser Ser Ser Ser Ala Ala Thr Thr
        515                 520                 525

Ser Ser Ser Cys Thr Ala Thr Ser Thr Thr Leu Pro Ile Thr Phe Glu
        530                 535                 540

Glu Leu Val Thr Thr Thr Tyr Gly Glu Glu Val Tyr Leu Ser Gly Ser
545                 550                 555                 560

Ile Ser Gln Leu Gly Glu Trp Asp Thr Ser Asp Ala Val Lys Leu Ser
                565                 570                 575

Ala Asp Asp Tyr Thr Ser Ser Asn Pro Glu Trp Ser Val Thr Val Ser
                580                 585                 590

Leu Pro Val Gly Thr Thr Phe Glu Tyr Lys Phe Ile Lys Val Asp Glu
            595                 600                 605

Gly Gly Ser Val Thr Trp Glu Ser Asp Pro Asn Arg Glu Tyr Thr Val
        610                 615                 620

Pro Glu Cys Gly Ser Gly Ser Gly Glu Thr Val Val Asp Thr Trp Arg
625                 630                 635                 640

<210> SEQ ID NO 5
<211> LENGTH: 10990
<212> TYPE: DNA
<213> ORGANISM: Artificial Sequence
<220> FEATURE:
<223> OTHER INFORMATION: pTrex3g_Akalpha plasmid

<400> SEQUENCE: 5

```
ctgcagccac ttgcagtccc gtggaattct cacggtgaat gtaggccttt tgtagggtag     60
gaattgtcac tcaagcaccc ccaacctcca ttacgcctcc cccatagagt tcccaatcag    120
tgagtcatgg cactgttctc aaatagattg gggagaagtt gacttccgcc cagagctgaa    180
ggtcgcacaa ccgcatgata tagggtcggc aacggcaaaa aagcacgtgg ctcaccgaaa    240
agcaagatgt ttgcgatcta acatccagga acctggatac atccatcatc acgcacgacc    300
actttgatct gctggtaaac tcgtattcgc cctaaaccga agtgcgtggt aaatctacac    360
gtgggcccct ttcggtatac tgcgtgtgtc ttctctaggt gccattcttt tcccttcctc    420
tagtgttgaa ttgtttgtgt tggagtccga gctgtaacta cctctgaatc tctggagaat    480
ggtggactaa cgactaccgt gcacctgcat catgtatata atagtgatcc tgagaagggg    540
ggtttggagc aatgtgggac tttgatggtc atcaaacaaa gaacgaagac gcctcttttg    600
caaagttttg tttcggctac ggtgaagaac tggatacttg ttgtgtcttc tgtgtatttt    660
tgtggcaaca agaggccaga gacaatctat tcaaacacca agcttgctct tttgagctac    720
aagaacctgt ggggtatata tctagagttg tgaagtcggt aatcccgctg tatagtaata    780
cgagtcgcat ctaaatactc cgaagctgct gcgaacccgg agaatcgaga tgtgctggaa    840
agcttctagc gagcggctaa attagcatga aaggctatga gaaattctgg agacggcttg    900
ttgaatcatg gcgttccatt cttcgacaag caaagcgttc cgtcgcagta gcaggcactc    960
attcccgaaa aaactcggag attcctaagt agcgatggaa ccggaataat ataataggca   1020
atacattgag ttgcctcgac ggttgcaatg caggggtact gagcttggac ataactgttc   1080
cgtaccccac ctcttctcaa cctttggcgt ttccctgatt cagcgtaccc gtacaagtcg   1140
taatcactat taacccagac tgaccggacg tgttttgccc ttcatttgga gaaataatgt   1200
cattgcgatg tgtaatttgc ctgcttgacc gactggggct gttcgaagcc cgaatgtagg   1260
attgttatcc gaactctgct cgtagaggca tgttgtgaat ctgtgtcggg caggacacgc   1320
ctcgaaggtt cacggcaagg gaaaccaccg atagcagtgt ctagtagcaa cctgtaaagc   1380
cgcaatgcag catcactgga aaatacaaac caatggctaa aagtacataa gttaatgcct   1440
aaagaagtca tataccagcg gctaataatt gtacaatcaa gtggctaaac gtaccgtaat   1500
ttgccaacgg cttgtggggt tgcagaagca acggcaaagc cccacttccc cacgtttgtt   1560
tcttcactca gtccaatctc agctggtgat cccccaattg ggtcgcttgt ttgttccggt   1620
gaagtgaaag aagacagagg taagaatgtc tgactcggag cgttttgcat acaaccaagg   1680
gcagtgatgg aagacagtga aatgttgaca ttcaaggagt atttagccag ggatgcttga   1740
gtgtatcgtg taaggaggtt tgtctgccga tacgacgaat actgtatagt cacttctgat   1800
gaagtggtcc atattgaaat gtaagtcggc actgaacagg caaaagattg agttgaaact   1860
gcctaagatc tcgggccctc gggccttcgg cctttgggtg tacatgtttg tgctccgggc   1920
aaatgcaaag tgtggtagga tcgaacacac tgctgccttt accaagcagc tgagggtatg   1980
tgataggcaa atgttcaggg gccactgcat ggtttcgaat agaaagagaa gcttagccaa   2040
gaacaatagc cgataaagat agcctcatta aacggaatga gctagtaggc aaagtcagcg   2100
aatgtgtata tataaaggtt cgaggtccgt gcctccctca tgctctcccc atctactcat   2160
caactcagat cctccaggag acttgtacac catcttttga ggcacagaaa cccaatagtc   2220
aaccatcaca gtttgtaca aaaaagcagg ctccgcggcc gccccttca ccatgagagt    2280
```

```
gtcgacttca agtattgccc ttgctgtgtc ccttttgg aagctggccc ttgggctgtc    2340
agctgcagaa tggcgcactc aatccatcta cttccttttg acggatcggt tcggtaggac    2400
ggacaattcg actacagcta cgtgcaatac gggtgaccaa gtatggtatt gctgtacttc    2460
cgtcattcat ctgctgactt ggatagatct actgtggtgg aagttggcaa ggaattatca    2520
accatgttcg tatctcactt cataccatcc atgctgggcg cttctgacta ttgctccagc    2580
tggactatat ccagggcatg ggattcacag ctatctggat ctcgcctatc actgagcagc    2640
taccccagga tacttcggat ggtgaagcct accatggata ctggcagcag aagatgtatg    2700
ccctcattgc attcatattt tatgcttact cgcagactgc agctgacttg cagatacaa    2760
tgtgaactcc aacttcggca cggcagatga tctgaagtcc ctctccgatg ctcttcacgc    2820
ccgcggaatg tacctcatgg tcgacgtcgt ccctaaccac atggtaagta ctgctttacc    2880
tctatattag taaacccaat gcgaacaatg actgtatcag gctacgcag gtaacggcaa    2940
cgatgtggat tacagcgtct tcgaccccatt cgactcctcc tcctacttcc atccatactg    3000
cctcatcaca gattgggaca acttgaccat ggtccaagac tgttgggagg gtgacaccat    3060
cgtgtctctg ccagatctga acaccacgga accgccgtg agaaccattt ggtacgattg    3120
ggtagccgac ctggtatcca actactcagg tgcgacccca acccactaaa acaagccaca    3180
tactaaaaaa ttgctcagtc gacggcctcc gtatcgacga tgtcgaagaa gtcgacccg    3240
acttcttccc gggctaccaa gaagcagcag gagtctactg cgtcggtgaa gtcgacaacg    3300
gcaaccctgc tctcgactgc ccataccaaa aatatctaga tggtgttctc aactatccca    3360
tgtacatacc cccttctacc ttctcgaacc catcactaac tcaattgctg cagctactgg    3420
caactcctct acgcctttga atcctccagc ggcagcatca gcaacctcta caacatgatc    3480
aaatccgtcg ccagcgactg ctccgatccg accctcctgg gcaactttat cgaaaaccac    3540
gacaaccccc gcttcgcctc gtatgtccct tccatcactg ccccctttta agtaaaccc    3600
cactgacagg caaagctaca catccgacta ctcccaagcc aaaaacgtcc tcagctacat    3660
cttcctctcc gacggcatcc ccatcgtcta cgccggcgaa gaacagcact actccgcgg    3720
cgacgtgccc tacaaccgcg aagctacctg gctatcaggc tacgacacct ccgcggagct    3780
ctacacctgg atagccacca caaacgcgat ccggaaacta gctatctcag cagactcgga    3840
ctacattact tacgcggttt gcccctttccc ttcccccac ccagagctca ccccattc    3900
taacaaaata tttcaatggt agaacgaccc aatctacaca gacagcaaca ccatcgcgat    3960
gcgcaaaggc acctccggct cccaaatcat caccgtcctc tccaacaaag gctcctccgg    4020
aagcagctac accctcaccc tcagcggaag cggctacacg tccggcacga agctcatcga    4080
agcgtacacc tgcacgtccg tgacggtgga ctcgaacggg gatatccctg tgccgatggc    4140
ttcgggatta cctagagttc tcctccctgc ttcggtggtt gatagttctt cgctttgtgg    4200
ggggagtggt aacacaacca cgaccacaac tgctgctacc tccacatcca agccaccac    4260
ctcctcttct tcttcttctg ctgctgctac tacttcttca tcatgcaccg caacaagcac    4320
cacctcccc atcaccttcg aagaactcgt caccactacc tacggggaag aagtctacct    4380
cagcggatct atctcccagc tcggagagtg ggatacgagt gacgcggtga agttgtccgc    4440
ggatgattat acctcgagta accccgagtg gtctgttact gtgtcgttgc cggtggggac    4500
gaccttcgag tataagttta ttaaggtcga tgagggtgga agtgtgactt gggaaagtga    4560
tccgaatagg gagtatactg tgcctgaatg tgggagtggg agtggggaga cggtggttga    4620
tacgtggagg tagaagggtg ggcgcgccga cccagctttc ttgtacaaag tggtgatcgc    4680
```

```
gccagctccg tgcgaaagcc tgacgcaccg gtagattctt ggtgagcccg tatcatgacg   4740
gcggcgggag ctacatggcc ccgggtgatt tatttttttt gtatctactt ctgacccttt   4800
tcaaatatac ggtcaactca tctttcactg gagatgcggc ctgcttggta ttgcgatgtt   4860
gtcagcttgg caaattgtgg ctttcgaaaa cacaaaacga ttccttagta gccatgcatt   4920
ttaagataac ggaatagaag aaagaggaaa ttaaaaaaaa aaaaaaaaca aacatcccgt   4980
tcataacccg tagaatcgcc gctcttcgtg tatcccagta ccagtttatt ttgaatagct   5040
cgcccgctgg agagcatcct gaatgcaagt aacaaccgta gaggctgaca cggcaggtgt   5100
tgctagggag cgtcgtgttc tacaaggcca gacgtcttcg cggttgatat atatgtatgt   5160
ttgactgcag gctgctcagc gacgacagtc aagttcgccc tcgctgcttg tgcaataatc   5220
gcagtgggga agccacaccg tgactcccat ctttcagtaa agctctgttg gtgtttatca   5280
gcaatacacg taatttaaac tcgttagcat ggggctgata gcttaattac cgtttaccag   5340
tgccatggtt ctgcagcttt ccttggcccg taaaattcgg cgaagccagc caatcaccag   5400
ctaggcacca gctaaaccct ataattagtc tcttatcaac accatccgct cccccgggat   5460
caatgaggag aatgaggggg atgcggggct aaagaagcct acataaccct catgccaact   5520
cccagtttac actcgtcgag ccaacatcct gactataagc taacacagaa tgcctcaatc   5580
ctgggaagaa ctggccgctg ataagcgcgc ccgcctcgca aaaaccatcc ctgatgaatg   5640
gaaagtccag acgctgcctg cggaagacag cgttattgat ttcccaaaga aatcggggat   5700
cctttcagag gccgaactga agatcacaga ggcctccgct gcagatcttg tgtccaagct   5760
ggcggccgga gagttgacct cggtggaagt tacgctagca ttctgtaaac gggcagcaat   5820
cgcccagcag ttagtagggt cccctctacc tctcaggag atgtaacaac gccaccttat   5880
gggactatca agctgacgct ggcttctgtg cagacaaact gcgcccacga gttcttccct   5940
gacgccgctc tcgcgcaggc aagggaactc gatgaatact acgcaaagca caagagaccc   6000
gttggtccac tccatggcct ccccatctct ctcaaagacc agcttcgagt caaggtacac   6060
cgttgcccct aagtcgttag atgtcccttt ttgtcagcta acatatgcca ccagggctac   6120
gaaacatcaa tgggctacat ctcatggcta aacaagtacg acgaagggga ctcggttctg   6180
acaaccatgc tccgcaaagc cggtgccgtc ttctacgtca agacctctgt cccgcagacc   6240
ctgatggtct gcgagacagt caacaacatc atcgggcgca ccgtcaaccc acgcaacaag   6300
aactggtcgt gcgcggcag ttctggtggt gagggtgcga tcgttgggat tcgtggtggc   6360
gtcatcggtg taggaacgga tatcggtggc tcgattcgag tgccggccgc gttcaacttc   6420
ctgtacggtc taaggccgag tcatgggcgg ctgccgtatg caaagatggc gaacagcatg   6480
gagggtcagg agacggtgca cagcgttgtc gggccgatta cgcactctgt tgagggtgag   6540
tccttcgcct cttccttctt ttcctgctct ataccaggcc tccactgtcc tcctttcttg   6600 cttttatac tatatacgag accggcagtc actgatgaag tatgttagac ctccgcctct   6660
tcaccaaatc cgtcctcggt caggagccat ggaaatacga ctccaaggtc atccccatgc   6720
cctggcgcca gtccgagtcg acattattg cctccaagat caagaacggc gggctcaata   6780
tcggctacta caacttcgac ggcaatgtcc ttccacaccc tcctatcctg cgcggcgtgg   6840
aaaccaccgt cgccgcactc gccaaagccg gtcacaccgt gaccccgtgg acgccataca   6900
agcacgattt cggccacgat ctcatctccc atatctacgc ggctgacggc agcgccgacg   6960
taatgcgcga tatcagtgca tccggcgagc cggcgattcc aaatatcaaa gacctactga   7020
```

```
acccgaacat caaagctgtt aacatgaacg agctctggga cacgcatctc cagaagtgga   7080
attaccagat ggagtacctt gagaaatggc gggaggctga agaaaaggcc gggaaggaac   7140
tggacgccat catcgcgccg attacgccta ccgctgcggt acggcatgac cagttccggt   7200
actatgggta tgcctctgtg atcaacctgc tggatttcac gagcgtggtt gttccggtta   7260
cctttgcgga taagaacatc gataagaaga atgagagttt caaggcggtt agtgagcttg   7320
atgccctcgt gcaggaagag tatgatccgg aggcgtacca tggggcaccg gttgcagtgc   7380
aggttatcgg acggagactc agtgaagaga ggacgttggc gattgcagag gaagtgggga   7440
agttgctggg aaatgtggtg actccatagc taataagtgt cagatagcaa tttgcacaag   7500
aaatcaatac cagcaactgt aaataagcgc tgaagtgacc atgccatgct acgaaagagc   7560
agaaaaaaac ctgccgtaga accgaagaga tatgacacgc ttccatctct caaggaaga   7620 atcccttcag ggttgcgttt ccagtctaga cacgtataac ggcacaagtg tctctcacca   7680
aatgggttat atctcaaatg tgatctaagg atggaaagcc cagaatatcg atcgcgcgca   7740
gatccatata tagggcccgg gttataatta cctcaggtcg acgtcccatg gccattcgaa   7800
ttcgtaatca tggtcatagc tgtttcctgt gtgaaattgt tatccgctca caattccaca   7860
caacatacga gccggaagca taaagtgtaa agcctggggt gcctaatgag tgagctaact   7920
cacattaatt gcgttgcgct cactgcccgc tttccagtcg ggaaacctgt cgtgccagct   7980
gcattaatga atcggccaac gcgcggggag aggcggtttg cgtattgggc gctcttccgc   8040
ttcctcgctc actgactcgc tgcgctcggt cgttcggctg cggcgagcgg tatcagctca   8100
ctcaaaggcg gtaatacggt tatccacaga atcagggga acgcaggaa agaacatgtg   8160 agcaaaaggc cagcaaaagg ccaggaaccg taaaaaggcc gcgttgctgg cgttttttcca   8220 taggctccgc ccccctgacg agcatcacaa aaatcgacgc tcaagtcaga ggtggcgaaa   8280
cccgacagga ctataaagat accaggcgtt tcccctgga agctccctcg tgcgctctcc   8340
tgttccgacc ctgccgctta ccggatacct gtccgccttt ctcccttcgg gaagcgtggc   8400
gctttctcat agctcacgct gtaggtatct cagttcggtg taggtcgttc gctccaagct   8460
gggctgtgtg cacgaacccc ccgttcagcc cgaccgctgc gccttatccg gtaactatcg   8520
tcttgagtcc aacccggtaa gacacgactt atcgccactg gcagcagcca ctggtaacag   8580
gattagcaga gcgaggtatg taggcggtgc tacagagttc ttgaagtggt ggcctaacta   8640
cggctacact agaagaacag tatttggtat ctgcgctctg ctgaagccag ttaccttcgg   8700
aaaaagagtt ggtagctctt gatccggcaa acaaaccacc gctggtagcg gtggtttttt   8760
tgtttgcaag cagcagatta cgcgcagaaa aaaaggatct caagaagatc ctttgatctt   8820
ttctacgggg tctgacgctc agtggaacga aaactcacgt taagggattt tggtcatgag   8880
attatcaaaa aggatcttca cctagatcct tttaaattaa aaatgaagtt ttaaatcaat   8940
ctaaagtata tatgagtaaa cttggtctga cagttaccaa tgcttaatca gtgaggcacc   9000
tatctcagcg atctgtctat ttcgttcatc catagttgcc tgactccccg tcgtgtagat   9060
aactacgata cgggagggct taccatctgg ccccagtgct gcaatgatac cgcgagaccc   9120
acgctcaccg gctccagatt tatcagcaat aaaccagcca gccggaaggg ccgagcgcag   9180
aagtggtcct gcaactttat ccgcctccat ccagtctatt aattgttgcc gggaagctag   9240
agtaagtagt tcgccagtta atagtttgcg caacgttgtt gccattgcta caggcatcgt   9300
ggtgtcacgc tcgtcgtttg gtatggcttc attcagctcc ggttcccaac gatcaaggcg   9360
agttacatga tcccccatgt tgtgcaaaaa agcggttagc tccttcggtc ctccgatcgt   9420
```

-continued

```
tgtcagaagt aagttggccg cagtgttatc actcatggtt atggcagcac tgcataattc    9480
tcttactgtc atgccatccg taagatgctt ttctgtgact ggtgagtact caaccaagtc    9540
attctgagaa tagtgtatgc ggcgaccgag ttgctcttgc ccggcgtcaa tacgggataa    9600
taccgcgcca catagcagaa ctttaaaagt gctcatcatt ggaaaacgtt cttcggggcg    9660
aaaactctca aggatcttac cgctgttgag atccagttcg atgtaaccca ctcgtgcacc    9720
caactgatct tcagcatctt ttactttcac cagcgtttct gggtgagcaa aacaggaag     9780
gcaaaatgcc gcaaaaaagg gaataagggc gacacgaaaa tgttgaatac tcatactctt    9840
ccttttcaa tattattgaa gcatttatca gggttattgt ctcatgagcg gatacatatt     9900
tgaatgtatt tagaaaaata acaaataggg gttccgcgc acatttcccc gaaaagtgcc     9960
acctgacgtc taagaaacca ttattatcat gacattaacc tataaaaata ggcgtatcac   10020
gaggcccttt cgtctcgcgc gtttcggtga tgacggtgaa aacctctgac acatgcagct   10080
cccggagacg gtcacagctt gtctgtaagc ggatgccggg agcagacaag cccgtcaggg   10140
cgcgtcagcg ggtgttggcg ggtgtcgggg ctggcttaac tatgcggcat cagagcagat   10200
tgtactgaga gtgcaccata aaattgtaaa cgttaatatt ttgttaaaat tcgcgttaaa   10260
ttttttgttaa atcagctcat tttttaacca ataggccgaa atcggcaaaa tcccttataa   10320
atcaaaagaa tagcccgaga taggggttgag tgttgttcca gtttggaaca agagtccact   10380
attaaagaac gtggactcca acgtcaaagg gcgaaaaacc gtctatcagg gcgatggccc   10440
actacgtgaa ccatcaccca aatcaagttt tttggggtcg aggtgccgta aagcactaaa   10500
tcggaacccct aaagggagcc cccgatttag agcttgacgg ggaaagccgg cgaacgtggc   10560
gagaaaggaa gggaagaaag cgaaaggagc gggcgctagg gcgctggcaa gtgtagcggt   10620
cacgctgcgc gtaaccacca cacccgccgc gcttaatgcg ccgctacagg gcgcgtacta   10680
tggttgcttt gacgtatgcg gtgtgaaata ccgcacagat gcgtaaggag aaaataccgc   10740
atcaggcgcc attcgccatt caggctgcgc aactgttggg aagggcgatc ggtgcgggcc   10800
tcttcgctat tacgccagct ggcgaaaggg ggatgtgctg caaggcgatt aagttgggta   10860
acgccagggt tttcccagtc acgacgttgt aaaacgacgg ccagtgccca agcttactag   10920
tacttctcga gctctgtaca tgtccggtcg cgacgtacgc gtatcgatgg cgccagctgc   10980
aggcggccgc                                                          10990
```

```
<210> SEQ ID NO 6
<211> LENGTH: 24
<212> TYPE: DNA
<213> ORGANISM: Artificial Sequence
<220> FEATURE:
<223> OTHER INFORMATION: primer

<400> SEQUENCE: 6
caccatgaga gtgtcgactt caag                                            24

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
ctacctccac gtatcaacca c                                               21
```

```
<210> SEQ ID NO 8
<211> LENGTH: 37
<212> TYPE: PRT
<213> ORGANISM: Aspergillus kawachi

<400> SEQUENCE: 8

Thr Thr Thr Thr Thr Thr Ala Ala Thr Ser Thr Ser Lys Ala Thr Thr
1               5                   10                  15

Ser Ser Ser Ser Ser Ser Ala Ala Ala Thr Thr Ser Ser Ser Cys Thr
            20                  25                  30

Ala Thr Ser Thr Thr
        35

<210> SEQ ID NO 9
<211> LENGTH: 480
<212> TYPE: PRT
<213> ORGANISM: Aspergillus kawachi

<400> SEQUENCE: 9

Leu Ser Ala Ala Glu Trp Arg Thr Gln Ser Ile Tyr Phe Leu Leu Thr
1               5                   10                  15

Asp Arg Phe Gly Arg Thr Asp Asn Ser Thr Thr Ala Thr Cys Asn Thr
            20                  25                  30

Gly Asp Gln Ile Tyr Cys Gly Gly Ser Trp Gln Gly Ile Ile Asn His
        35                  40                  45

Leu Asp Tyr Ile Gln Gly Met Gly Phe Thr Ala Ile Trp Ile Ser Pro
50                  55                  60

Ile Thr Glu Gln Leu Pro Gln Asp Thr Ser Asp Gly Glu Ala Tyr His
65                  70                  75                  80

Gly Tyr Trp Gln Gln Lys Ile Tyr Asn Val Asn Ser Asn Phe Gly Thr
                85                  90                  95

Ala Asp Asp Leu Lys Ser Leu Ser Asp Ala Leu His Ala Arg Gly Met
            100                 105                 110

Tyr Leu Met Val Asp Val Val Pro Asn His Met Gly Tyr Ala Gly Asn
        115                 120                 125

Gly Asn Asp Val Asp Tyr Ser Val Phe Asp Pro Phe Asp Ser Ser Ser
130                 135                 140

Tyr Phe His Pro Tyr Cys Leu Ile Thr Asp Trp Asp Asn Leu Thr Met
145                 150                 155                 160

Val Gln Asp Cys Trp Glu Gly Asp Thr Ile Val Ser Leu Pro Asp Leu
                165                 170                 175

Asn Thr Thr Glu Thr Ala Val Arg Thr Ile Trp Tyr Asp Trp Val Ala
            180                 185                 190

Asp Leu Val Ser Asn Tyr Ser Val Asp Gly Leu Arg Ile Asp Ser Val
        195                 200                 205

Glu Glu Val Glu Pro Asp Phe Phe Pro Gly Tyr Gln Glu Ala Ala Gly
210                 215                 220

Val Tyr Cys Val Gly Glu Val Asp Asn Gly Asn Pro Ala Leu Asp Cys
225                 230                 235                 240

Pro Tyr Gln Lys Tyr Leu Asp Gly Val Leu Asn Tyr Pro Ile Tyr Trp
                245                 250                 255

Gln Leu Leu Tyr Ala Phe Glu Ser Ser Ser Gly Ser Ile Ser Asn Leu
            260                 265                 270

Tyr Asn Met Ile Lys Ser Val Ala Ser Asp Cys Ser Asp Pro Thr Leu
        275                 280                 285
```

Leu Gly Asn Phe Ile Glu Asn His Asp Asn Pro Arg Phe Ala Ser Tyr
            290                 295                 300

Thr Ser Asp Tyr Ser Gln Ala Lys Asn Val Leu Ser Tyr Ile Phe Leu
305                 310                 315                 320

Ser Asp Gly Ile Pro Ile Val Tyr Ala Gly Glu Glu Gln His Tyr Ser
                325                 330                 335

Gly Gly Asp Val Pro Tyr Asn Arg Glu Ala Thr Trp Leu Ser Gly Tyr
            340                 345                 350

Asp Thr Ser Ala Glu Leu Tyr Thr Trp Ile Ala Thr Asn Ala Ile
        355                 360                 365

Arg Lys Leu Ala Ile Ser Ala Asp Ser Asp Tyr Ile Thr Tyr Ala Asn
        370                 375                 380

Asp Pro Ile Tyr Thr Asp Ser Asn Thr Ile Ala Met Arg Lys Gly Thr
385                 390                 395                 400

Ser Gly Ser Gln Ile Ile Thr Val Leu Ser Asn Lys Gly Ser Ser Gly
                405                 410                 415

Ser Ser Tyr Thr Leu Thr Leu Ser Gly Ser Gly Tyr Thr Ser Gly Thr
            420                 425                 430

Lys Leu Ile Glu Ala Tyr Thr Cys Thr Ser Val Thr Val Asp Ser Asn
        435                 440                 445

Gly Asp Ile Pro Val Pro Met Ala Ser Gly Leu Pro Arg Val Leu Leu
450                 455                 460

Pro Ala Ser Val Val Asp Ser Ser Ser Leu Cys Gly Gly Ser Gly Asn
465                 470                 475                 480

<210> SEQ ID NO 10
<211> LENGTH: 102
<212> TYPE: PRT
<213> ORGANISM: Aspergillus kawachi

<400> SEQUENCE: 10

Leu Pro Ile Thr Phe Glu Glu Leu Val Thr Thr Thr Tyr Gly Glu Glu
1               5                   10                  15

Val Tyr Leu Ser Gly Ser Ile Ser Gln Leu Gly Glu Trp Asp Thr Ser
            20                  25                  30

Asp Ala Val Lys Leu Ser Ala Asp Asp Tyr Thr Ser Ser Asn Pro Glu
        35                  40                  45

Trp Ser Val Thr Val Ser Leu Pro Val Gly Thr Thr Phe Glu Tyr Lys
    50                  55                  60

Phe Ile Lys Val Asp Glu Gly Gly Ser Val Thr Trp Glu Ser Asp Pro
65                  70                  75                  80

Asn Arg Glu Tyr Thr Val Pro Glu Cys Gly Ser Gly Ser Gly Glu Thr
                85                  90                  95

Val Val Asp Thr Trp Arg
            100

<210> SEQ ID NO 11
<211> LENGTH: 599
<212> TYPE: PRT
<213> ORGANISM: Artificial Sequence
<220> FEATURE:
<223> OTHER INFORMATION: glucoamylase derived from Trichoderma reesei

<400> SEQUENCE: 11

Ser Val Asp Asp Phe Ile Ser Thr Glu Thr Pro Ile Ala Leu Asn Asn
1               5                   10                  15

Leu Leu Cys Asn Val Gly Pro Asp Gly Cys Arg Ala Phe Gly Thr Ser

-continued

```
                20                  25                  30
Ala Gly Ala Val Ile Ala Ser Pro Ser Thr Ile Asp Pro Asp Tyr Tyr
            35                  40                  45
Tyr Met Trp Thr Arg Asp Ser Ala Leu Val Phe Lys Asn Leu Ile Asp
    50                  55                  60
Arg Phe Thr Glu Thr Tyr Asp Ala Gly Leu Gln Arg Arg Ile Glu Gln
65                  70                  75                  80
Tyr Ile Thr Ala Gln Val Thr Leu Gln Gly Leu Ser Asn Pro Ser Gly
                85                  90                  95
Ser Leu Ala Asp Gly Ser Gly Leu Gly Glu Pro Lys Phe Glu Leu Thr
            100                 105                 110
Leu Lys Pro Phe Thr Gly Asn Trp Gly Arg Pro Gln Arg Asp Gly Pro
        115                 120                 125
Ala Leu Arg Ala Ile Ala Leu Ile Gly Tyr Ser Lys Trp Leu Ile Asn
    130                 135                 140
Asn Asn Tyr Gln Ser Thr Val Ser Asn Val Ile Trp Pro Ile Val Arg
145                 150                 155                 160
Asn Asp Leu Asn Tyr Val Ala Gln Tyr Trp Asn Gln Thr Gly Phe Asp
                165                 170                 175
Leu Trp Glu Glu Val Asn Gly Ser Ser Phe Phe Thr Val Ala Asn Gln
            180                 185                 190
His Arg Ala Leu Val Glu Gly Ala Thr Leu Ala Ala Thr Leu Gly Gln
        195                 200                 205
Ser Gly Ser Ala Tyr Ser Ser Val Ala Pro Gln Val Leu Cys Phe Leu
    210                 215                 220
Gln Arg Phe Trp Val Ser Ser Gly Gly Tyr Val Asp Ser Asn Ile Asn
225                 230                 235                 240
Thr Asn Glu Gly Arg Thr Gly Lys Asp Val Asn Ser Val Leu Thr Ser
                245                 250                 255
Ile His Thr Phe Asp Pro Asn Leu Gly Cys Asp Ala Gly Thr Phe Gln
            260                 265                 270
Pro Cys Ser Asp Lys Ala Leu Ser Asn Leu Lys Val Val Val Asp Ser
        275                 280                 285
Phe Arg Ser Ile Tyr Gly Val Asn Lys Gly Ile Pro Ala Gly Ala Ala
    290                 295                 300
Val Ala Ile Gly Arg Tyr Ala Glu Asp Val Tyr Tyr Asn Gly Asn Pro
305                 310                 315                 320
Trp Tyr Leu Ala Thr Phe Ala Ala Ala Glu Gln Leu Tyr Asp Ala Ile
                325                 330                 335
Tyr Val Trp Lys Lys Thr Gly Ser Ile Thr Val Thr Ala Thr Ser Leu
            340                 345                 350
Ala Phe Phe Gln Glu Leu Val Pro Gly Val Thr Ala Gly Thr Tyr Ser
        355                 360                 365
Ser Ser Ser Ser Thr Phe Thr Asn Ile Ile Asn Ala Val Ser Thr Tyr
    370                 375                 380
Ala Asp Gly Phe Leu Ser Glu Ala Ala Lys Tyr Val Pro Ala Asp Gly
385                 390                 395                 400
Ser Leu Ala Glu Gln Phe Asp Arg Asn Ser Gly Thr Pro Leu Ser Ala
                405                 410                 415
Leu His Leu Thr Trp Ser Tyr Ala Ser Phe Leu Thr Ala Thr Ala Arg
            420                 425                 430
Arg Ala Gly Ile Val Pro Pro Ser Trp Ala Asn Ser Ser Ala Ser Thr
        435                 440                 445
```

```
Ile Pro Ser Thr Cys Ser Gly Ala Ser Val Val Gly Ser Tyr Ser Arg
    450                 455                 460

Pro Thr Ala Thr Ser Phe Pro Pro Ser Gln Thr Pro Lys Pro Gly Val
465                 470                 475                 480

Pro Ser Gly Thr Pro Tyr Thr Pro Leu Pro Cys Ala Thr Pro Thr Ser
                485                 490                 495

Val Ala Val Thr Phe His Glu Leu Val Ser Thr Gln Phe Gly Gln Thr
                500                 505                 510

Val Lys Val Ala Gly Asn Ala Ala Leu Gly Asn Trp Ser Thr Ser
            515                 520                 525

Ala Ala Val Ala Leu Asp Ala Val Asn Tyr Ala Asp Asn His Pro Leu
            530                 535                 540

Trp Ile Gly Thr Val Asn Leu Glu Ala Gly Asp Val Val Glu Tyr Lys
545                 550                 555                 560

Tyr Ile Asn Val Gly Gln Asp Gly Ser Val Thr Trp Glu Ser Asp Pro
                565                 570                 575

Asn His Thr Tyr Thr Val Pro Ala Val Ala Cys Val Thr Gln Val Val
                580                 585                 590

Lys Glu Asp Thr Trp Gln Ser
            595
```

<210> SEQ ID NO 12
<211> LENGTH: 604
<212> TYPE: PRT
<213> ORGANISM: Artificial Sequence
<220> FEATURE:
<223> OTHER INFORMATION: glucoamylase derived from Humicola grisea

<400> SEQUENCE: 12

```
Ala Ala Val Asp Thr Phe Ile Asn Thr Glu Lys Pro Ile Ala Trp Asn
1               5                   10                  15

Lys Leu Leu Ala Asn Ile Gly Pro Asn Gly Lys Ala Ala Pro Gly Ala
            20                  25                  30

Ala Ala Gly Val Val Ile Ala Ser Pro Ser Arg Thr Asp Pro Pro Tyr
        35                  40                  45

Phe Phe Thr Trp Thr Arg Asp Ala Ala Leu Val Leu Thr Gly Ile Ile
    50                  55                  60

Glu Ser Leu Gly His Asn Tyr Asn Thr Thr Leu Gln Thr Val Ile Gln
65              70                  75                  80

Asn Tyr Val Ala Ser Gln Ala Lys Leu Gln Gln Val Ser Asn Pro Ser
                85                  90                  95

Gly Thr Phe Ala Asp Gly Ser Gly Leu Gly Glu Ala Lys Phe Asn Val
            100                 105                 110

Asp Leu Thr Ala Phe Thr Gly Glu Trp Gly Arg Pro Gln Arg Asp Gly
        115                 120                 125

Pro Pro Leu Arg Ala Ile Ala Leu Ile Gln Tyr Ala Lys Trp Leu Ile
    130                 135                 140

Ala Asn Gly Tyr Lys Ser Thr Ala Lys Ser Val Val Trp Pro Val Val
145                 150                 155                 160

Lys Asn Asp Leu Ala Tyr Thr Ala Gln Tyr Trp Asn Glu Thr Gly Phe
                165                 170                 175

Asp Leu Trp Glu Glu Val Pro Gly Ser Ser Phe Phe Thr Ile Ala Ser
            180                 185                 190

Ser His Arg Ala Leu Thr Glu Gly Ala Tyr Leu Ala Ala Gln Leu Asp
        195                 200                 205
```

```
Thr Glu Cys Arg Ala Cys Thr Thr Val Ala Pro Gln Val Leu Cys Phe
    210                 215                 220

Gln Gln Ala Phe Trp Asn Ser Lys Gly Asn Tyr Val Ser Asn Ile
225                 230                 235                 240

Asn Gly Gly Glu Tyr Arg Ser Gly Lys Asp Ala Asn Ser Ile Leu Ala
                245                 250                 255

Ser Ile His Asn Phe Asp Pro Glu Ala Gly Cys Asp Asn Leu Thr Phe
            260                 265                 270

Gln Pro Cys Ser Glu Arg Ala Leu Ala Asn His Lys Ala Tyr Val Asp
        275                 280                 285

Ser Phe Arg Asn Leu Tyr Ala Ile Asn Lys Gly Ile Ala Gln Gly Lys
    290                 295                 300

Ala Val Ala Val Gly Arg Tyr Ser Glu Asp Val Tyr Asn Gly Asn
305                 310                 315                 320

Pro Trp Tyr Leu Ala Asn Phe Ala Ala Glu Gln Leu Tyr Asp Ala
                325                 330                 335

Ile Tyr Val Trp Asn Lys Gln Gly Ser Ile Thr Val Thr Ser Val Ser
            340                 345                 350

Leu Pro Phe Phe Arg Asp Leu Val Ser Ser Val Ser Thr Gly Thr Tyr
        355                 360                 365

Ser Lys Ser Ser Ser Thr Phe Thr Asn Ile Val Asn Ala Val Lys Ala
    370                 375                 380

Tyr Ala Asp Gly Phe Ile Glu Val Ala Ala Lys Tyr Thr Pro Ser Asn
385                 390                 395                 400

Gly Ala Leu Ala Glu Gln Tyr Asp Arg Asn Thr Gly Lys Pro Asp Ser
                405                 410                 415

Ala Ala Asp Leu Thr Trp Ser Tyr Ser Ala Phe Leu Ser Ala Ile Asp
            420                 425                 430

Arg Arg Ala Gly Leu Val Pro Pro Ser Trp Arg Ala Ser Val Ala Lys
        435                 440                 445

Ser Gln Leu Pro Ser Thr Cys Ser Arg Ile Glu Val Ala Gly Thr Tyr
    450                 455                 460

Val Ala Ala Thr Ser Thr Ser Phe Pro Ser Lys Gln Thr Pro Asn Pro
465                 470                 475                 480

Ser Ala Ala Pro Ser Pro Ser Tyr Pro Thr Ala Cys Ala Asp Ala
                485                 490                 495

Ser Glu Val Tyr Val Thr Phe Asn Glu Arg Val Ser Thr Ala Trp Gly
            500                 505                 510

Glu Thr Ile Lys Val Val Gly Asn Val Pro Ala Leu Gly Asn Trp Asp
        515                 520                 525

Thr Ser Lys Ala Val Thr Leu Ser Ala Ser Gly Tyr Lys Ser Asn Asp
    530                 535                 540

Pro Leu Trp Ser Ile Thr Val Pro Ile Lys Ala Thr Gly Ser Ala Val
545                 550                 555                 560

Gln Tyr Lys Tyr Ile Lys Val Gly Thr Asn Gly Lys Ile Thr Trp Glu
                565                 570                 575

Ser Asp Pro Asn Arg Ser Ile Thr Leu Gln Thr Ala Ser Ser Ala Gly
            580                 585                 590

Lys Cys Ala Ala Gln Thr Val Asn Asp Ser Trp Arg
        595                 600

<210> SEQ ID NO 13
<211> LENGTH: 615
```

```
<212> TYPE: PRT
<213> ORGANISM: Artificial Sequence
<220> FEATURE:
<223> OTHER INFORMATION: glucoamylase derived from Aspergillus awamori

<400> SEQUENCE: 13
```

| | | | | | | | | | | | | | | |
|---|---|---|---|---|---|---|---|---|---|---|---|---|---|---|
| Ala | Thr | Leu | Asp | Ser | Trp | Leu | Ser | Asn | Glu | Ala | Thr | Val | Ala | Arg | Thr |
| 1 | | | | 5 | | | | | 10 | | | | | 15 |
| Ala | Ile | Leu | Asn | Asn | Ile | Gly | Ala | Asp | Gly | Ala | Trp | Val | Ser | Gly | Ala |
| | | | | 20 | | | | | 25 | | | | | 30 | |
| Asp | Ser | Gly | Ile | Val | Val | Ala | Ser | Pro | Ser | Thr | Asp | Asn | Pro | Asp | Tyr |
| | | | 35 | | | | | 40 | | | | | 45 | | |
| Phe | Tyr | Thr | Trp | Thr | Arg | Asp | Ser | Gly | Leu | Val | Ile | Lys | Thr | Leu | Val |
| | 50 | | | | | 55 | | | | | 60 | | | | |
| Asp | Leu | Phe | Arg | Asn | Gly | Asp | Thr | Asp | Leu | Leu | Ser | Thr | Ile | Glu | His |
| 65 | | | | | 70 | | | | | 75 | | | | | 80 |
| Tyr | Ile | Ser | Ser | Gln | Ala | Ile | Ile | Gln | Gly | Val | Ser | Asn | Pro | Ser | Gly |
| | | | | 85 | | | | | 90 | | | | | 95 | |
| Asp | Leu | Ser | Ser | Gly | Gly | Leu | Gly | Glu | Pro | Lys | Phe | Asn | Val | Asp | Glu |
| | | | 100 | | | | | 105 | | | | | 110 | | |
| Thr | Ala | Tyr | Thr | Gly | Ser | Trp | Gly | Arg | Pro | Gln | Arg | Asp | Gly | Pro | Ala |
| | | | 115 | | | | | 120 | | | | | 125 | | |
| Leu | Arg | Ala | Thr | Ala | Met | Ile | Gly | Phe | Gly | Gln | Trp | Leu | Leu | Asp | Asn |
| | 130 | | | | | 135 | | | | | 140 | | | | |
| Gly | Tyr | Thr | Ser | Ala | Ala | Thr | Glu | Ile | Val | Trp | Pro | Leu | Val | Arg | Asn |
| 145 | | | | | 150 | | | | | 155 | | | | | 160 |
| Asp | Leu | Ser | Tyr | Val | Ala | Gln | Tyr | Trp | Asn | Gln | Thr | Gly | Tyr | Asp | Leu |
| | | | | 165 | | | | | 170 | | | | | 175 | |
| Trp | Glu | Glu | Val | Asn | Gly | Ser | Ser | Phe | Phe | Thr | Ile | Ala | Val | Gln | His |
| | | | 180 | | | | | 185 | | | | | 190 | | |
| Arg | Ala | Leu | Val | Glu | Gly | Ser | Ala | Phe | Ala | Thr | Ala | Val | Gly | Ser | Ser |
| | | | 195 | | | | | 200 | | | | | 205 | | |
| Cys | Ser | Trp | Cys | Asp | Ser | Gln | Ala | Pro | Gln | Ile | Leu | Cys | Tyr | Leu | Gln |
| | 210 | | | | | 215 | | | | | 220 | | | | |
| Ser | Phe | Trp | Thr | Gly | Ser | Tyr | Ile | Leu | Ala | Asn | Phe | Asp | Ser | Ser | Arg |
| 225 | | | | | 230 | | | | | 235 | | | | | 240 |
| Ser | Gly | Lys | Asp | Thr | Asn | Thr | Leu | Leu | Gly | Ser | Ile | His | Thr | Phe | Asp |
| | | | | 245 | | | | | 250 | | | | | 255 | |
| Pro | Glu | Ala | Gly | Cys | Asp | Asp | Ser | Thr | Phe | Gln | Pro | Cys | Ser | Pro | Arg |
| | | | 260 | | | | | 265 | | | | | 270 | | |
| Ala | Leu | Ala | Asn | His | Lys | Glu | Val | Val | Asp | Ser | Phe | Arg | Ser | Ile | Tyr |
| | | | 275 | | | | | 280 | | | | | 285 | | |
| Thr | Leu | Asn | Asp | Gly | Leu | Ser | Asp | Ser | Glu | Ala | Val | Ala | Val | Gly | Arg |
| | 290 | | | | | 295 | | | | | 300 | | | | |
| Tyr | Pro | Glu | Asp | Ser | Tyr | Tyr | Asn | Gly | Asn | Pro | Trp | Phe | Leu | Cys | Thr |
| 305 | | | | | 310 | | | | | 315 | | | | | 320 |
| Leu | Ala | Ala | Ala | Glu | Gln | Leu | Tyr | Asp | Ala | Leu | Tyr | Gln | Trp | Asp | Lys |
| | | | | 325 | | | | | 330 | | | | | 335 | |
| Gln | Gly | Ser | Leu | Glu | Ile | Thr | Asp | Val | Ser | Leu | Asp | Phe | Phe | Lys | Ala |
| | | | 340 | | | | | 345 | | | | | 350 | | |
| Leu | Tyr | Ser | Gly | Ala | Ala | Thr | Gly | Thr | Tyr | Ser | Ser | Ser | Ser | Ser | Thr |
| | | | 355 | | | | | 360 | | | | | 365 | | |
| Tyr | Ser | Ser | Ile | Val | Ser | Ala | Val | Lys | Thr | Phe | Ala | Asp | Gly | Phe | Val |
| | 370 | | | | | 375 | | | | | 380 | | | | |

-continued

```
Ser Ile Val Glu Thr His Ala Ala Ser Asn Gly Ser Leu Ser Glu Gln
385                 390                 395                 400

Phe Asp Lys Ser Asp Gly Asp Glu Leu Ser Ala Arg Asp Leu Thr Trp
                405                 410                 415

Ser Tyr Ala Ala Leu Leu Thr Ala Asn Asn Arg Arg Asn Ser Val Val
            420                 425                 430

Pro Pro Ser Trp Gly Glu Thr Ser Ala Ser Ser Val Pro Gly Thr Cys
        435                 440                 445

Ala Ala Thr Ser Ala Ser Gly Thr Tyr Ser Ser Val Thr Val Thr Ser
    450                 455                 460

Trp Pro Ser Ile Val Ala Thr Gly Gly Thr Thr Thr Ala Thr Thr
465             470                 475                 480

Thr Gly Ser Gly Gly Val Thr Ser Thr Ser Lys Thr Thr Thr Thr Ala
                485                 490                 495

Ser Lys Thr Ser Thr Thr Thr Ser Ser Thr Ser Cys Thr Thr Pro Thr
                500                 505                 510

Ala Val Ala Val Thr Phe Asp Leu Thr Ala Thr Thr Thr Tyr Gly Glu
            515                 520                 525

Asn Ile Tyr Leu Val Gly Ser Ile Ser Gln Leu Gly Asp Trp Glu Thr
        530                 535                 540

Ser Asp Gly Ile Ala Leu Ser Ala Asp Lys Tyr Thr Ser Ser Asn Pro
545                 550                 555                 560

Leu Trp Tyr Val Thr Val Thr Leu Pro Ala Gly Glu Ser Phe Glu Tyr
                565                 570                 575

Lys Phe Ile Arg Val Glu Ser Asp Asp Ser Val Glu Trp Glu Ser Asp
                580                 585                 590

Pro Asn Arg Glu Tyr Thr Val Pro Gln Ala Cys Gly Glu Ser Thr Ala
            595                 600                 605

Thr Val Thr Asp Thr Trp Arg
    610                 615
```

ACID-STABLE ALPHA AMYLASES HAVING GRANULAR STARCH HYDROLYZING ACTIVITY AND ENZYME COMPOSITIONS

The present application is a Continuation of U.S. patent application Ser. No. 11/136,244, filed May 24, 2005, now issued U.S. Pat. No. 7,354,752, which claims priority to U.S. Provisional Patent Application Ser. No. 60/575,175, filed May 27, 2004, U.S. Provisional Patent Application Ser. No. 60/605,437, filed Aug. 30, 2004; International Application No. PCT/US04/040040, filed Nov. 30, 2004; International Application No. PCT/US04/041276, filed Dec. 9, 2004; and U.S. Provisional Patent Application Ser. No. 60/647,925 filed Jan. 28, 2005, the contents of each are fully incorporated herein by reference.

FIELD OF THE INVENTION

The present invention relates to an acid-stable alpha amylase (asAA) derived from a strain of *Aspergillus kawachi*, which has granular starch hydrolyzing (GSH) activity. Further, the invention relates to the heterologous expression of an asAA having GSH activity in filamentous fungal host cells and particularly in *Trichoderma* and *Aspergillus* cells and the use of asAA having GSH activity in compositions, which optionally include glucoamylases to enhance starch hydrolysis.

BACKGROUND OF THE INVENTION

Glucoamylases, and particularly glucoamylases having granular starch hydrolyzing (GSH) activity are important industrial enzymes used for producing products such as organic acids (e.g. lactic acids), amino acids (e.g. glutamic acids), sugar sweetener products (e.g. glucose and high fructose corn syrup), alcohols (e.g. ethanol) and other compounds from starch substrates derived from grains and cereals. During microbial fermentations, and particularly during simultaneous saccharification and fermentation (SSF), it would be of benefit to reduce the amount of residual starch in the fermentation when granular starch substrates are used as a carbon feed. The present invention answers this need by providing an acid-stable alpha amylase (asAA) having granular starch hydrolyzing activity, which may be used in combination with a glucoamylase to enhance starch hydrolysis and alcohol production.

Additionally, benefits of the present invention over prior art compositions and methods include one or more of the following: a) a reduction of thermal energy use during starch hydrolysis and end-product production; b) reduction in the requirement of high enzyme dosage; c) utilization of a continuous release of glucose from starch to feed the yeast; d) maintenance of a relatively low glucose level in the fermenter, which significantly reduces the high risk of microbial contamination and removes the catabolite repression of yeast due to high concentration of free glucose; e) reduction in formation of browning reaction products; f) reduction or removal of calcium addition, which was required during the prior art jet cooking process; g) reduction in water utilization during the fermentation process; h) use of higher solids content in the fermentation, which may result in higher end-product formation and reduced energy costs; i) reduced levels of production of certain by-products, such as glycerol; and j) decreased residual starch content and increased protein content of distillers dry grains plus solubles.

SUMMARY OF THE INVENTION

In one aspect, the invention relates to a fungal host cell comprising a heterologous polynucleotide that encodes an acid-stable alpha amylase (asAA) having granular starch hydrolyzing (GSH) activity which has at least 90% sequence identity to the sequence of SEQ ID NO: 3. In some embodiments, the heterologous polynucleotide will encode an asAA having GSH activity with at least 95% sequence identity to the sequence of SEQ ID NO: 3. In some embodiments, the asAA, which is expressed in the fungal host including a heterologous polynucleotide encoding the asAA, will have at least one different property compared to the corresponding asAA produced by the endogenous expression in the native fungal host. In some embodiments, the different property is the pH optimum of the asAA or the pH range for activity. In one embodiment of this aspect, the fungal host cell is a *Trichoderma* cell. In a further embodiment, the *Trichoderma* host cell is a *T. reesei* cell. In another embodiment, the fungal host cell is an *Aspergillus* cell.

In a second aspect, the invention relates to an asAA having GSH activity comprising an amino acid sequence having at least 90% sequence identity with SEQ ID NO: 3. In some embodiments of this aspect, the asAA having GSH activity will be a truncated asAA. In some embodiments, the truncated asAA comprises a sequence of SEQ ID NO: 9 or a sequence having at least 97% sequence identity thereto.

In a third aspect, the invention relates to a granular starch hydrolyzing enzyme composition which comprises an acid-stable alpha amylase (asAA) having granular starch hydrolyzing (GSH) activity, wherein the asAA having GSH activity has at least 90% sequence identity to the sequence of SEQ ID NO: 3. In some embodiments, the granular starch hydrolyzing enzyme composition comprises a truncated asAA enzyme, said enzyme having at least 97% sequence identity with SEQ ID NO: 9. In some embodiments, the asAA will be obtained from the expression of a heterologous polynucleotide in a fungal host cell. In further embodiments, the fungal host cell will be a *Trichoderma* or *Aspergillus* host cell. In other embodiments, the composition will further include a glucoamylase enzyme. In some preferred embodiments, the glucoamylase enzyme will be obtained from a strain of *Aspergillus* or *Rhizopus*. In other embodiments, the glucoamylase will be a glucoamylase having GSH activity and will be obtained from a strain of *Aspergillus, Trichoderma, Rhizopus* or *Humicola*. In other embodiments, both the asAA and the glucoamylase will be expressed in a fungal host having a heterologous polynucleotide which expresses an asAA having GSH activity and a glucoamylase. In some embodiments, the fungal host strain will be the same and in other embodiments, the fungal host strain will be different strains. In other embodiments, the invention relates to a method of hydrolyzing granular starch using the enzyme composition of this aspect.

In a fourth aspect, the invention relates to a method for producing an acid stable alpha amylase (asAA) having granular starch hydrolyzing (GSH) activity in a filamentous fungal host cell comprising transforming a filamentous fungal host cell with a DNA construct including a promoter having transcriptional activity in the filamentous fungal host cell operably linked to a heterologous polynucleotide encoding an asAA having GSH activity and at least 90% sequence identity to SEQ ID NO: 3, cultivating the transformed filamentous fungal host cell in a suitable culture medium to allow expression of said asAA, and producing the asAA. In one embodiment, the method further comprises recovering the produced asAA. In a second embodiment, the fungal host cell is a *Trichoderma* cell and particularly a *T. reesei* cell.

In a fifth aspect, the invention relates to a method of increasing the granular starch hydrolyzing activity of a composition comprising a glucoamylase, which comprises adding an acid-stable alpha amylase (asAA) having granular starch hydrolyzing (GSH) activity to a composition which includes a granular starch substrate and a glucoamylase to produce a soluble starch hydrolysate. In some embodiments, the asAA having GSH activity has an amino acid sequence of at least 90% sequence identity to SEQ ID NO: 3. In other embodiments, the asAA having GSH activity is a truncated asAA. In some embodiments, the truncated asAA includes a sequence having at least 97% sequence identity with SEQ ID NO: 9. In further embodiments, the amount of solubilized starch is greater than a corresponding composition absent the asAA having GSH activity.

BRIEF DESCRIPTION OF THE DRAWINGS

FIG. 1 provides the genomic DNA sequence coding for the native *Aspergillus kawachi* acid-stable alpha-amylase, which is designated asaA (SEQ ID NO:1). The eight putative introns are underlined.

FIG. 2 provides the signal sequence (SEQ ID NO: 2) and mature amino acid sequence (SEQ ID NO: 3) (AsaA) for *A. kawachi* acid stable alpha-amylase (SEQ ID NO: 4). The putative signal sequence (amino acids 1-21) is underlined and bold. The putative linker is TTTTTTAATSTSKATTSSSSS-SAAATTSSSCTATSTT (SEQ ID NO: 8). The amino acids upstream of the linker, which are not underlined comprise the catalytic domain (SEQ ID NO: 9) and the amino acids downstream of the linker comprise the starch binding domain (SBD) (SEQ ID NO: 10). The SBD includes the last 102 amino acids of the polypeptide of FIG. 2.

FIGS. 3A-D provide the complete nucleotide sequence (SEQ ID NO: 5), 10990 bp, of plasmid pTrex3g_Akalpha (FIG. 4).

b. asaA is the *Aspergillus kawachi* polynucleotide encoding the acid stable alpha amylase of SEQ ID NO. 4;

c. cbhI terminator is the *Trichoderma reesei* cellobiohydrolase terminator;

d. amdS is an *Aspergillus nidulans* acetamidase nutritional marker gene; and e. attB is a Gateway cloning system (Invitrogen) lambda phage site for recombination.

Figure 5A:
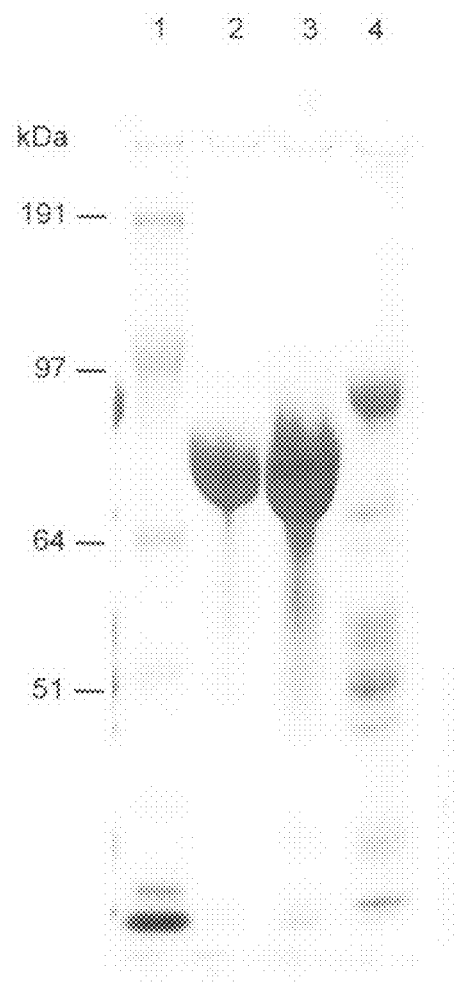
Figure 5B:
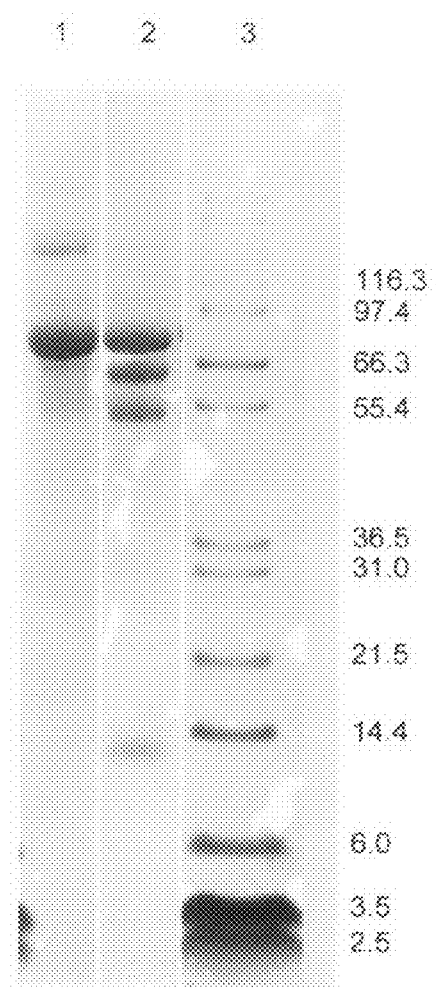

FIGS. 5A and B provide an SDS-PAGE gel indicating the expression of asaA from *Trichoderma reesei* in a representative fermentation run for *Trichoderma reesei* clones as described in Example 5. In FIG. 5A, lane 1 represents the standard See Blue +2 marker; lane 2 represents *T. reesei* expressed AsaA after 80 hours; lane 3 represents *T. reesei* expressed AsaA after 162 hours and lane 4 represents a *T. reesei* host cell control at 162 hours in which the host cell has not been transformed with the asaA. An AsaA protein band is clearly observed at about 90 kDa and this band is absent in the host strain control. In FIG. 5B, lane 1 represents intact *T. reesei* expressed AsaA after 210 hrs, lane 2 represents three bands of *T. reesei* expressed AsaA in intact and truncated form after 200 hours and lane 3 represents a molecular weight marker control.

Figure 6:
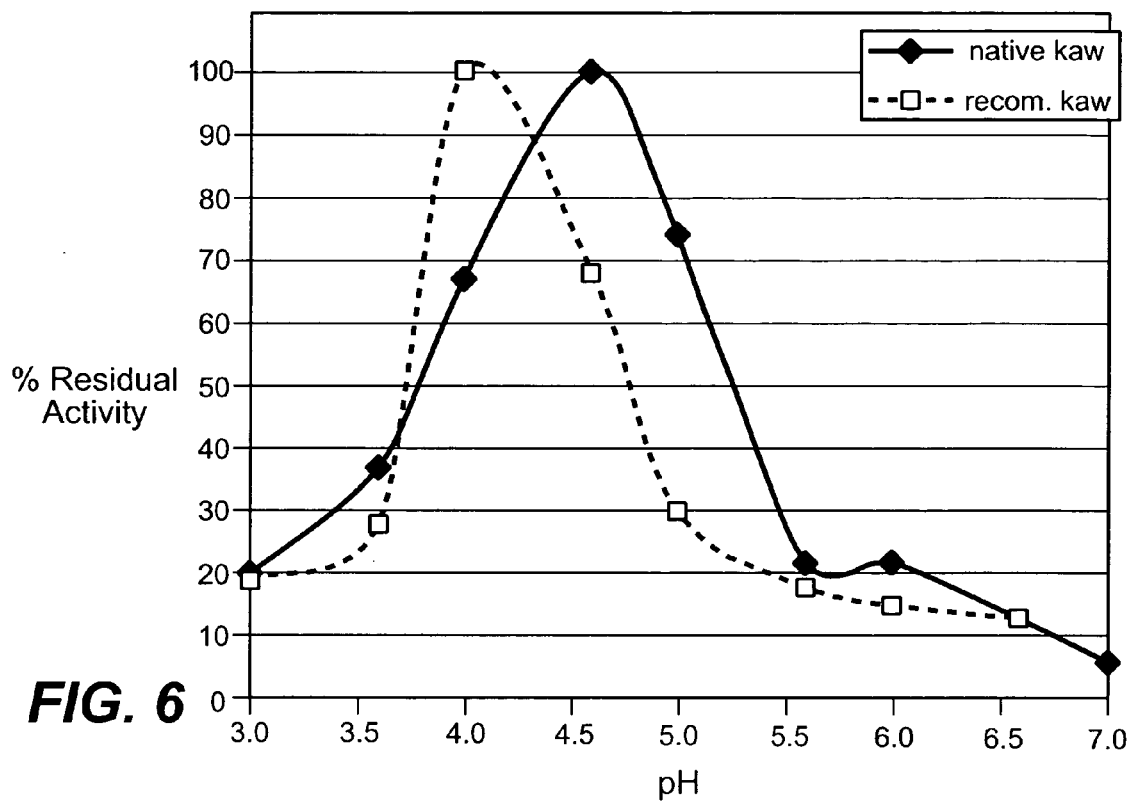

FIG. 6 illustrates the pH stability as % residual activity for the native *Aspergillus kawachi* (nAk-AsaA) and the expressed *A. kawachi* (rAk-AsaA) in the *T. reesei* host (SEQ ID NO:3), as described in Example 6.

Figure 7:
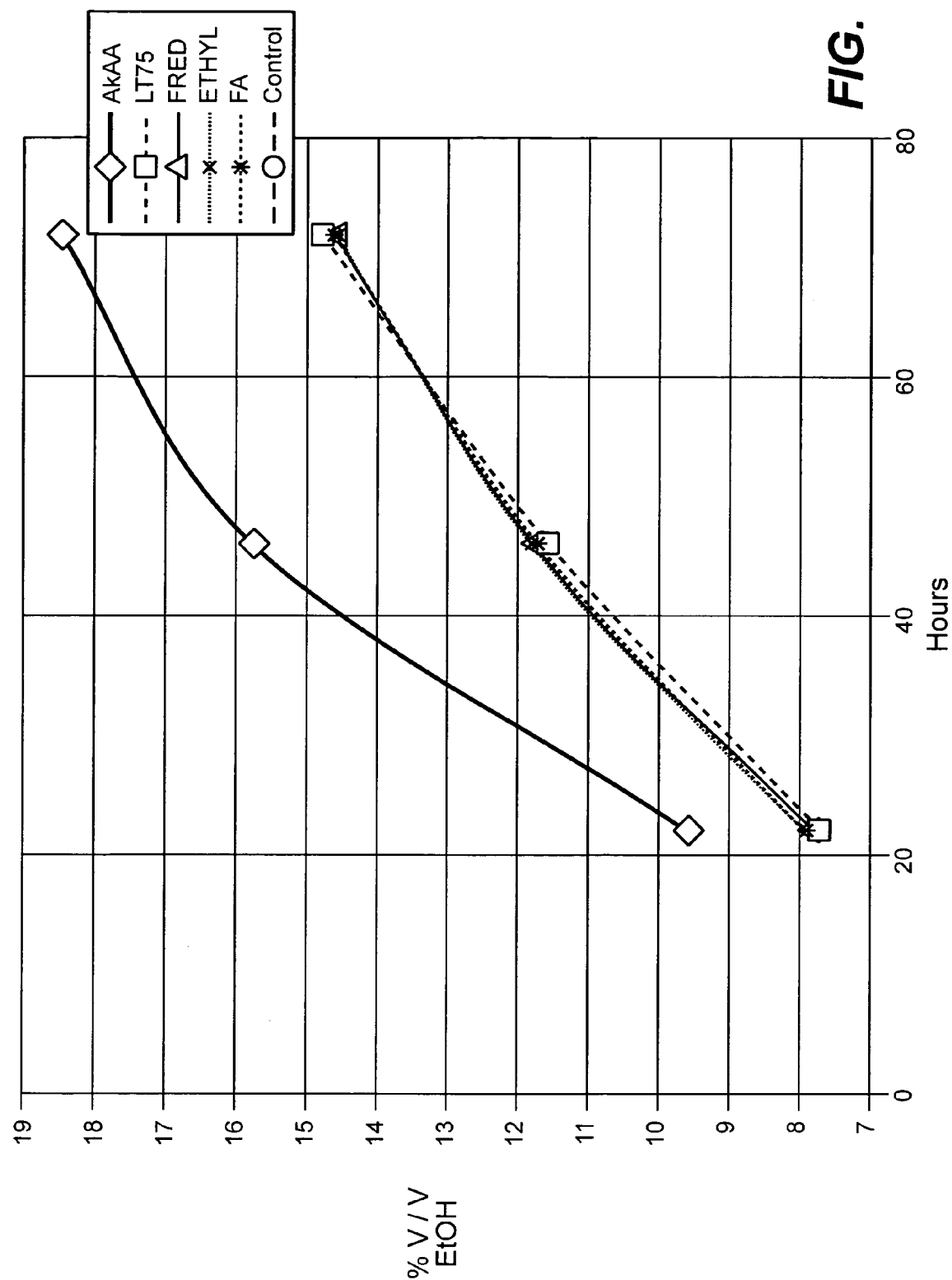

FIG. 7 illustrates the % (v/v) ethanol (EtOH) production from the fermentation of corn flour mash at pH 5.0 with glucoamylase (0.5 GAU/g DISTILLASE) and an alpha amylase over time, wherein Tr-AsaA (*A. kawachi* acid stable alpha amylase expressed in *Trichoderma reesei*) is represented by AkAA; SPEZYME LT75 alpha amylase is represented by LT75; SPEZYME FRED is represented by FRED; SPEZYME ETHYL is represented by ETHYL; CLARASE is represented by FA and DISTILLASE is the control. Reference is made to Example 8.

Figure 8:
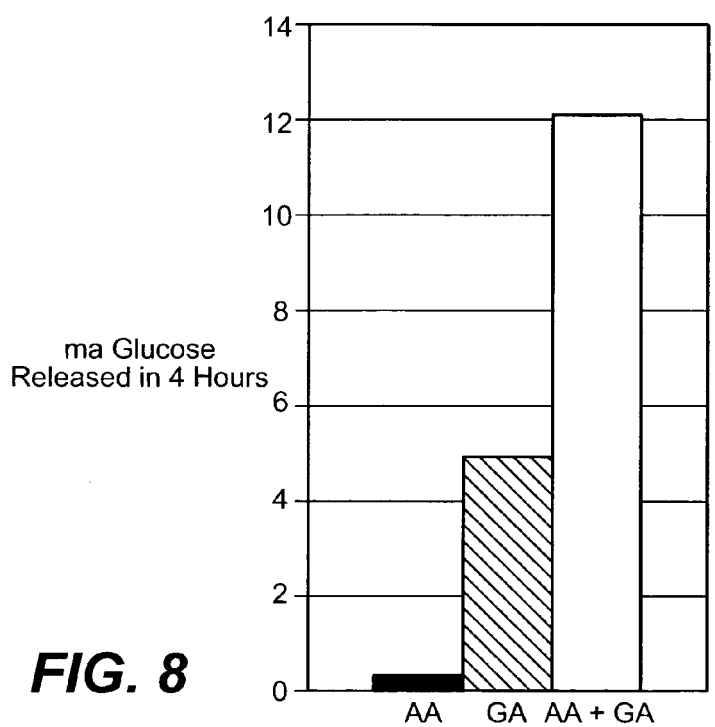

FIG. 8 illustrates the degradation of granular starch as glucose released after 4 hours with incubated purified DISTILLASE (GA), purified AkAA (*A. kawachi* acid stable alpha amylase expressed in *Trichoderma reesei*), and the combination of AkAA and GA at pH 5.0. Reference is made to Example 11.

Figure 9:
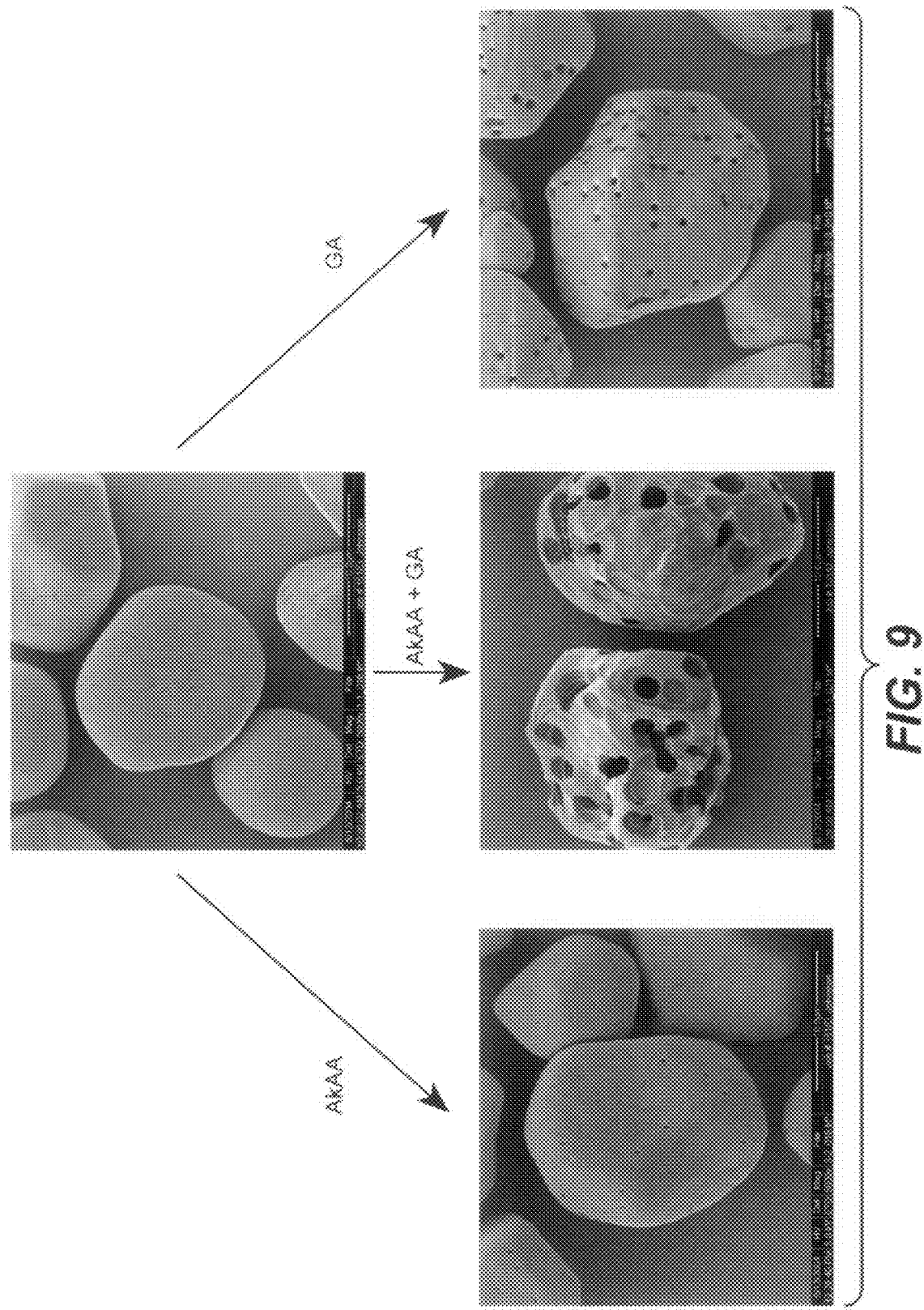

FIG. 9 illustrates SEMs of granular corn starch incubated with the enzymes described for FIG. 8: purified DISTILLASE (GA), purified AkAA (*A. kawachi* acid stable alpha amylase expressed in *Trichoderma reesei*), and the combination of AkAA and GA.

Figure 10A:
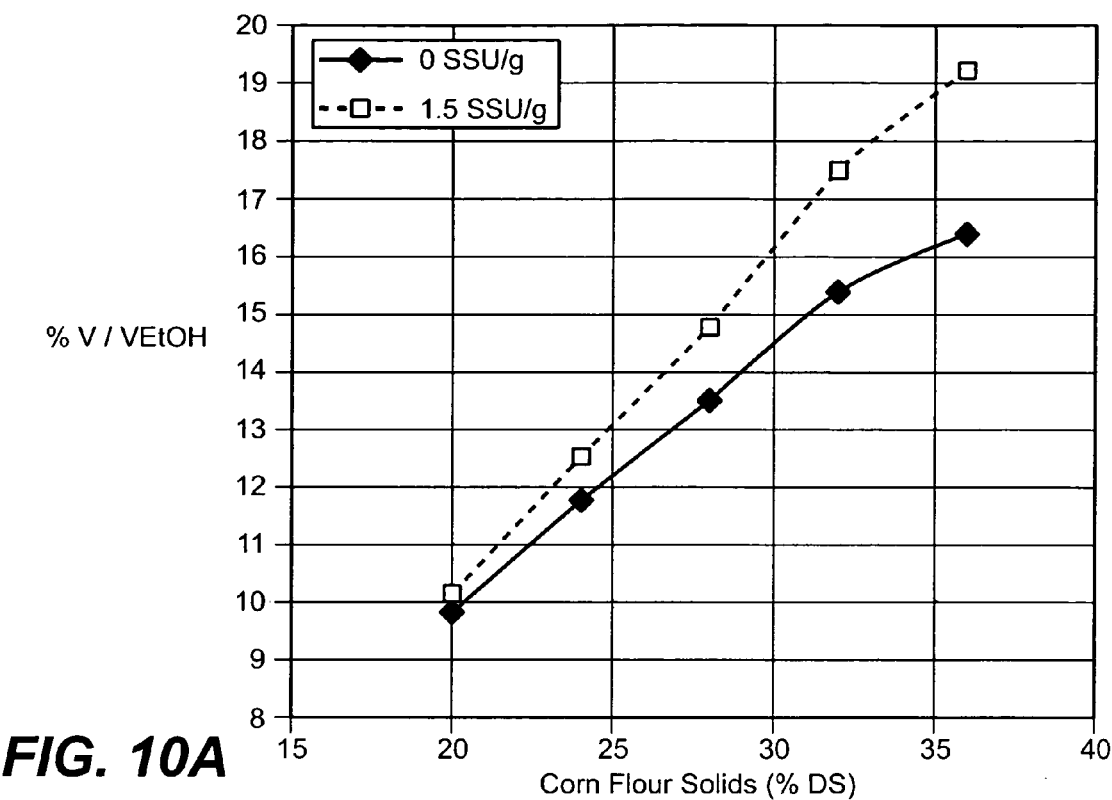
Figure 10B:
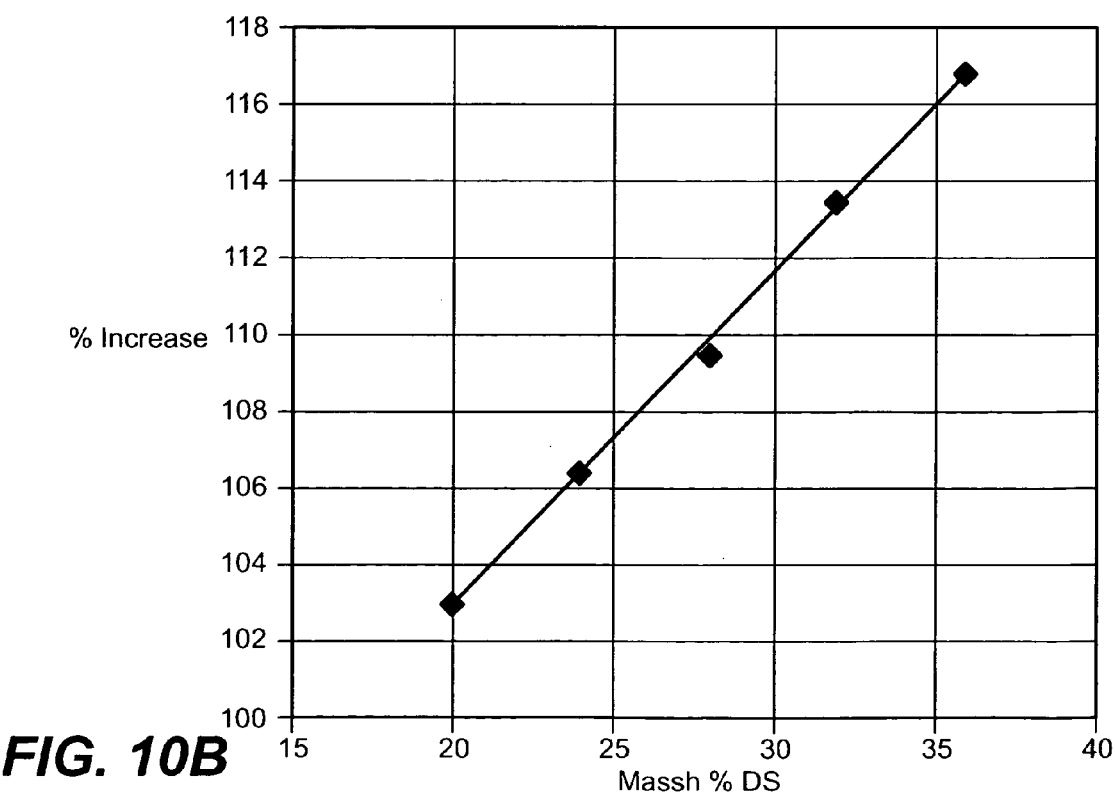

FIGS. 10A and 10B respectively illustrates the % increase in ethanol production with AkAA for corn mash solids (% ds) and mash solids (% ds).

Figure 11:
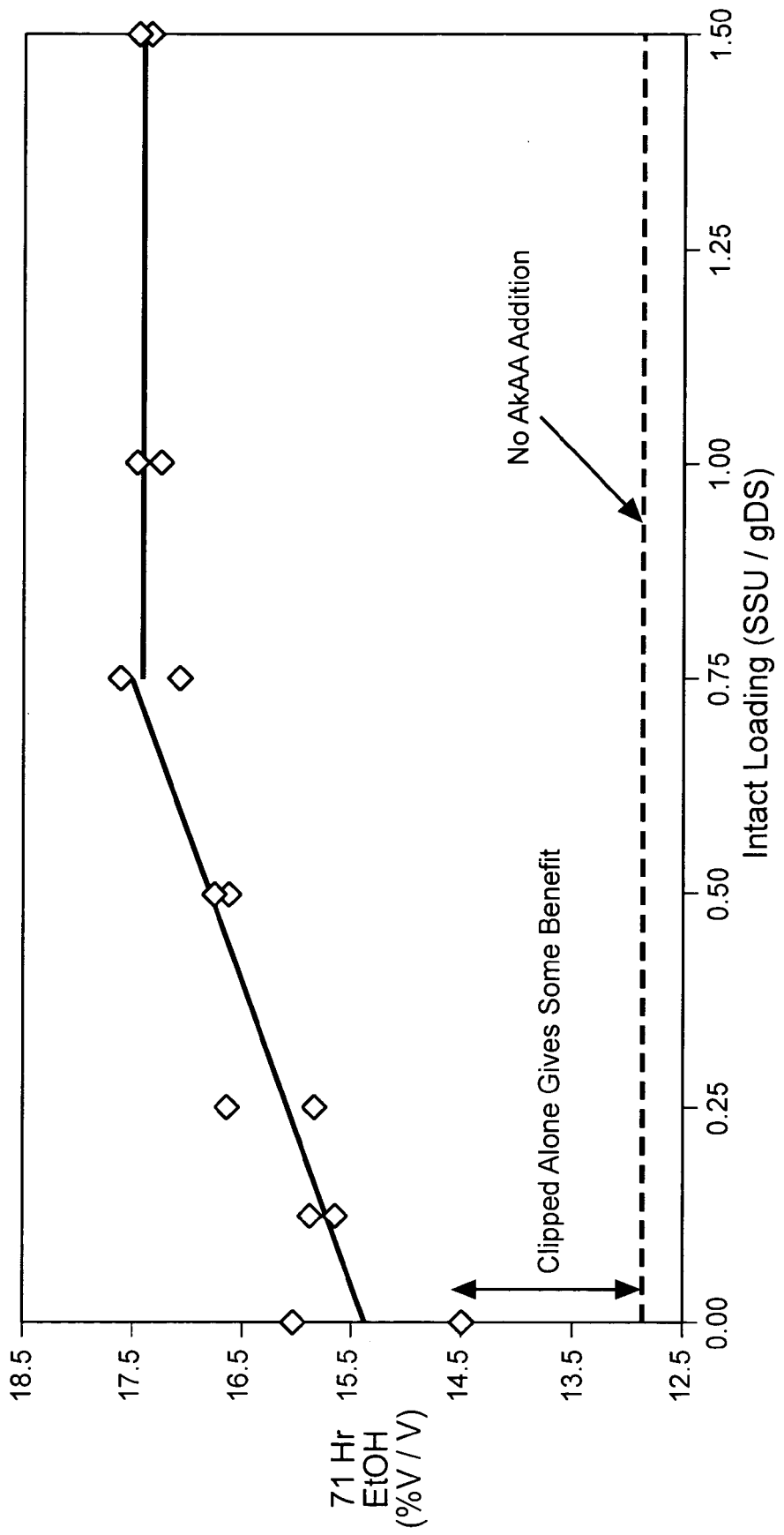

FIG. 11 depicts the % v/v ethanol measured at 71 hours for fermentation broths comprising varying ratios of intact and truncated AkAA at a fixed dosage level of 1.5 SSU/g ds AkAA.

FIG. 12 illustrates the amino acid sequence (SEQ ID NO: 11) of a glucoamylase derived from a *Trichoderma reesei*.

FIG. 13 illustrates the amino acid sequence (SEQ ID NO: 12) of a glucoamylase derived from a strain of *Humicola grisea* var. *thermoidea*.

FIG. 14 illustrates the amino acid sequence (SEQ ID NO: 13) of a glucoamylase derived from a strain of *Aspergillus awamori* var. *kawachi*.

DETAILED DESCRIPTION OF THE INVENTION

In some aspects, the present invention relies on routine techniques and methods used in the field of genetic engineering and molecular biology. The following resources include descriptions of general methodology useful in accordance with the invention: Sambrook et al., MOLECULAR CLONING: A LABORATORY MANUAL (2nd Ed., 1989); Kreigler, GENE TRANSFER AND EXPRESSION; A LABORATORY MANUAL (1990) and Ausubel et al., Eds. CURRENT PROTOCOLS IN MOLECULAR BIOLOGY (1994). These general references provide definitions and methods known to those in the art. However, it is not intended that the present invention be limited to any particular methods, protocols, and reagents described, as these may vary.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994) and Hale & Markham, THE HARPER COLLINS DICTIONARY OF BIOLOGY, Harper Perennial, NY (1991) provide one of skill with general dictionaries of many of the terms used in this invention.

Although any methods and materials similar or equivalent to those described herein can be used in the practice or testing of the present invention, the preferred methods and materials are described.

The invention will now be described in detail by way of reference only using the following definitions and examples. All patents and publications, including all sequences disclosed within such patents and publications, referred to herein are expressly incorporated by reference.

Numeric ranges are inclusive of the numbers defining the range.

Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention which can be had by reference to the specification as a whole.

A. DEFINITIONS

As used herein the term "starch" refers to any material comprised of the complex polysaccharide carbohydrates of plants, comprised of amylose and amylopectin with the formula $(C_6H_{10}O_5)_x$, wherein X can be any number. In particular, the term refers to any plant-based material including but not limited to grains, grasses, tubers and roots and more specifically wheat, barley, corn, rye, rice, sorghum, brans, cassava, millet, potato, sweet potato, and tapioca.

The term "granular starch" refers to raw (uncooked) starch, e.g., granular starch that has not been subject to gelatinization.

The terms "granular starch hydrolyzing (GSH) enzyme" and "having granular starch hydrolyzing (GSH) activity" refer to enzymes, which have the ability to hydrolyze starch in granular form.

The term "alpha-amylase (e.g., E.C. class 3.2.1.1)" refers to enzymes that catalyze the hydrolysis of alpha-1,4-glucosidic linkages. These enzymes have also been described as those effecting the exo or endohydrolysis of 1,4-α-D-glucosidic linkages in polysaccharides containing 1,4-α-linked D-glucose units. Another term used to describe these enzymes is "glycogenase". Exemplary enzymes include alpha-1,4-glucan 4-glucanohydrase glucanohydrolase.

The term "acid-stable alpha amylase ("asAA") refers to an alpha amylase that is active in the pH range of pH 3.0 to 7.0 and preferably 3.5 to 6.0.

The term "truncated asAA" refers to an asAA having GSH activity, wherein at least part of the starch binding domain has been eliminated. In some embodiments, a truncated asAA refers to an amino acid sequence which includes at least 65% of SEQ ID NO: 3 or includes at least 65% of a sequence having at least 90% sequence identity with SEQ ID NO: 3.

The term "starch binding domain (SBD)" refers to an amino acid sequence that binds preferentially to a starch (polysaccharide) substrate.

The term "linker" refers to a short amino acid sequence generally having between 3 and 40 amino acid residues which covalently binds an amino acid sequence comprising a starch binding domain with an amino acid sequence comprising a catalytic domain.

The term "catalytic domain" refers to a structural region of a polypeptide which is distinct from the SBD and which contains the active site for substrate hydrolysis.

The term "glucoamylase" refers to the amyloglucosidase class of enzymes (e.g., EC.3.2.1.3, glucoamylase, 1,4-alpha-D-glucan glucohydrolase). These are exo-acting enzymes, which release glucosyl residues from the non-reducing ends of amylose and amylopectin molecules. The enzyme also hydrolyzes alpha-1,6 and alpha-1,3 linkages although at much slower rate than alpha-1,4 linkages.

The term "glycosylation" refers to the post-transcriptional modification of a protein by the addition of carbohydrate moieties, wherein the carbohydrate is either N-linked or O-linked resulting in a glucoprotein. An N-linked carbohydrate moiety of a glycoprotein is attached by a glycosidic bond to the β-amide nitrogen of an asparagine residue. An O-linked carbohydrate is attached by a glycosidic bond to a protein through the hydroxy group of a serine or a threonine residue.

The term "recombinant" when used in reference to a cell, nucleic acid, protein or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The terms "protein" and "polypeptide" are used interchangeably herein. The conventional one-letter or three-letter code for amino acid residues is used herein.

A "signal sequence" means a sequence of amino acids bound to the N-terminal portion of a protein, which facilitates the secretion of the mature form of the protein outside the cell. The definition of a signal sequence is a functional one. The mature form of the extracellular protein lacks the signal sequence which is cleaved off during the secretion process.

The term "native acid-stable alpha amylase (n-asAA)" refers to an asAA produced from the endogenous expression of the asAA. For example, the term "n-asaA" means the endogenous expression of an acid-stable alpha amylase (ie, SEQ ID NO: 3) from an *Aspergillus kawachi*.

The terms "recombinant acid-stable alpha amylase (r-asAA)", "recombinantly expressed asAA" and "recombinantly produced asAA" refer to a mature asAA protein sequence that is produced in a host cell from the expression of a heterologous polynucleotide. For example, the term "r-asaA" means the *Aspergillus kawachi* acid-stable alpha amylase (i.e., SEQ ID NO: 3) is expressed and produced in a host in which a polynucleotide encoding the asaA has been introduced. The mature protein sequence of a r-asAA excludes a signal sequence.

A "gene" refers to a DNA segment that is involved in producing a polypeptide and includes regions preceding and following the coding regions as well as intervening sequences (introns) between individual coding segments (exons).

The term "nucleic acid" encompasses DNA, RNA, single stranded or double stranded and chemical modifications thereof. The terms "nucleic acid" and "polynucleotide" may be used interchangeably herein. Because the genetic code is degenerate, more than one codon may be used to encode a particular amino acid, and the present invention encompasses polynucleotides, which encode a particular amino acid sequence.

A "vector" refers to a polynucleotide sequence designed to introduce nucleic acids into one or more cell types. Vectors include cloning vectors, expression vectors, shuttle vectors, plasmids, phage particles, cassettes and the like.

An "expression vector" as used herein means a DNA construct comprising a DNA sequence which is operably linked to a suitable control sequence capable of effecting expression of the DNA in a suitable host. Such control sequences may include a promoter to effect transcription, an optional operator sequence to control transcription, a sequence encoding suitable ribosome binding sites on the mRNA, enhancers and sequences which control termination of transcription and translation.

A "promoter" is a regulatory sequence that is involved in binding RNA polymerase to initiate transcription of a gene. The promoter may be an inducible promoter or a constitutive promoter. A preferred promoter used in the invention is *Trichoderma reesei* cbh1, which is an inducible promoter.

"Under transcriptional control" is a term well understood in the art that indicates that transcription of a polynucleotide sequence, usually a DNA sequence, depends on its being operably linked to an element which contributes to the initiation of, or promotes transcription.

"Under translational control" is a term well understood in the art that indicates a regulatory process that occurs after mRNA has been formed.

As used herein when describing proteins and genes that encode them, the term for the gene is italicized, (e.g., the gene that encodes asaA (*A. kawachi* asAA) may be denoted as asaA). The term for the protein is generally not italicized and the first letter is generally capitalized, (e.g., the protein encoded by the asaA gene may be denoted as AsaA or asaA).

The term "derived" encompasses the terms "originated from", "obtained" or "obtainable from", and "isolated from" and as used herein means that the polypeptide encoded by the nucleotide sequence is produced from a cell in which the nucleotide is naturally present or in which the nucleotide sequence has been inserted.

The term "operably linked" refers to juxtaposition wherein the elements are in an arrangement allowing them to be functionally related. For example, a promoter is operably linked to a coding sequence if it controls the transcription of the sequence.

The term "selective marker" refers to a gene capable of expression in a host that allows for ease of selection of those hosts containing an introduced nucleic acid or vector. Examples of selectable markers include but are not limited to antimicrobials (e.g., hygromycin, bleomycin, or chloramphenicol) and/or genes that confer a metabolic advantage, such as a nutritional advantage on the host cell.

A polynucleotide or a polypeptide having a certain percent (e.g. 80%, 85%, 90%, 95%, or 99%) of sequence identity with another sequence means that, when aligned, that percentage of bases or amino acid residues are the same in comparing the two sequences. This alignment and the percent homology or identity can be determined using any suitable software program known in the art, for example those described in CURRENT PROTOCOLS IN MOLECULAR BIOLOGY (F. M. Ausubel et al. (eds) 1987, Supplement 30, section 7.7.18). Preferred programs include the GCG Pileup program, FASTA (Pearson et al. (1988) *Proc. Natl, Acad. Sci. USA* 85:2444-2448), and BLAST (BLAST Manual, Altschul et al., Natl. Cent. Biotechnol. Inf., Natl Lib. Med. (NCIB NLM NIH), Bethesda, Md., and Altschul et al., (1997) *NAR* 25:3389-3402). Another preferred alignment program is ALIGN Plus (Scientific and Educational Software, PA), preferably using default parameters. Another sequence software program that finds use is the TFASTA Data Searching Program available in the Sequence Software Package Version 6.0 (Genetics Computer Group, University of Wisconsin, Madison, Wis.).

One skilled in the art will recognize that sequences encompassed by the invention are also defined by the ability to hybridize under stringent hybridization conditions with the exemplified asaA sequence (e.g., SEQ ID NO:1). A nucleic acid is hybridizable to another nucleic acid sequence when a single stranded form of the nucleic acid can anneal to the other nucleic acid under appropriate conditions of temperature and solution ionic strength. Hybridization and washing conditions are well known in the art (See, e.g., Sambrook (1989) supra, particularly chapters 9 and 11). In some embodiments, stringent conditions correspond to a Tm of 65° C. and 0.1×SSC, 0.1% SDS.

"Host strain" or "host cell" means a suitable host for an expression vector or DNA construct comprising a polynucleotide encoding a granular starch hydrolyzing enzyme according to the invention. Specifically, host strains are preferably filamentous fungal cells. The host cell may be a wild type filamentous fungal host cell or a genetically modified host cell. In a preferred embodiment of the invention, "host cell" means both the cells and protoplasts created from the cells of a filamentous fungal strain and particularly a *Trichoderma* sp. or an *Aspergillus* sp.

The term "filamentous fungi" refers to all filamentous forms of the subdivision Eumycotina (See, Alexopoulos, C. J. (1962), INTRODUCTORY MYCOLOGY, Wiley, New York and AINSWORTH AND BISBY DICTIONARY OF THE FUNGI, 9$^{th}$ Ed. (2001) Kirk et al., Eds., CAB International University Press, Cambridge UK). These fungi are characterized by a vegetative mycelium with a cell wall composed of chitin, cellulose, and other complex polysaccharides. The filamentous fungi of the present invention are morphologically, physiologically, and genetically distinct from yeasts. Vegetative growth by filamentous fungi is by hyphal elongation and carbon catabolism is obligatory aerobic. In the present invention, the filamentous fungal parent cell may be a cell of a species of, but not limited to, *Trichoderma*, (e.g., *Trichoderma reesei* (previously classified as *T. longibrachiatum* and currently also known as *Hypocrea jecorina*), *Trichoderma viride*, *Trichoderma koningii*, *Trichoderma harzianum*); *Penicillium* sp., *Humicola* sp. (e.g., *Humicola insolens* and *Humicola grisea*); *Chrysosporium* sp. (e.g., *C. lucknowense*), *Gliocladium* sp., *Aspergillus* sp. (e.g., *A. oryzae*, *A. niger*, *A. kawachi* and *A. awamori*), *Fusarium* sp., *Neurospora* sp., *Hypocrea* sp., and *Emericella* sp. (See also, Innis et al., (1985) *Sci.* 228:21-26).

As used herein, the term "*Trichoderma*" or "*Trichoderma* sp." refer to any fungal genus previously or currently classified as *Trichoderma*.

The term "culturing" refers to growing a population of microbial cells under suitable conditions in a liquid or solid medium. In one embodiment, culturing refers to fermentative bioconversion of a starch substrate containing granular starch to an end-product (typically in a vessel or reactor). Fermentation is the enzymatic and anaerobic breakdown of organic substances by microorganisms to produce simpler organic compounds. While fermentation occurs under anaerobic conditions it is not intended that the term be solely limited to strict anaerobic conditions, as fermentation also occurs in the presence of oxygen.

The phrase "simultaneous saccharification and fermentation (SSF)" refers to a process in the production of end-products in which a microbial organism, such as an ethanol producing microorganism and at least one enzyme such as an asAA are in the same process step. In one embodiment of the present invention, SSF refers to the contemporaneous hydrolysis of granular starch substrates to saccharides including glucose and the fermentation of the saccharides into alcohol in the same reactor vessel.

The term "contacting" refers to the placing of the respective enzyme(s) in sufficiently close proximity to the respective substrate to enable the enzyme(s) to convert the substrate to the end-product. Those skilled in the art will recognize that mixing solutions of the enzyme with the respective substrates can effect contacting.

The term "enzymatic conversion" in general refers to the modification of a substrate by enzyme action. The term as used herein also refers to the modification of a granular starch substrate by the action of an enzyme.

As used herein the term "saccharification" refers to enzymatic conversion of starch to glucose.

The term "gelatinization" means solubilization of a starch molecule by cooking to form a viscous suspension.

The "gelatinization temperature" refers to the temperature at which gelatinization of a starch begins. The exact temperature of gelatinization depends on the specific starch and may vary depending on factors such as, plant species and environmental and growth conditions. The phrase "below the gelatinization temperature" refers to a temperature less than the temperature which starts gelatinization.

The term "liquefaction" refers to the stage in starch conversion in which gelatinized starch is hydrolyzed to give low molecular weight soluble dextrins.

The term "degree of polymerization (DP)" refers to the number (n) of anhydroglucopyranose units in a given saccharide. Examples of DP1 are the monosaccharides, such as glucose and fructose. Examples of DP2 are the disaccharides, such as maltose and sucrose. A DP>3 denotes polymers with a degree of polymerization of greater than 3.

The terms "end-product" or "desired end-product" refer to any carbon-source derived molecule product which is enzymatically converted from the granular starch substrate.

As used herein the term "dry solids content (ds)" refers to the total solids of a slurry in % on a dry weight basis.

The term "slurry" refers to an aqueous mixture containing insoluble solids.

The term "soluble starch hydrolyzate" refers to soluble products resulting from starch hydrolysis, which may comprise mono-, di-, and oligosaccharides (e.g. glucose, maltose and higher sugars).

The term "residual starch" refers to the remaining starch (soluble or insoluble) left in a composition after fermentation of a starch containing substrate.

The terms "distillers dried grain (DDG)" and "distillers dried grain with solubles (DDGS)" refer to useful co-products of grain fermentation.

The term "mash" refers to a mixture of a fermentable carbon source (carbohydrate) in water used to produce a fermented product, such as an alcohol. In some embodiments, the term "beer", "mash" and "fermentation broth" may be used interchangeability.

As used herein "ethanologenic microorganism" refers to a microorganism with the ability to convert a sugar or oligosaccharide to ethanol. The ethanologenic microorganisms are ethanologenic by virtue of their ability to express one or more enzymes that individually or together convert sugar to ethanol.

As used herein the term "ethanol producer" or ethanol producing microorganism" refers to any organism or cell that is capable of producing ethanol from a hexose or pentose. Generally, ethanol-producing cells contain an alcohol dehydrogenase and a pyruvate decarboxylase. Examples of ethanol producing microorganisms include fungal microorganisms such as yeast. A preferred yeast includes strains of *Saccharomyces*, particularly, *S. cerevisiae*.

The term "heterologous" with reference to a polynucleotide or protein refers to a polynucleotide or protein that does not naturally occur in a host cell. In some embodiments, the protein is a commercially important industrial protein. It is intended that the term encompass proteins that are encoded by naturally occurring genes, mutated genes, and/or synthetic genes.

The term "endogenous" with reference to a polynucleotide or protein refers to a polynucleotide or protein that occurs naturally in the host cell.

The terms "recovered", "isolated", and "separated" as used herein refer to a compound, protein, cell, nucleic acid or amino acid that is removed from at least one component with which it is naturally associated.

As used herein, the terms "transformed", "stably transformed" and "transgenic" used in reference to a cell means the cell has a non-native (e.g., heterologous) nucleic acid sequence integrated into its genome or as an episomal plasmid that is maintained through multiple generations.

As used herein, the term "expression" refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

As used herein the term "specific activity" means an enzyme unit defined as the number of moles of substrate converted to product by an enzyme preparation per unit time under specific conditions. Specific activity is expressed as units (U)/mg of protein.

As used herein the term "enzyme unit" refers to the amount of enzyme that produces a given amount of product per given amount of time under assay conditions. In some embodiments, an enzyme unit refers to the amount of enzyme that produces 1 micromole of product per minute under the specified conditions of the assay. For example, in one embodiment, the term "glucoamylase activity unit" (GAU) is defined as the amount of enzyme required to produce 1 g of glucose per hour from soluble starch substrate (4% ds) under assay conditions of 60° C. and pH 4.2.

In another embodiment, a granular starch hydrolyzing enzyme unit (GSHE U) is defined as being the amount of GSHE required to produce 1 mg of glucose per minute from granular starch under assay conditions of, for example 25° C. at pH 5.0. In a preferred embodiment, a GSHE U is defined as being the amount of a GSHE required to produce 1 mg glucose/min from a granular starch substrate at 50° C. at pH 4.5.

The term "yield" refers to the amount of end-product or desired end-products produced using the methods of the present invention. In some preferred embodiments, the yield is greater than that produced using methods known in the art. In some embodiments, the term refers to the volume of the end product and in other embodiment the term refers to the concentration of the end product.

"ATCC" refers to American Type Culture Collection located at Manassas, Va. 20108 (ATCC; <www.atcc.org>).

"NRRL" refers to the Agricultural Research Service Culture Collection, National Center for Agricultural Utilization Research (and previously known as USDA Northern Regional Research Laboratory), Peoria, Ill.

"A", "an" and "the" include plural references unless the context clearly dictates otherwise.

As used herein the term "comprising" and its cognates are used in their inclusive sense; that is, equivalent to the term "including" and its corresponding cognates.

B. PREFERRED EMBODIMENTS

Acid-Stable Alpha Amylases (asAA) Having Granular Starch Hydrolyzing (GSH) Activity In one embodiment, an asAA having GSH activity is obtained from a strain of *Aspergillus*, e.g., *A. oryzae, A. kawachi, A. niger*, and *A. awamori*. In a preferred embodiment, the asAA having GSH activity is obtained from a strain of *Aspergillus kawachi*.

In a particularly preferred embodiment, the asAA having GSH activity comprises an amino acid sequence having at least 80%, at least 85%, at least 90%, at least 93%, at least 94%, at least 95%, at least 96%, at least 97%, at least 98% and at least 99% sequence identity with the amino acid sequence set forth in SEQ ID NO: 3. In another embodiment, the asAA having GSH activity comprises an amino acid sequence having at least 90% sequence identity with SEQ ID NO: 3. In a further embodiment, the asAA having GSH activity comprises an amino acid sequence having at least 95% sequence identity to SEQ ID NO: 3. The asAA may also comprise an amino acid sequence having at least 98% sequence identity with SEQ ID NO: 3. In a further embodiment, the asAA having GSH activity comprises the amino acid sequence of SEQ ID NO: 3. In some embodiments, SEQ ID NO: 3 or a sequence having at least 85% identity thereto is considered an intact asAA.

In some embodiments, the asAA having GSH activity will include a catalytic domain having at least 96%, 97%, 98% and 99% sequence identity with SEQ ID NO: 9. In other embodiments, the asAA having GSH activity will include a SBD having at least 70%, 75%, 80%, 85%, 90%, 93%, 95%, 96%, 97% 98% and 99% sequence identity with the SBD of SEQ ID NO: 10.

In further embodiments, the asAA having GSH activity will comprise at least 97%, 98%, and 99% sequence identity with SEQ ID NO: 9; at least 96%, 97%, 98% and 99% sequence identity with SEQ ID NO: 8; and at least 95%, 96%, 97%, 98% and 99% sequence identity with SEQ ID NO: 10. In preferred embodiments, the catalytic domain and the SBD are obtained from an alpha amylase of an *Aspergillus kawachi* strain.

In other embodiments, the asAA having GSH activity is a truncated enzyme. In some embodiments the truncated asAA having GSH activity will include at least 60%, 65%, 70%, 75%, 80%, 83%, 85%, 88%, 90%, 93%, 95%, 96%, 97%, 98% and 99% of the amino acid sequence of SEQ ID NO: 3 and in other embodiments a truncated asAA will encompass at least 60%, 65%, 70%, 75%, 80%, 83%, 85%, 88%, 90%, 93%, 95%, 96%, 97%, 98% and 99% of a sequence having at least 90%, at least 95%, at least 98% and at least 99% sequence identity with SEQ ID NO: 3. The enzyme may be truncated at the carboxy terminus end of the polypeptide. In some embodiments the truncated asAA will include at least 430, at least 440, at least 450, at least 460 and at least 470 amino acids of SEQ ID NO: 3 or a sequence having at least 90% sequence identity thereto.

In some embodiments, the truncated asAA having GSH activity will include at least 90%, 95%, 96%, 97%, 98% and 99% of the catalytic domain of SEQ ID NO: 9 or a sequence having at least 97%, 98% and 99% sequence identity thereto.

In some embodiments, the truncated asAA having GSH activity will include the catalytic domain of SEQ ID NO: 9 or a sequence having at least 96%, 97%, 98% and 99% sequence identity thereto and a linker having at least 90%, 95%, 96%, 97%, 98% and 99% sequence identity to SEQ ID NO: 8. Preferably the truncated enzyme will include a catalytic domain having at least 97% sequence identity with SEQ ID NO: 9 and a linker having at least 95% sequence identity with SEQ ID NO: 8. In some embodiments, the truncated enzyme will include a catalytic domain having at least 96%, 97%, 98% and 99% sequence identity to SEQ ID NO: 9 and at least about 5, 10, 20, 25, 30 and 35 amino acids located downstream of the catalytic domain. In other embodiments, the truncated enzyme will include a catalytic domain and a linker as defined above and further a portion of the SBD having at least 70%, 75%, 80%, 85%, 90%, 93%, 95%, 96%, 97%, 98% and 99% sequence identity to the sequence of SEQ ID NO: 10. The portion of the SBD will include at least about 5, 10, 20, 30, 40, 50, 60, 70, 80, 90, and 100 amino acids located downstream of the linker.

In other embodiments, the asAA comprising the amino acid sequence of SEQ ID NO: 3 or an amino acid sequence having at least 95% sequence identity with SEQ ID NO: 3 is encoded by a polynucleotide having at least 70%, at least 80%, at least 85%, at least 90%, at least 93%, at least 95%, at least 96%, at least 97%, at least 98% and at least 99% sequence identity to the sequence of SEQ ID NO: 1. In a particularly preferred embodiment, the nucleic acid sequence encoding the asAA of SEQ ID NO: 3 (AsaA) is the nucleic acid sequence of SEQ ID NO: 1.

Recombinantly Expressed Enzymes and Host Cells:

In some embodiments of the invention, microorganisms are genetically engineered to express heterologous asAA having GSH activity and microorganisms may also be engineered to express heterologous glucoamylases. Preferred host cells are filamentous fungal cells. In a preferred embodiment, the filamentous fungal host is a strain of an *Aspergillus* sp, a *Trichoderma* sp, a *Fusarium* sp and a *Penicillium* sp. Particularly preferred fungal host cells include *A. nidulans, A. awamori, A. oryzae, A. aculeatus, A. niger, A. japonicus, T. reesei, T. viride, F. oxysporum*, and *F. solani*. *Aspergillus* strains are disclosed in Ward et al. (1993) *Appl. Microbiol. Biotechnol.* 39:738-743 and Goedegebuur et al., (2002) *Curr Gene* 41:89-98. In a most preferred embodiment, the host is a strain of *Trichoderma*, and particularly a strain of *T. reesei*. Strains of *T. reesei* are known and nonlimiting examples include ATCC No. 13631, ATCC No. 26921, ATCC No. 56764, ATCC No. 56765, ATCC No. 56767 and NRRL 15709. In some preferred embodiments, the host strain is a derivative of RL-P37. RL-P37 is disclosed in Sheir-Neiss et al. (1984) *Appl. Microbiol. Biotechnology* 20:46-53.

In some preferred embodiments, a *Trichoderma* host cell or an *Aspergillus* host cell is genetically engineered to express an asAA having GSH activity characterized by an amino acid sequence having at least 80%, 85%, 90%, 95%, 96%, 97%, 98% and 99% identity with SEQ ID NO: 3. In further embodiments, the asAA having GSH activity will comprise at least 97%, 98%, and 99% sequence identity with SEQ ID NO: 9; at least 96%, 97%, 98% and 99% sequence identity with SEQ ID NO: 8; and at least 95%, 96%, 97%, 98% and 99% sequence identity with SEQ ID NO: 10. In preferred embodiments, the asAA is obtained from an alpha amylase of an *Aspergillus kawachi* strain.

In other embodiments, the invention comprises a nucleotide sequence which encodes the polypeptide of SEQ ID NO: 3, the polypeptide of SEQ ID NO: 9 or a truncated enzyme as defined herein. In some embodiments, the polynucleotide encoding an asAA will have a nucleic acid sequence of SEQ ID NO: 1 or a nucleic acid sequence having at least 70% sequence identity with SEQ ID NO: 1.

In some embodiments, the asAA produced in a host cell engineered to include a heterologous polynucleotide encoding an asAA having GSH activity will have different, such as improved properties compared to the asAA produced by the endogenous expression of the asAA having GSH activity in a native host. These properties may include for example, increased enzyme activity, increased enzyme stability at lower pH levels or increased specific activity. In some embodiments, a heterologously produced asAA having GSH activity according to the invention will exhibit a maximum pH activity within a pH range of 3.0 to 6.0; a pH range of 3.0 to 5.0; a pH range of 3.5 to 5.0 and also within a pH range of 3.5 to 4.5. In other embodiments, a heterologously produced asAA will have a greater stability or residual activity at a pH level of 3.0, 3.5, 4.0, 4.5 and/or 5.0 compared to a corresponding asAA endogenously produced from a native host under essentially the same conditions. In some embodiments the level of enzyme stability for a heterologously produced asAA will be at least 0.5, 1.0, 2.0, or 2.5 times greater at a specific pH level compared to an endogenously expressed asAA at the same pH level. In some embodiments, these improved or different properties of the heterologously expressed asAA having GSH activity are particularly apparent in *Trichoderma* host cells. In some embodiments, the heterologously expressed asAA will be produced as an intact asAA having GSH activity which includes the catalytic domain, linker and SBD, for example the mature polypeptide illustrated in FIG. 2 (SEQ ID NO: 3). In other embodiments, the heterologously expressed asAA will be produced as a truncated asAA having GSH activity, for example, wherein the SBD is partially or completely cleaved off the catalytic domain.

In other embodiments, the host strain which is genetically engineered to express an asAA having GSH activity may also be genetically engineered to express a heterologous glucoamylase.

A host strain useful in the invention may have been previously manipulated through genetic engineering. In some embodiments, the genetically engineered host cell or strain may be a protease deficient strain. In other embodiments, expression of various native genes of the fungal host cell will have been reduced or inactivated. These genes include, for example genes encoding proteases and cellulolytic enzymes, such as endoglucanases (EG) and exocellobiohydrolases (CBH) (e.g. cbh1, cbh2, egl1, egl2 and egl3). U.S. Pat. No. 5,650,322 discloses derivative strains of RL-P37 having deletions in the cbh1 gene and the cbh2 gene. Reference is also made to U.S. Pat. No. 5,472,864.

Vectors:

While the description below refers specifically to asAA, one skilled in the art will readily understand that the same or similar methods apply to DNA constructs and vectors useful for introduction of a polynucleotide encoding GA into a host cell.

According to the invention, a DNA construct comprising nucleic acid encoding an asAA encompassed by the invention is constructed to transfer an asAA into a host cell. In one embodiment, the DNA construct is transferred to a host cell by an expression vector which comprises regulatory sequences operably linked to an asAA coding sequence.

The vector may be any vector which when introduced into a fungal host cell is integrated into the host cell genome and is replicated. Reference is made to the Fungal Genetics Stock Center Catalogue of Strains (FGSC, <www.fgsc.net>) for a list of vectors. Additional examples of suitable expression and/or integration vectors are provided in Sambrook et al., (1989) supra, Ausubel (1987) supra, van den Hondel et al. (1991) in Bennett and Lasure (Eds.) MORE GENE MANIPULATIONS IN FUNGI, Academic Press pp. 396-428 and U.S. Pat. No. 5,874,276. Particularly useful vectors include pFB6, pBR322, PUC18, pUC100 and pENTR/D.

In preferred embodiments, nucleic acid encoding an asAA encompassed by the invention is operably linked to a suitable promoter, which shows transcriptional activity in the fungal host cell. The promoter may be derived from genes encoding proteins either homologous or heterologous to the host cell. Preferably, the promoter is useful in a *Trichoderma* host. Suitable nonlimiting examples of promoters include cbh1, cbh2, egl1, egl2, pepA, hfb1, hfb2, xyn1 and amy. In one embodiment, the promoter is one that is native to the host cell. For example, when *T. reesei* is the host, the promoter is a native *T. reesei* promoter. In a preferred embodiment, the promoter is *T. reesei* cbh1, which is an inducible promoter and has been deposited in GenBank under Accession No. D86235. An "inducible promoter" is a promoter that is active under environmental or developmental regulation. In another embodiment, the promoter is one that is heterologous to the fungal host cell. Other examples of useful promoters include promoters from the genes of *A. awamori* and *A. niger* glucoamylase (glaA) (Nunberg et al., (1984) *Mol. Cell. Biol.* 4:2306-2315 and Boel et al., (1984) *EMBO J.* 3:1581-1585); *Aspergillus niger* alpha amylases, *Aspergillus oryzae* TAKA amylase, *T. reesei* xln1 and the *T. reesei* cellobiohydrolase 1. (EPA 137280A1).

In some preferred embodiments, the asAA coding sequence is operably linked to a signal sequence. The DNA encoding the signal sequence is preferably that which is naturally associated with the asAA gene to be expressed. Preferably, the signal sequence is encoded by an *Aspergillus kawachi* asaA gene that encodes an Ak-asaA. More preferably the signal sequence has at least 90%, at least 95%, at least 97%, and at least 99% sequence identity to the signal sequence of SEQ ID NO: 2. In additional embodiments, a signal sequence and a promoter sequence comprising a DNA construct or vector to be introduced into a fungal host cell are derived from the same source. For example, in some embodiments, the signal sequence is the cdh1 signal sequence which is operably linked to a cdh1 promoter.

In some embodiments, the expression vector also includes a termination sequence. In one embodiment, the termination sequence and the promoter sequence are derived from the same source. In another embodiment, the termination sequence is homologous to the host cell. A particularly suitable terminator sequence is cbh1 derived from a *Trichoderma* strain and particularly *T. reesei*. Other useful fungal terminators include the terminator from *A. niger* or *A. awamori* glucoamylase gene (Nunberg et al. (1984) supra, and Boel et al., (1984) supra).

In some embodiments, an expression vector includes a selectable marker. Examples of preferred selectable markers include ones which confer antimicrobial resistance (e.g., hygromycin and phleomycin). Nutritional selective markers also find use in the present invention including those markers known in the art as amdS argB and pyr4. Markers useful in vector systems for transformation of *Trichoderma* are known in the art (See, e.g., Finkelstein, chapter 6 in BIOTECHNOLOGY OF FILAMENTOUS FUNGI, Finkelstein et al. Eds. Butterworth-Heinemann, Boston, Mass. (1992), Chap. 6; and Kinghorn et al. (1992) APPLIED MOLECULAR GENETICS OF FILAMENTOUS FUNGI, Blackie Academic and Professional, Chapman and Hall, London). In a preferred embodiment, the selective marker is the amdS gene, which encodes the enzyme acetamidase, allowing transformed cells to grow on acetamide as a nitrogen source. The use of *A. nidulans* amdS gene as a selective marker is described in Kelley et al., (1985) *EMBO J.* 4:475-479 and Penttila et al., (1987) *Gene* 61:155-164.

An expression vector comprising a DNA construct with a polynucleotide encoding an asAA may be any vector which is capable of replicating autonomously in a given fungal host organism or of integrating into the DNA of the host. In some embodiments, the expression vector is a plasmid. In preferred embodiments, two types of expression vectors for obtaining expression of genes are contemplated.

The first expression vector comprises DNA sequences in which the promoter, asAA coding region, and terminator all originate from the gene to be expressed. In some embodiments, gene truncation is obtained by deleting undesired DNA sequences (e.g., DNA encoding unwanted domains) to leave the domain to be expressed under control of its own transcriptional and translational regulatory sequences.

The second type of expression vector is preassembled and contains sequences required for high-level transcription and a selectable marker. In some embodiments, the coding region for an asAA gene or part thereof is inserted into this general-purpose expression vector such that it is under the transcriptional control of the expression construct promoter and terminator sequences. In some embodiments, genes or part thereof are inserted downstream of the strong cbh1 promoter.

Methods used to ligate the DNA construct comprising a polynucleotide encoding an asAA, a promoter, a terminator and other sequences and to insert them into a suitable vector are well known in the art. Linking is generally accomplished by ligation at convenient restriction sites. If such sites do not exist, the synthetic oligonucleotide linkers are used in accordance with conventional practice. (See, Sambrook (1989) supra, and Bennett and Lasure, MORE GENE MANIPULATIONS IN FUNGI, Academic Press, San Diego (1991) pp 70-76). Additionally, vectors can be constructed using known recombination techniques (e.g., Invitrogen Life Technologies, Gateway Technology).

Where it is desired to obtain a fungal host cell having one or more inactivated genes known methods may be used (e.g. methods disclosed in U.S. Pat. No. 5,246,853, U.S. Pat. No. 5,475,101 and WO92/06209). Gene inactivation may be accomplished by complete or partial deletion, by insertional inactivation or by any other means which renders a gene nonfunctional for its intended purpose (such that the gene is prevented from expression of a functional protein). Any gene from a *Trichoderma* sp or other filamentous fungal host, which has been cloned can be deleted, for example cbh1, cbh2, egl1 and egl2 genes. In some embodiments, gene deletion may be accomplished by inserting a form of the desired gene to be inactivated into a plasmid by methods known in the art. The deletion plasmid is then cut at an appropriate restriction enzyme site(s), internal to the desired gene coding region, and the gene coding sequence or part thereof is replaced with a selectable marker. Flanking DNA sequences from the locus of the gene to be deleted (preferably between about 0.5 to 2.0 kb) remain on either side of the marker gene. An appropriate deletion plasmid will generally have unique restriction enzyme sites present therein to enable the fragment containing the deleted gene, including the flanking DNA sequences and the selectable markers gene to be removed as a single linear piece.

Transformation, Expression and Culture of Host Cells:

Introduction of a DNA construct or vector into a host cell includes techniques such as transformation; electroporation; nuclear microinjection; transduction; transfection, (e.g., lipofection mediated and DEAE-Dextrin mediated transfection); incubation with calcium phosphate DNA precipitate; high velocity bombardment with DNA-coated microprojectiles; and protoplast fusion. General transformation techniques are known in the art (See, e.g., Ausubel et al., (1987), supra, chapter 9; and Sambrook (1989) supra, and Campbell et al., (1989) *Curr. Genet.* 16:53-56). The expression of heterologous protein in *Trichoderma* is described in U.S. Pat. No. 6,022,725; U.S. Pat. No. 6,268,328; Harkki et al. (1991); *Enzyme Microb. Technol.* 13:227-233; Harkki et al., (1989) *Bio Technol.* 7:596-603; EP 244,234; EP 215,594; and Nevalainen et al., "*The Molecular Biology of Trichoderma and its Application to the Expression of Both Homologous and Heterologous Genes*", in MOLECULAR INDUSTRIAL MYCOLOGY, Eds. Leong and Berka, Marcel Dekker Inc., NY (1992) pp. 129-148). Reference is also made to Cao et al., (2000) *Sci.* 9:991-1001, EP 238023 and Yelton et al. (1984) *Proceedings. Natl. Acad. Sci.* USA 81:1470-1474 for transformation of *Aspergillus* strains.

Preferably, genetically stable transformants are constructed with vector systems whereby the nucleic acid encoding an asAA is stably integrated into a host strain chromosome. Transformants are then purified by known techniques.

In one nonlimiting example, stable transformants including an amdS marker are distinguished from unstable transformants by their faster growth rate and the formation of circular colonies with a smooth, rather than ragged outline on solid culture medium containing acetamide. Additionally, in some cases a further test of stability is conducted by growing the transformants on solid non-selective medium (i.e., medium that lacks acetamide), harvesting spores from this culture medium and determining the percentage of these spores which subsequently germinate and grow on selective medium containing acetamide. Alternatively, other methods known in the art may be used to select transformants.

In one specific embodiment, the preparation of *Trichoderma* sp. for transformation involves the preparation of protoplasts from fungal mycelia. (See, Campbell et al., (1989) *Curr. Genet.* 16:53-56). In some embodiments, the mycelia are obtained from germinated vegetative spores. The mycelia are treated with an enzyme that digests the cell wall resulting in protoplasts. The protoplasts are then protected by the presence of an osmotic stabilizer in the suspending medium. These stabilizers include sorbitol, mannitol, potassium chloride, magnesium sulfate and the like. Usually the concentration of these stabilizers varies between 0.8 M and 1.2 M. It is preferable to use about a 1.2 M solution of sorbitol in the suspension medium.

Uptake of DNA into the host *Trichoderma* sp. strain is dependent upon the calcium ion concentration. Generally, between about 10 mM $CaCl_2$ and 50 mM $CaCl_2$ is used in an uptake solution. Besides the need for the calcium ion in the uptake solution, other compounds generally included are a buffering system such as TE buffer (10 Mm Tris, pH 7.4; 1 mM EDTA) or 10 mM MOPS, pH 6.0 buffer (morpholinepropanesulfonic acid) and polyethylene glycol (PEG). It is believed that the polyethylene glycol acts to fuse the cell membranes, thus permitting the contents of the medium to be delivered into the cytoplasm of the *Trichoderma* sp. strain and the plasmid DNA is transferred to the nucleus. This fusion frequently leaves multiple copies of the plasmid DNA integrated into the host chromosome.

Usually a suspension containing the *Trichoderma* sp. protoplasts or cells that have been subjected to a permeability treatment at a density of $10^5$ to $10^7$/mL, preferably $2 \times 10^6$/mL are used in transformation. A volume of 100 μL of these protoplasts or cells in an appropriate solution (e.g., 1.2 M sorbitol; 50 mM $CaCl_2$) are mixed with the desired DNA. Generally a high concentration of PEG is added to the uptake solution. From 0.1 to 1 volume of 25% PEG 4000 can be added to the protoplast suspension. However, it is preferable to add about 0.25 volumes to the protoplast suspension. Additives such as dimethyl sulfoxide, heparin, spermidine, potassium chloride and the like may also be added to the uptake solution and aid in transformation. Similar procedures are available for other fungal host cells. (See, e.g., U.S. Pat. Nos. 6,022,725 and 6,268,328, both of which are incorporated by reference).

Generally, the mixture is then incubated at approximately 0° C. for a period of between 10 to 30 minutes. Additional PEG is then added to the mixture to further enhance the uptake of the desired gene or DNA sequence. The 25% PEG 4000 is generally added in volumes of 5 to 15 times the volume of the transformation mixture; however, greater and lesser volumes may be suitable. The 25% PEG 4000 is preferably about 10 times the volume of the transformation mixture. After the PEG is added, the transformation mixture is then incubated either at room temperature or on ice before the addition of a sorbitol and $CaCl_2$ solution. The protoplast suspension is then further added to molten aliquots of a growth medium. When the growth medium includes a growth selection (e.g., acetamide or an antibiotic) it permits the growth of transformants only.

Generally, cells are cultured in a standard medium containing physiological salts and nutrients (See, e.g., Pourquie, J. et al., BIOCHEMISTRY AND GENETICS OF CELLULOSE DEGRADATION, eds. Aubert, J. P. et al., Academic Press, pp. 71-86, 1988 and Ilmen, M. et al., (1997) *Appl. Environ. Microbiol.* 63:1298-1306). Common commercially prepared media (e.g., Yeast Malt Extract (YM) broth, Luria Bertani (LB) broth and Sabouraud Dextrose (SD) broth) also find use in the present invention.

Culture conditions are also standard, (e.g., cultures are incubated at approximately 28° C. in appropriate medium in shake cultures or fermenters until desired levels of asAA expression are achieved). Preferred culture conditions for a given filamentous fungus are known in the art and may be found in the scientific literature and/or from the source of the fungi such as the American Type Culture Collection and Fungal Genetics Stock Center.

After fungal growth has been established, the cells are exposed to conditions effective to cause or permit the expression of an asAA as defined herein. In cases where an asAA having GSH activity coding sequence is under the control of an inducible promoter, the inducing agent (e.g., a sugar, metal salt or antimicrobial), is added to the medium at a concentration effective to induce asAA expression.

Identification of asAA Activity:

In order to evaluate the expression of an asAA having GSH activity by a cell line that has been transformed with a heterologous polynucleotide encoding an asaA encompassed by the invention, assays can be carried out at the protein level, the RNA level or by use of functional bioassays particular to alpha amylase activity and/or production. In general assays employed include, Northern blotting, dot blotting (DNA or RNA analysis), RT-PCR (reverse transcriptase polymerase chain reaction), or in situ hybridization, using an appropriately labeled probe (based on the nucleic acid coding sequence) and conventional Southern blotting and autoradiography.

In addition, the production and/or expression of an asAA having GSH activity may be measured in a sample directly, for example, by assays directly measuring reducing sugars such as glucose in the culture media and by assays for measuring glucoamylase activity, expression and/or production. Substrates useful for assaying GSH activity include granular starch substrates. For example, glucose concentration may be determined by any convenient method such as by using glucose reagent kit No 15-UV (Sigma Chemical Co.) or an instrument such as Technicon Autoanalyzer. Also reference is made to glucose oxidase kits and glucose hexose kits commercially available from Instrumentation Lab. (Lexington, Mass.).

In addition, gene expression may be evaluated by immunological methods, such as immunohistochemical staining of cells, tissue sections or immunoassay of tissue culture medium, e.g., by Western blot or ELISA. Such immunoassays can be used to qualitatively and quantitatively evaluate expression of an asaA. The details of such methods are known to those of skill in the art and many reagents for practicing such methods are commercially available.

Alpha amylase activity may be measured by using the DNS method as described in Miller, G. L. (1959) *Anal. Chem.* 31:426-428. Glucoamylase activity may be assayed by the 3,5-dinitrosalicylic acid (DNS) method (See, Goto et al., (1994) *Biosci. Biotechnol. Biochem.* 58:49-54).

In some embodiments of the invention, the asAA having GSH activity expressed by a *Trichoderma* or *Aspergillus* host will be greater than 1 gram protein per liter (g/L), greater than 2 g/L, greater than 5 g/L, greater than 10 g/L, greater than 20 g/L, greater than 25 g/L, greater than 30 g/L, greater than 50 g/L and also greater than 100 g/L of culture media.

Methods for Purifying asAA:

In general, an asaA (including n-asAA or r-asAA) produced in cell culture is secreted into the medium and may be purified or isolated, e.g., by removing unwanted components from the cell culture medium. In some cases, an AsaA may be produced in a cellular form necessitating recovery from a cell lysate. In such cases the enzyme is purified from the cells in which it was produced using techniques routinely employed by those of skill in the art. Examples include, but are not limited to, affinity chromatography (Tilbeurgh et al., (1984) *FEBS Lett.* 16:215); ion-exchange chromatographic methods (Goyal et al., (1991) *Biores. Technol.* 36:37; Fliess et al., (1983) *Eur. J. Appl. Microbiol. Biotechnol.* 17:314; Bhikhabhai et al., (1984) *J. Appl. Biochem.* 6:336; and Ellouz et al., (1987) *Chromatography* 396:307), including ion-exchange using materials with high resolution power (Medve et al., (1998) *J. Chromatography A* 808:153; hydrophobic interaction chromatography (Tomaz and Queiroz, (1999) *J. Chromatography A* 865:123; two-phase partitioning (Brumbauer, et al., (1999) *Bioseparation* 7:287); ethanol precipitation; reverse phase HPLC; chromatography on silica or on a cation-exchange resin such as DEAE; chromatofocusing; SDS-PAGE; ammonium sulfate precipitation; and gel filtration using, e.g., Sephadex G-75.

Fermentations:

In some embodiments of the present invention, fungal cells expressing a heterologous asAA are grown under batch or continuous fermentation conditions. A classical batch fermentation is a closed system, wherein the composition of the medium is set at the beginning of the fermentation and is not subject to artificial alterations during the fermentation. Thus, at the beginning of the fermentation the medium is inoculated with the desired organism(s). In this method, fermentation is permitted to occur without the addition of any components to the system. Typically, a batch fermentation qualifies as a "batch" with respect to the addition of the carbon source and attempts are often made at controlling factors such as pH and oxygen concentration. The metabolite and biomass compositions of the batch system change constantly up to the time the fermentation is stopped. Within batch cultures, cells progress through a static lag phase to a high growth log phase and finally to a stationary phase where growth rate is diminished or halted. If untreated, cells in the stationary phase eventually die. In general, cells in log phase are responsible for the bulk of production of end product.

A variation on the standard batch system is the "fed-batch fermentation" system, which also finds use with the present invention. In this variation of a typical batch system, the substrate is added in increments as the fermentation progresses. Fed-batch systems are useful when catabolite repression is apt to inhibit the metabolism of the cells and where it is desirable to have limited amounts of substrate in the medium. Measurement of the actual substrate concentration in fed-batch systems is difficult and is therefore estimated on the basis of the changes of measurable factors such as pH, dissolved oxygen and the partial pressure of waste gases such as $CO_2$. Batch and fed-batch fermentations are common and well known in the art.

Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth and/or end product concentration. For example, in one embodiment, a limiting nutrient such as the carbon source or nitrogen source is maintained at a fixed rate an all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to medium being drawn off must be balanced against the cell growth rate in the fermentation. Methods of modulating nutrients and growth factors for continuous fermentation processes as well as techniques for maximizing the rate of product formation are well known in the art of industrial microbiology.

Plant Expression:

In some embodiments, a polynucleotide encoding an asAA encompassed by the invention may be transformed and expressed in a plant host. A host plant as used herein includes specific plant parts and the progeny thereof. Plant parts include stems, leaves, roots and seeds, and also specific tissues, such as but not limited to embryos and endosperms. A host plant may be a dicot plant, such as soybean, tobacco, tomato, potato, sugar beet or a monocot plant, such as a cereal grass (e.g. corn, barely, wheat, sorghum, rice and the like).

A DNA construct for use in transformation of plants may be constructed by means well known in the art. The DNA construct will include a coding region of an asAA gene of interest operably linked to regulatory sequences required for expression in plants and optionally enhancer sequences and a selectable marker. Regulatory sequences include promoter and terminator sequences.

The choice of a promoter will depend on whether or not expression is to be constitutive, inducible or tissue specific or during a specific developmental stage (See, Tague et al., *Plant Physiol*. (1988), 86:506). For constitutive expression the following promoters may be useful, 35S CaMV, 19S CaMV, Adh, nopaline synthase (Nos), sucrose synthase, cab, Pep-Case, rice actin (e.g. ActI) (McElroy et al., (1990) *Plant Cell* 2:163), alpha-tublin and maize ubiquitin1 (Christensen et al., (1989) *Plant Mol. Biol*. 12:619-632).

An inducible promoter is one that initiates transcription only when the plant is exposed to some particular external stimulus. Examples of inducible promoters include chemically induced and wound induced promoters, such as PR promoters (e.g. PR-1, PR-2, PR-3 and especially the tobacco PR-1a promoter (U.S. Pat. No. 5,614,395)) or phage T7 promoters. Wound induced promoters include promoters for proteinase inhibitors (e.g. promoters for polyphenol oxidases, LAD and TD) and potato pin2 (Xu et al., (1993) *Plant Mol. Biol*. 22:573-588).

Tissue-specific promoters such as endosperm promoters include zmGBS, maize granule-bound starch synthase gene promoters; ZmZ27, maize zein gene promoter; osGTI, rice glutelin 1 gene promoter and RP5, rice prolamin gene promoter (Russell et al., (1997) *Transgenic Res*. 6:157-168). Inducible, constitutive and tissue-specific plant promoters are well known to those in the art.

Enhancer sequences are frequently incorporated into plant transformation vectors to enhance gene expression. Enhancers may include, for example, intron sequences such as introns of the maize adhI gene.

Selectable markers are readily available and known in the art. One may use for example the bar-bialaphos or EPSPS-glyphosate selective system (White et al., (1990) *Nucl Acids Res*. 18:1062), hph hygromycin phosphotransferase (Bloching et al., *Mol. Cell. Biol*. 4: 2929-2931), and nptII kanamycin resistant gene (Messing et al., (1982) *Gene* 19:259-268 and Bevan et al., (1983) *Nature* 304:184-187).

A variety of transcriptional terminators are available for use in DNA constructs and/or expression vectors. Suitable terminator sequences include those known to function in plants such as but not limited to, the 35S CaMV terminator, tml terminator, nopaline synthase (Nos) terminator and pes rbcS E9 terminator.

A DNA construct or expression vector may be incorporated into the host plant or plant part according to conventional known techniques. Some of these techniques for dicots include preferably *Agrobacterium tumefaciens* mediate gene transfer and for monocots include microprojectile bombardment, PEG mediated transformation of protoplasts, electroporation, and also *Agrobacterium* infection. (Reference is made to U.S. Pat. No. 6,803,499, U.S. Pat. No. 6,777,589, Potrykus et al., (1985) *Mol. Gen. Genet*. 199:169-177, Potrykus (1990) *Biotechnol* 8:535, Klein et al., (1987) *Nature* 327:70-73, Shimamoto et al., (1989) *Nature* 338:274, Fromm et al., (1990) *Biotechnol*. 8:833-839). Many vectors suitable for use with these transformation systems are available. (See, McElroy et al. (1991) *Mol. Gen. Genet*. 231:150-160). Gene expression may be measure by methods known in the art and as described herein for measurement of fungal expression.

Compositions:

A particularly useful enzyme composition according to the invention is a granular starch hydrolyzing enzyme composition which includes an asAA having at least 85%, 90%, 95%, 96%, 97%, 98% or 99% sequence identity to SEQ ID NO: 3. In some embodiments, the asAA is obtained from the heterologous expression of asAA and particularly the heterologous expression of an *Aspergillus* kawachi acid stable alpha amylase in a *Trichoderma* or *Aspergillus* host. Another particularly useful enzyme composition of the invention is a granular starch hydrolyzing enzyme composition which comprises a truncated asAA having at least 97%, 98% and 99% sequence identity to the sequence of SEQ ID NO: 9.

In further embodiments, an enzyme composition according to the invention will include a combination of asAA enzymes having GSH activity which include a) intact asAA having GSH activity which include a sequence having at least 85%, 90%, 95%, 96%, 97%, 98% and 99% identity to SEQ ID NO: 3 and b) a truncated asAA having GSH activity. In some embodiments the truncated asAA having GSH activity will be a sequence having at least 96%, 97%, 98% and 99% sequence identity with the sequence of SEQ ID NO: 9.

In some embodiments, the amount of intact asAA having GSH activity compared to the total amount of asAA having GSH activity (intact plus truncated) in the enzyme composition will be at least about 20%, 25%, 30%, 35%, 40%, 45%, 50%, 55%, 60%, 65%, 70%, 75%, 80%, 85%, 90%, 95%, and 98%. In other embodiments, the ratio of intact asAA having GSH activity to truncated asAA having GSH activity in an enzyme composition according to the invention will be about 10% to 90%, 20% to 80%, 30% to 70%, 35% to 65%, 40% to 60%, 45% to 55%, 50% to 50%, 55% to 45%, 60% to 40%, 65% to 35%, 70% to 30%, 80% to 20% and 90% to 10% (intact to truncated). In some preferred embodiments, the ratio of intact to truncated will be between about 40% to 60% and about 60% to 40%.

In some embodiments, the asAA is available as a cell free filtrate (for example wherein the asAA is isolated from a culture medium), and in other embodiments, the asAA is available in a culture medium containing the fungal host cells which express and secrete the asAA having GSH activity. In a further aspect, the invention encompasses a fermentation or culture medium comprising an acid stable alpha amylase (asAA) having granular starch hydrolyzing activity produced from a culture of *Trichoderma* cells, said *Trichoderma* cells comprising a heterologous polynucleotide encoding the asAA which has at least 90% sequence identity with SEQ ID NO: 3.

As understood by those in the art, the quantity of asAA having GSH activity used in the compositions and methods of the present invention will depend on the enzymatic activity of the asAA. In some embodiments, the range of asAA present in the enzyme compositions is from 0.01 to 40 SSU; 0.01 to 30 SSU; 0.01 to 20 SSU; 0.01 to 15 SSU; and 0.01 to 10 SSU per g ds.

Another particularly useful enzyme composition according to the invention is a granular starch hydrolyzing enzyme composition as disclosed above which additionally includes a glucoamylase.

Glucoamylase (GA) (E.C. 3.2.1.3) enzymes, which may be useful in the compositions according to the invention may be wild type glucoamylases or genetically modified glucoamylases, which include variant and hybrid glucoamylases. In general, glucoamylases may be derived from bacteria, plants and fungal sources. Preferred glucoamylases useful in the compositions and methods of the invention are produced by several strains of filamentous fungi and yeast. In particular, glucoamylases secreted from strains of *Aspergillus* and *Trichoderma* are commercially important. Sources of these glucoamylases include: *Aspergillus niger* G1 and G2 glucoamylase and variants thereof (Boel et al., (1984) *EMBO J.* 3:1097-1102; WO 92/00381; WO 00/04136 and U.S. Pat. No. 6,352,851); *Aspergillus awamori* glucoamylases (WO 84/02921); *Aspergillus oryzae* glucoamylases and variants thereof (Hata et al., (1991) *Agric. Biol. Chem.* 55:941-949) and *Aspergillus shirousami* (See, Chen et al., (1996) *Prot. Eng.* 9:499-505; Chen et al. (1995) *Prot. Eng.* 8:575-582; and Chen et al., (1994) *Biochem J.* 302:275-281). Glucoamylases are also obtained from strains of *Talaromyces* such as those derived from *T. emersonii, T. leycettanus, T. duponti* and *T. thermophilus* (WO 99/28488; U.S. Pat. No. RE: 32,153; and U.S. Pat. No. 4,587,215); strains of *Rhizopus*, such as *R. niveus* and *R. oryzae*; strains of *Mucor*; strains of *Trichoderma*, such as *T. reesei* and *T. viride*; and strains of *Humicola*, such as *H. grisea* (See, Boel et al., (1984) *EMBO J.* 3:1097-1102; WO 92/00381; WO 00/04136; Chen et al., (1996) *Prot. Eng.* 9:499-505; Taylor et al., (1978) *Carbohydrate Res.* 61:301-308; U.S. Pat. No. 4,514,496; U.S. Pat. No. 4,092,434; and Jensen et al., (1988) *Can. J. Microbiol.* 34:218-223). Other glucoamylases useful in the present invention include those obtained from *Athelia rolfsii* and variants thereof (WO 04/111218).

Enzymes having glucoamylase activity used commercially are produced for example, from *Aspergillus niger* (trade name DISTILLASE, OPTIDEX L-400 and G ZYME G990 4X from Genencor International Inc.) or *Rhizopus* species (trade name CU.CONC from Shin Nihon Chemicals, Japan). Also the commercial digestive enzyme, trade name GLUCZYME from Amano Pharmaceuticals, Japan (Takahashi et al., (1985) *J. Biochem.* 98:663-671). Additional enzymes include three forms of glucoamylase (E.C.3.2.1.3) of a *Rhizopus* sp., namely "Gluc1" (MW 74,000), "Gluc2" (MW 58,600) and "Gluc3" (MW 61,400). Gluc1 finds particular use in the present invention.

Some GA enzymes are also granular starch hydrolyzing enzyme(s) (GSHE) (See e.g., Tosi et al., (1993) *Can. J. Microbiol.* 39:846-855). These GA-GSHEs not only have glucoamylase activity, but also are able to hydrolyze granular (raw) starch. GA-GSHEs have been recovered from fungal cells and particularly filamentous fungal cells such as *Humicola* sp., *Aspergillus* sp., *Trichoderma* sp. and *Rhizopus* sp. A *Rhizopus oryzae* GA-GSHE has been described in Ashikari et al., (1986) *Agric. Biol. Chem.* 50:957-964 and U.S. Pat. No. 4,863,864. Also reference is made to *Rhizopus niveus*. A *Humicola grisea* GA-GSHE is described by Allison et al., (1992) *Curr. Genet.* 21:225-229, Tosi et al., (1993) *Can. J. Microbiol.* 39: 846-852, Campos et al., (1995) *App. And Environ. Microbiol.* 61:2436-2438 and European Patent No., 171218. The gene encoding this enzyme is also known in the art as "gla1". An *Aspergillus awamori* var. *kawachi* GA-GSHE is described by Hayashida et al., (1989) *Agric. Biol. Chem.* 53:923-929. An *Aspergillus shirousami* GA-GSHE is described by Shibuya et al., (1990) *Agric. Biol. Chem.* 54:1905-1914. One particular GA-GSHE preparation for use in the present invention includes enzyme preparations sold under the designation "M1" available from Biocon India, Ltd, India.

In some preferred embodiments, the glucoamylase is a GA-GSHE derived from *Trichoderma* characterized by the protein sequence of SEQ ID NO:11 or a sequence having at least 70%, 75%, 80%, 85%, 90%, 93%, 95%, 97%, 98% and 99% sequence identity with SEQ ID NO:11.

In other preferred embodiments, the glucoamylase is a GA-GSHE derived from an *Aspergillus* characterized by the protein sequence of SEQ ID NO: 13 or a sequence having at least 70%, 75%, 80%, 85%, 90%, 93%, 95%, 97%, 98% and 99% sequence identity with SEQ ID NO: 13.

In one embodiment, a GA-GSHE enzyme may be derived from a strain of *Humicola grisea*, particularly a strain of *H. grisea* var. *thermoidea* (See, U.S. Pat. No. 4,618,579). In some preferred embodiments, the *Humicola grisea* GA-GSHE enzyme is recovered from fungi including ATCC 16453, NRRL (USDA Northern Regional Research Laboratory, Peoria, Ill.) 15219, NRRL 15220, NRRL 15221, NRRL 15222, NRRL 15223, NRRL 15224 and NRRL 15225, as well as genetically altered strains thereof. These species produce enzymatic glucoamylase preparations that are immunologically the same (See, EP 0 171 218).

In other preferred embodiments, the *Humicola grisea* GA-GSHE may have the protein sequence of SEQ ID NO: 12 or a sequence having at least 70%, 75%, 80%, 85%, 90%, 93%, 95%, 97%, 98% and 99% sequence identity with SEQ ID NO: 12.

The amount of glucoamylase useful in an enzyme composition is in the range of 0.001 to 10.0 GAU/g ds, also 0.01 to 10.0 GAU/g ds and also 0.1 to 10.0 GAU/g ds. The activity of a GA-GSHE preparation may be defined in terms of the glucoamylase activity.

In some embodiments, the enzyme composition will include an asAA having at least 85%, 90%, 95%, 98% or 99% sequence identity to SEQ ID NO: 3, wherein the asAA is obtained from the heterologous expression of asAA and particularly the heterologous expression of an *Aspergillus kawachi* asAA in a *Trichoderma* or an *Aspergillus* host and a glucoamylase. The glucoamylase may be an enzyme that has not been genetically modified or the enzyme may be a variant or hybrid GA. In other embodiments, the enzyme composition will include a combination of a glucoamylase, intact asAA and truncated asAA as defined above. In some preferred embodiments, the GA is obtained from an *Aspergillus* strain, e.g., DISTILLASE®. In other embodiments, the GA is obtained from a *Rhizopus, Trichoderma* or *Humicola* strain. More specifically, in some embodiments the asAA enzyme compositions will be combined with a glucoamylase which comprises an amino acid sequence having at least 90%, 93%, 95% 96%, 97%, 98% and 99% sequence identity to sequence SEQ ID NO: 11, SEQ ID NO: 12 or SEQ ID NO: 13.

While not meant to limit the invention, other particularly preferred enzyme compositions include the following combinations: a) a glucoamylase obtained from an *Aspergillus niger* and an asAA having GSH activity having at least 95% sequence identity with SEQ ID NO: 3; b) a glucoamylase obtained from an *Aspergillus niger* and an asAA having GSH activity having at least 96% sequence identity with SEQ ID NO: 9; c) a glucoamylase obtained from an *Aspergillus niger*, an asAA having GSH activity having at least 95% sequence identity to SEQ ID NO: 3 and an asAA having at least 96% sequence identity with SEQ ID NO: 9; d) an asAA enzyme composition encompassed by the invention and a glucoamylase having an amino acid sequence of at least 90% sequence identity to SEQ ID NO: 11; e) an asAA enzyme composition encompassed by the invention and a glucoamylase having an amino acid sequence of at least 90% sequence identity to SEQ ID NO: 12; and f) an asAA enzyme composition encompassed by the invention and a glucoamylase having an amino acid sequence of at least 90% sequence identity to SEQ ID NO: 13.

Some particularly useful enzymatic compositions include a mixture of an asAA having at least 95% sequence identity to SEQ ID NO: 3 and a GA having 0.1 to 10 GAU/g ds. Another particularly useful enzymatic composition includes a mixture of an asAA having at least 98% sequence identity to SEQ ID NO: 3 and a GA having 0.1 to 10 GAU/g ds. Yet another particularly useful enzymatic composition includes a mixture of an asAA having at least 98% sequence identity to SEQ ID NO: 9 and a GA having 0.1 to 10 GAU/g ds.

In some embodiments, the ratio of asAA having GSH activity (SSU) to GA activity (GAU) will be in the range of 40:1 to 1:40, also 30:1 to 1:30, also 20:1 to 1:20 and 15:1 to 1:15. In further embodiments, the ratio (SSU to GAU) will be in the range of about 20:1 to 1:10; about 10:1 to 1:10; about 10:1 to 1:5; about 5:1 to 1:5, about 4:1 to 1:4; about 3:1 to 1:3; about 2:1 to 1:4 and also about 2:1 to 1:2. In some preferred embodiments, the ratio of SSU to GAU will be between about 4:1 to 2:1.

In other embodiments, the asAA having GSH activity and the GA are present in a ratio such that the hydrolysis of granular starch in a substrate is greater than the additive effect of the enzymes when supplied at the same levels under the same conditions. In some cases the hydrolysis will be at least 1.0, at least 1.5, at least 2.0 and also at least 3.0 times greater. The exact amounts of the components encompassed by the compositions of the invention will depend on the combination of enzymes.

In general, as AA having GSH activity will be mixed with a slurry of a granular starch substrate in an amount of about 0.01 to 15.0 SSU per gram of dry solids content of the slurry. In some embodiments, the asAA having GSH activity is added in an amount of about 0.01 to 10.0 SSU, about 0.01 to 5.0 SSU; about 0.05 to 10.0 SSU; about 0.05 to 5.0 SSU; about 0.1 to 10.0 SSU; about 0.1 to 5.0 SSU; about 0.1 to 2.0 SSU; about 0.25 to 2.5 SSU; about 0.5 to 5.0 SSU; about 0.5 to 2.5 SSU; and also about 0.5 to 1.5 SSU per gram of dry solids content of the slurry.

As understood by those in the art, the quantity of glucoamylase used in the method and compositions of the present invention depends on the enzymatic activity of the glucoamylase. Generally, an amount of between 0.001 and 10.0 GAU of glucoamylase per gram (ds) slurry adjusted to 20-45% dry solids may be added. In some embodiments, the glucoamylase is added in an amount between 0.01 and 10 GAU; between 0.01 and 5.0 GAU; between 0.05 and 5.0 GAU: between 0.1 and 10.0 GAU; between 0.1 and 5.0 GAU; between 0.1 and 2.0 GAU; between 0.25 and 1.5 GAU of glucoamylase per gram (ds) slurry. In one preferred embodiment, the dosage range for glucoamylase will be from 0.1 to 2.0 GAU/g (ds) slurry.

Additional enzymes may be included in the compositions and methods encompassed by the invention. These additional enzymes, which find use in the present invention include debranching enzymes such as pullulanases (E.C. 3.2.1.41) and isoamylases (E.C. 3.2.1.68). Such enzymes hydrolyze alpha-1,6-glucosidic bonds. Thus, during the hydrolysis of the starch, debranching enzymes remove successive glucose units from the non-reducing ends of the starch. Another enzyme that may be used in the compositions of the invention are beta-amylases (E.C. 3.2.1.2). These are exo-acting maltogenic amylases, which catalyze the hydrolysis of 1,4-alpha-glucosidic linkages in amylose, amylopectin and related glucose polymers. Some of these enzymes are characterized as having an optimum pH range from 4.5 to 7.0 and optimum temperature range from 40° C. to 65° C. Commercial beta-amylases are available for example SPEMZYME BBA and OPTIMALT from Genencor International Inc.

Additional enzymes may include alpha amylases, which may or may not be characterized by having GSH activity. Examples of alpha amylases include both bacterial and fungal alpha amylases and variants thereof. Specific nonlimiting examples include alpha amylases from *Bacillus amyloliquefaciens, Bacillus stearothermophilus, B. licheniformis* and variants or hybrids thereof (U.S. Pat. No. 5,093,257; U.S. Pat. No. 6,093,562; U.S. Pat. No. 5,736,499; U.S. Pat. No. 5,958, 739; U.S. Pat. No. 6,436,888; U.S. Pat. No. 6,867,031; WO 96/39528; WO 96/23874 and WO 05/001064). Commercially available alpha amylases are SPEZYME FRED and SPEZYME ETHYL (Genencor International Inc.). Cyclodextrin glucanotransferases (CGTases) (e.g. E.C. 2.4.1.19) and variants thereof may also find use in the invention (U.S. Pat. No. 5,278,059; U.S. Pat. No. 5,545,587 and WO 05/003337).

Further additional enzymes which may be used are proteases, such as fungal and bacterial proteases. Fungal proteases include for example, those obtained from *Aspergillus, Trichoderma, Mucor* and *Rhizopus*, such as *A. niger, A.*

*awamori*, *A. oryzae* and *M. miehei*. Other enzymes include but are not limited to cellulases, such as endoglucanases; hemicellulases, such as mannases; lipases (e.g., E.C. 3.1.1.3), glucose oxidases, pectinases, xylanases, transglucosidases, alpha 1,6 glucosidases (e.g., E.C. 3.2.1.20) and cutinases (e.g. E.C. 3.1.1.74).

The effective amount of these enzymes to be included in the methods of the invention can be readily determined by one skilled in the art.

In some embodiments, an antimicrobial may be added to the compositions and fermentation medium of the invention. Antimicrobials are compounds that kill or inhibit the growth of microorganisms.

Enzyme compositions comprising an asAA according to the invention may include compositions for starch conversion and particularly granular starch conversion, cleaning compositions, compositions for paper and pulp production, compositions for textiles, brewing compositions, baking compositions, compositions for sweeteners and the like.

In one preferred embodiment, an enzyme composition comprising an asaA as encompassed by the invention and optionally in combination with a glucoamylase will be used for producing ethanol. In some embodiments, at least 8%, 10%, 12%, 14%, 16% and 18% ethanol will be produced using a composition of the invention.

In some embodiments, the ethanol will be produced during a simultaneous saccharification and fermentation. In some embodiments, the enzyme composition will be contemporaneously combined with a slurry of a granular starch substrate and an ethanol producing microorganism and the mixture will be fermented in a single step. The slurry may have about 10-50% ds; about 10-45%; about 15-40%; about 20-40%; about 25-40%; or about 25-35% ds.

A granular starch substrate may be obtained from any plant part including stems, grains, roots and tubers. Particularly preferred plant sources include corn; wheat; rye; sorghum; rice; millet; barley; cassava; legumes, such as beans and peas; potatoes; sweet potatoes; bananas; sugarcane; and tapioca.

Specifically contemplated starch substrates are cornstarch and wheat starch. The starch from a grain may be ground or whole and includes corn solids, such as kernels, bran and/or cobs. In addition, the grain may be fractionated (e.g., endosperm, fiber or germ in corn or gluten, starch A or starch B in wheat). The starch may be highly refined raw starch or feedstock from starch refinery processes. Those of general skill in the art are well aware of available methods which may be used to prepare granular starch substrates for use in the methods encompassed by the invention. Some of these methods include dry milling of whole cereal grains using hammer mills and roller mills and wet milling.

In some embodiments, at least 80%, 70%, 60%, 50%, 40% 30% of the milled cereal grain will pass through a 0.5 mm screen. In other embodiments, a fine particle size is preferred and therefore at least 80%, 85%, 90% and 95% of the milled cereal grain will pass through a 0.5 mm screen. In yet other embodiments, the milled cereal grain may be a coarse particle and in these instances at least 90% of the milled grain will pass through a 1.0 mm, a 1.5 mm or a 2.0 mm screen but only about less than 5%, 10%, and 15% will pass through a 0.5 mm screen.

Various starches are commercially available. For example, cornstarches are available from Cerestar, Sigma, and Katayama Chemical Industry Co. (Japan); wheat starches are available from Sigma; sweet potato starches are available from Wako Pure Chemical Industry Co. (Japan); and potato starch is available from Nakaari Chemical Pharmaceutical Co. (Japan).

Various references have reported on the amount of starch found in cereal grains and reference is made to The Alcohol Textbook, $3^{rd}$ Ed. K. Jacques et al., Eds. 1999, Nottingham University Press. For example, corn contains about 60-68% starch; barley contains about 55-65% starch; millet contains about 75-80% starch; wheat contains about 60-65% starch; and polished rice contains 70-72% starch.

In some embodiments, a granular starch substrate is slurried (generally with water) and the slurry comprises i) about 10 to about 55% dry solids content (ds); ii) about 15 to about 50% dry solids content; iii) about 20 to about 45% dry solids content; iv) about 25 to about 45% dry solids content; v) about 30 to about 45% dry solids content; vi) about 30 to about 40% dry solids content; and also vii) about 30 to 35% dry solids content. The granular starch slurry is contacted with an enzyme composition according to the invention at a temperature below the gelatinization temperature of the starch in the granular starch substrate to yield glucose.

The exact temperature used in accordance with the methods of the invention depends upon the specific starch substrate used. General starch gelatinization temperature ranges are disclosed in Swinkels pages 32-38 in STARCH CONVERSION TECHNOLOGY, eds Van Beynum et al., (1985) Marcel Dekker Inc., NY and THE ALCOHOL TEXTBOOK, A REFERENCE FOR THE BEVERAGE, FUEL AND INDUSTRIAL ALCOHOL INDUSTRIES, $3^{rd}$ Ed., eds Jacques et al., 1999, Nottingham University Press, UK. In some embodiments, a method encompassed by the invention will be conducted at a temperature of least about 10° C., 15° C., 20° C., 25° C., 30° C., 35° C., 40° C., 45° C., 50° C., 55° C., 60° C., and 65° C. In other embodiments, the temperature will be between about 25-65° C., about 30-65° C., about 35-65° C., about 40-65° C., and about 45-65° C. In other embodiments, the temperature will be between about 25-45° C., about 25-40° C. and about 30-35° C. In preferred embodiments, the starch substrate is never subjected to the thermal conditions used for liquefactions.

In some embodiments, a method encompassed by the invention will be conducted at a pH range of between pH 3.0 to 7.0; between pH 3.0 to 6.0, between pH 3.0 to 5.0, between 3.5 to 6.0, between pH 3.5 to 5.0, and between 3.5 to 4.5.

In some embodiments, the residence time of the method is from about 2 to 300 hrs, but more typically from 2 to 120 hours. In some embodiments, the process is conducted from about 5 to 100 hours. In other embodiments, the process is conducted from about 5 to 80 hours. In still other embodiments, the process is conducted for at least 5 hours but less than 100 hours. In other embodiments, the process is conducted for at least about 10 hours but less than about 100 hours.

In some embodiments, at least 60%, 65%, 70%, 75%, 80%, 85%, 90%, 94%, 95%, 96%, 97%, 98% and 99% of the dry solids of the granular starch is hydrolyzed. In some embodiments, the granular starch substrate is completely hydrolyzed. In some embodiments, at least 90% of the granular starch is hydrolyzed in 100 hours. In certain embodiments, at least 90% of the granular starch substrate is hydrolyzed in a time period of 24 hours. In other embodiments, at least 95% of the granular starch substrate is hydrolyzed in a time period of 24 hours.

The yield of glucose (percent of the total solubilized dry solids) may be at least about 85%, 90%, 91%, 92%, 93%, 94%, 95%, 96%, 97% and 98%. In some embodiments, the glucose may be used to produce high fructose syrups. In a preferred embodiment, the glucose is continually produced and substantially all of the glucose is used in the process to produce an end-product, such as ethanol and co-products such as DDGS. (Reference is made to MOLECULAR STRUCTURE AND FUNCTION OF FOOD CARBOHYDRATE, ED. G. G. BIRCH ET AL, APPLIED SCIENCE PUBLISHERS, LONDON). The glucose may also be used in a fermentation to produce other end products including but not limited to organic acids, enzymes, glycerol, amino acids, ascorbic acid intermediates, and other complex compounds, such as hormones and antibiotics.

EXPERIMENTAL

The following examples are provided in order to demonstrate and further illustrate certain preferred embodiments and aspects of the present invention and are not to be construed as limiting the scope thereof. Indeed, it is contemplated that these teachings will find use in further optimizing the process systems described herein.

In the disclosure and experimental section which follows, the following abbreviations apply:

asAA having GSH activity (an acid-stable alpha amylase having granular starch hydrolyzing activity); asaA (an acid-stable alpha amylase having granular starch hydrolyzing activity as illustrated in SEQ ID NO: 3 and which has been obtained from the endogenous expression of an asAA in *Aspergillus kawachi*); Tr-asaA (the expression of the *A. kawachi* acid-stable alpha amylase expressed in a *Trichoderma reesei* host); AkAA (the acid stable alpha amylase having SEQ ID NO: 3 and sometimes used interchangeability with asaA); GA (glucoamylase); HGA (a *Humicola* GA comprising the sequence of SEQ ID NO: 12); TrGA (is a *Trichoderma* GA comprising the sequence of SEQ ID NO: 11); wt % (weight percent); ° C. (degrees Centigrade); rpm (revolutions per minute); $H_2O$ (water); $dH_2O$ (deionized water); $dIH_2O$ (deionized water, Milli-Q filtration); aa (amino acid); bp (base pair); kb (kilobase pair); kD (kilodaltons); g or gm (grams); µg (micrograms); mg (milligrams); µL (microliters); ml and mL (milliliters); mm (millimeters); µm (micrometer); M (molar); mM (millimolar); µM (micromolar); U (units); V (volts); MW (molecular weight); sec (seconds); min(s) (minute/minutes); hr(s) (hour/hours); PAGE (polyacrylamide gel electrophoresis); DO (dissolved oxygen); phthalate buffer (sodium phthalate in water, 20 mM, pH 5.0); PBS (phosphate buffered saline [150 mM NaCl, 10 mM sodium phosphate buffer, pH 7.2]); SDS (sodium dodecyl sulfate); Tris (tris (hydroxymethyl)aminomethane); w/v (weight to volume); w/w (weight to weight); v/v (volume to volume); Genencor (Genencor International, Inc., Palo Alto, Calif.); DDGS (Distilleries Dry Grain plus Solids); MT (Metric ton); and EtOH (ethanol).

The following assays and methods are used in the examples provided below:

Glucoamylase Assay:

Glucoamylase activity was measured using a well-known assay which is based on the ability of glucoamylase to catalyze the hydrolysis of p-nitrophenyl-alpha-D-glucopyranoside (PNPG) to glucose and p-nitrophenol. At an alkaline pH, the nitrophenol; forms a yellow color that is proportional to glucoamylase activity and is monitored at 400 nm and compared against an enzyme standard measured as a GAU.

One "Glucoamylase Activity Unit" (GAU) is defined as the amount of enzyme that will produce 1 gm of reducing sugar, calculated as glucose per hour from a soluble starch substrate (4% ds) at pH 4.2 and 60° C.

The measurement of acid-stable alpha amylase activity is based on the degree of hydrolysis of soluble potato starch substrate (4% ds) by an aliquot of the enzyme sample at pH 4.5, 50° C. The reducing sugar content is measured using the DNS method as described in Miller, G. L. (1959) *Anal. Chem.* 31:426-428. One unit of the enzyme activity (SSU, soluble starch unit) is equivalent to the reducing power of 1 mg of glucose released per minute at the specific incubation conditions.

Determination of Total Starch Content:

The enzyme-enzyme starch liquefaction and saccharification process (dual enzyme method) was used to determine the total starch content. In a typical analysis, 2 g of the dry sample was taken in a 100 ml Kohlraucsh flask and 45 ml of MOPS buffer, pH 7.0 was added. The slurry was well stirred for 30 min. SPEZYME FRED (1:50 diluted in water), 1.0 ml was added and heated to boiling for 3-5 min. The flask was placed in an autoclave maintained at 121° C. for 15 min. After autoclaving the flask was placed in a water bath at 95° C. and 1 ml of 1:50 dilutes SPEZYME FRED was added and incubated for 45 min. The pH was adjusted to pH 4.2 and the temperature was reduced to 60° C. This was followed by addition of 20 ml acetate buffer, pH 4.2. Saccharification was carried out by adding 1.0 ml of 1:100 diluted OPTIDEX L-400 (Glucoamylase from Genencor International Inc.) and the incubation was continued for 18 hr at 60° C. The enzyme reaction was terminated by heating at 95° C. for 10 min. The total sugar composition was determined by HPLC analysis using glucose as a standard. The soluble starch hydrolysate from water extraction of a sample at room temperature without enzymatic treatment was subtracted from the total sugar.

Residual Starch Iodine Test:

A sample of the beer (fermentation broth) was centrifuged in 2 ml plastic centrifuge tubes. The supernatant was decanted and the tube containing the pellet was placed in an ice bath. Several drops of 0.025N iodine solution (0.1N iodine from VWR Cat. No. VW3207-1 diluted 4x) was added to the pellet and mixed. A positive (+) starch shows a range of color from blue to purple and the intensity of color is directly proportional to the concentration of starch. A negative result (−) remains yellowish.

Total Protein Analysis:

The total nitrogen (N) in the sample preparations was determined using the Kjeldhal method (American Assoc. Cereal Chemists (AACC), (1983), Methods 22B60 8th Ed. St Paul, Minn.). Protein content was calculated by 6.25× total N.

Ethanol and Carbohydrate Determinations:

Ethanol and carbohydrate composition of the samples were determined using the HPLC method as described herein:
a) 1.5 mL Eppendorf centrifuge tube was filled with fermenter beer and cooled
on ice for 10 min;
b) the sample tube was centrifuged for 1 min in Eppendorf table top centrifuge;
c) a 0.5 mL sample of the supernatant was transferred to a test tube containing
0.05 mL of Kill solution (1.1N $H_2SO_4$) and allowed to stand for 5 min;
d) 5.0 mL of water is added to the test tube sample and then filtered into a HPLC vial through 0.45 µm Nylon Syringe Filter; and
e) run on HPLC.
HPLC Conditions:
a) Ethanol System:
Column: Phenomenex Rezex Organic Acid Column (RHM-Monosaccharide) #00H-0132-KO (Equivalent to Bio-Rad 87H)
Column Temperature: 60° C.
Mobile Phase: 0.01 N $H_2SO_4$
Flow Rate: 0.6 mL/min Detector: RI
Injection Volume: 20 μL
b) Carbohydrate System:
Column: Phenomenex Rezex Carbohydrate (RCM-Monosaccharide) #00H-0130-KO (Equivalent to Bio-Rad 87H)
Column Temperature: 70° C.
Mobile Phase Nanopure DI $H_2O$
Flow Rate: 0.8 mL/min
Detector: RI
Injection Volume: 10 μL (3% DS material)

The column separates based on the molecular weight of the saccharides, which are designated as DP1 (monosaccharides); DP2 (disaccharides); DP3 (trisaccharides) and DP+4 (oligosaccharide sugars having a degree of polymerization greater than 3).

Preparation of asaA Used in Examples 7-16 was as Follows:

At the end of the fermentation of the *T. reesei* which expresses asaA (prepared according to examples 2 and 3), the biomass was separated by centrifugation and the clear culture filtrate was concentrated using a 10,000 molecular weight cut-off ultrafiltration membrane. This ultra filtrated concentrate having (90 SSU/g) was used.

Preparation of *Aspergillus niger* Glucoamylase Used in Examples 7-16 was as Follows:

A selected *Aspergillus niger* strain as described in U.S. Pat. No. 3,249,514 was used. After fermentation, fungal mycelia were separated using conventional separation methods including filtration and centrifugation. The clear filtrate was concentrated by ultrafiltration at 5° C. to a specified activity.

Example 1

Cloning the *Aspergillus kawachi* Acid-Stable Alpha-Amylase Gene

Genomic DNA was extracted from an overnight culture of *A. kawachi* mycelia. The FastDNA Kit (QbioGene, Carlsbad, Calif.) SPIN™ protocol was used according to the manufacturer's instructions for fungi. For homogenization, the sample was processed for 30 sec at speed 4.0 on a FastPrep Instrument. PCR primers were designed, based on the asaA sequence of A. Kaneko, et al. (Kaneko et al., (1996), *J. Ferm Bioeng* 81:292-298). The forward primer contained a motif for directional cloning into the pENTR/D vector (Invitrogen).

The sequence of the alpha6 primer was CACCATGAGAGTGTCGACTTCAAG (SEQ ID NO. 6) and the sequence of the Akaa3 primer was CTACCTCCACGTATCAACCAC (SEQ ID NO. 7).

Figure 4:
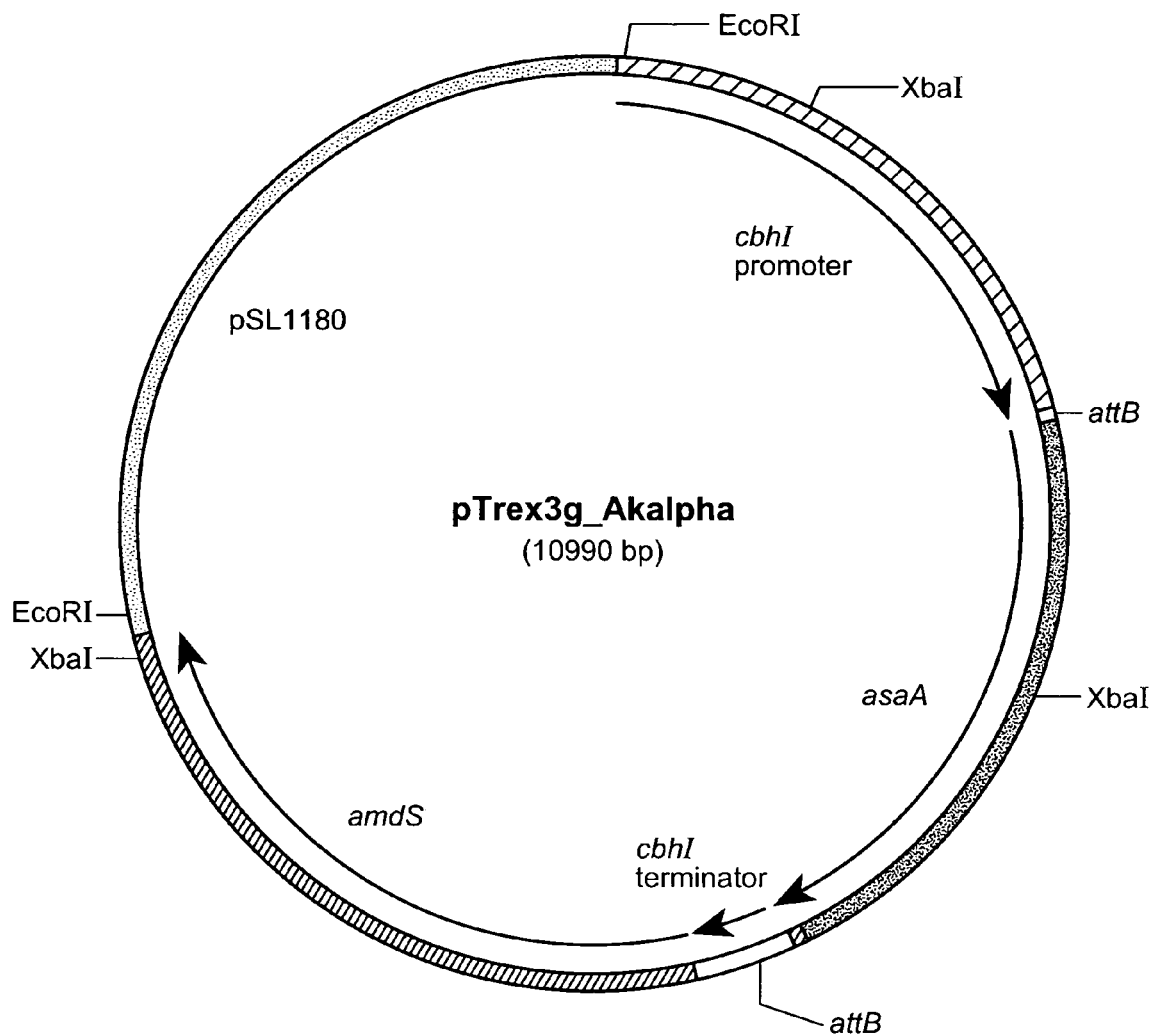
FIG. 4 provides a map of pTrex3g_Akalpha, which was used for expression of the nucleic acid encoding the AsaA (*Aspergillus kawachi* asAA) and which contains EcoRI sites flanking the fungal expression vector, wherein a. cbhI promoter is the *Trichoderma reesei* cellobiohydrolase promoter.

The 2.36 kb PCR product was purified by gel extraction (Gel Purification kit, Qiagen) and cloned into pENTR/D, according to the Invitrogen Gateway system protocol. The vector was then transformed into chemically competent Top10 *E. coli* (Invitrogen) with kanamycin selection. Plasmid DNA from several clones was digested with restriction enzymes to confirm the correct size insert. The alpha-amylase gene insert was sequenced (Sequetech, Mountain View, Calif.) from several clones (SEQ ID NO:1). Plasmid DNA from one clone, pENTR/D_Akaa#11, was added to the LR clonase reaction (Invitrogen Gateway system) with pTrex3g/amdS destination vector DNA. Recombination, in the LR clonase reaction, replaced the CmR and ccdB genes of the destination vector with the *A. kawachi* asaA from the pENTR/D vector. This recombination directionally inserted asaA between the cbhI promoter and terminator of the destination vector. Recombination site sequences of 48 and 50 bp remained upstream and downstream, respectively, of the alpha amylase. An aliquot of the LR clonase reaction was transformed into chemically competent Top10 *E. coli* and grown overnight with carbenicillin selection. Plasmid DNA from several clones was restriction digested to confirm the correct insert size. For removal of the fungal cassette from the bacterial plasmid, the Stratagene QuickChange protocol was followed to add an EcoRI site 3' to the amdS gene. The sequence of the entire fungal cassette was confirmed. Plasmid DNA from clone, pTrex3g_Akalpha#1 (FIG. 4) was digested with EcoRI to release the expression cassette including the cbhI promoter:asaA:cbhI terminator:amdS. This 7.8 kb cassette was purified by agarose extraction using standard techniques and transformed into a strain of *T. reesei* derived from the publicly available strain QM6a, as further described below.

Example 2

Biolistic Transformation of *T. reesei*

A *Trichoderma reesei* spore suspension was spread onto the center ~6 cm diameter of an MABA transformation plate (150 μl of a $5 \times 10^7$-$5 \times 10^8$ spore/ml suspension). The plate was then air dried in a biological hood. The stopping screens (BioRad 165-2336) and macrocarrier holders (BioRad 1652322) were soaked in 70% ethanol and air dried. DriRite desiccant was placed in small Petri dishes (6 cm Pyrex) and overlaid with Whatman filter paper. The macrocarrier holder containing the macrocarrier (BioRad 165-2335) was placed flatly on top of filter paper and the Petri dish lid replaced.

A tungsten particle suspension was prepared by adding 60 mg tungsten M-10 particles (microcarrier, 0.7 micron, Bio-Rad #1652266) to an Eppendorf tube. 1 ml ethanol (100%) was added. The tungsten was votexed in the ethanol solution and allowed to soak for 15 minutes. The Eppendorf tube was microfuged briefly at maximum speed to pellet the tungsten. The ethanol was decanted and washed three times with sterile distilled water. After the water wash was decanted the third time, the tungsten was resuspended in 1 ml of sterile 50% glycerol. The tungsten was prepared fresh at least every two weeks.

The transformation reaction was prepared by adding 25 μl of suspended tungsten to a 1.5 ml Eppendorf tube for each transformation. Subsequent additions were made in order, 0.5-5 μl DNA (XbaI-digested expression cassette), 25 μl 2.5M $CaCl_2$, 10 μl 0.1 M spermidine. The reaction was vortexed continuously for 5-10 minutes, keeping the tungsten suspended. The Eppendorf tube was then microfuged briefly and decanted. The tungsten pellet was washed with 200 μl of 70% ethanol, microfuged briefly to pellet and decanted. The pellet was washed with 200 μl of 100% ethanol, microfuged briefly to pellet, and decanted. The tungsten pellet was resuspended in 24 μl 100% ethanol. The Eppendorf tube was placed in an ultrasonic water bath for 15 seconds and 8 μl aliquots were transferred onto the center of the desiccated macrocarriers. The macrocarriers were left to dry in the desiccated Petri dishes.

A He tank was turned on to 1500 psi. 1100 psi rupture discs (BioRad 165-2329) were used in the Model PDS-1000/He Biolistic Particle Delivery System (BioRad). When the tungsten solution was dry, a stopping screen and the macrocarrier holder were inserted into the PDS-1000. An MABA plate, containing the target *T. reesei* spores, was placed 6 cm below the stopping screen. A vacuum of 29 inches Hg was pulled on the chamber and held. The He Biolistic Particle Delivery System was fired. The chamber was vented and the MABA plate removed for incubation at 28° C. until colonies appeared (5 days).

With reference to this Example 2 the following solutions were prepared,

|  | per liter |
|---|---|
| Modified amdS Biolistic agar (MABA) Part I, make in 500 ml dH$_2$O | |
| 1000x salts | 1 ml |
| Noble agar | 20 g |
| pH to 6.0, autoclave Part II, make in 500 ml dH$_2$O | |
| Acetamide | 0.6 g |
| CsCl | 1.68 g |
| Glucose | 20 g |
| KH$_2$PO$_4$ | 15 g |
| MgSO$_4$·7H$_2$O | 0.6 g |
| CaCl$_2$·2H$_2$O | 0.6 g |
| pH to 4.5, 0.2 micron filter sterilize; leave in 50° C. oven to warm, add to agar, mix, pour plates. Stored at room temperature. | |
| 1000x Salts | |
| FeSO$_4$·7H$_2$O | 5 g |
| MnSO$_4$·H$_2$O | 1.6 g |
| ZnSO$_4$·7H$_2$O | 1.4 g |
| CoCl$_2$·6H$_2$O | 1 g |

Bring up to 1 L dH$_2$O.
0.2 micron filter sterilize

Example 3

PEG-Mediated Protoplast Fusion Transformation of *T. reesei*

A 1-2 cm$^2$ agar plug of a sporulated mycelia (grown on potato dextrose agar (PDA), Difco for 5 days at 30° C.) was inoculated into 50 ml of YEG (5 g/L yeast extract plus 20 g/L glucose) broth in a 250 ml, 4-baffle shake flask and incubated at 30-37° C. for 16-20 hours at 200 rpm. The mycelia were recovered by transferring the shake flask contents into 50 ml conical tubes and spinning at 2500 rpm for 10 minutes. The supernatant was discarded and the mycelial pellet was transferred into a 250 ml, 0.22 m CA or PES Corning filter bottle containing 40 ml of filtered β-D-glucanase solution. The solution was incubated at 30° C., 200 rpm, for 2 hours to generate protoplasts. Protoplasts were harvested by filtration, through sterile Miracloth (CalBiochem, La Jolla, Calif.), into a 50 ml conical tube. The protoplasts were pelleted by centrifugation at 2000 rpm for 5 minutes and the supernatant discarded. Protoplast pellets were washed once with 50 ml of 1.2 M sorbitol; centrifuged (2000 rpm, 5 min.) and supernatant was discarded. The pellet was washed with 25 ml of sorbitol/CaCl$_2$. A haemocytometer was used to count the protoplasts and then pelleted by centrifugation at 2000 rpm for 5 min. The supernatant was discarded and protoplast pellets resuspended in a volume of sorbitol/CaCl$_2$ sufficient to generate a protoplast solution with a protoplast concentration of 1.25×10$^8$/ml.

For each transformation, an aliquot of 20 μg of expression vector DNA (in a volume no greater than 20 μl) was transferred into 15 ml conical tubes, on ice. Protoplast suspension (200 μl) and 50 μl PEG solution was added to each tube. This was mixed gently and incubated on ice for 20 min. PEG (2 ml) solution was added to each transformation tube and incubated at room temperature for 5 minutes. 4 ml sorbitol/CaCl$_2$ solution was added to each tube (total volume 6.2 ml) and mixed gently. Then 2 ml of the transformation mixture was added to each of 3 molten (50° C.) top agar tubes. Each top agar mixture was poured onto a separate transformation plate and incubated at 30° C. for four to seven days.

For transformation with amdS selection, acetamide/sorbitol plates and top agar were used. Selection plates were the same as transformation plates, but without sorbitol. Putative transformants were purified by transferring isolated colonies to fresh selective media containing acetamide.

Media and solutions were prepared as follows.
1) 40 ml β-D-glucanase solution—dissolved 600 mg β-D-glucanase (InterSpex Products Inc., San Mateo, Calif.) and 400 mg MgSO$_4$.7H$_2$O in 40 ml 1.2M sorbitol.
2) 200 ml PEG mix—Dissolved 50 g PEG 4000 (BDH Laboratory Supplies Poole, England) and 1.47 g CaCl$_2$.2H$_2$O in 200 ml dIH$_2$O. Prepared fresh monthly.
3) Sorbitol/CaCl$_2$ solution—Dissolved 50 mM CaCl$_2$ in 1.2M sorbitol.
4) Acetamide/sorbitol agar—
   Part 1—Dissolved 0.6 g acetamide (Aldrich, 99% sublime), 1.68 g CsCl, 20 g glucose, 20 g KH$_2$PO$_4$, 0.6 g MgSO$_4$.7H$_2$O, 0.6 g CaCl$_2$.2H$_2$O, 1 ml 1000× salts (see below) in 200 ml dIH$_2$O, adjusted to pH 5.5, brought volume up to 300 mls with dH$_2$O, and filter sterilized.
   Part II—20 g Noble agar and 218 g sorbitol were added to a 1 L cylinder, brought to volume (700 mls) with dIH$_2$O, and autoclaved.
   Part II was added to Part I for a final volume of 1 L.
5) 1000× Salts—Combined 5 g FeSO$_4$.7H$_2$O, 1.6 g MnSO$_4$.H$_2$O, 1.4 g ZnSO$_4$.7H$_2$O, 1 g CoCl$_2$.6H$_2$O and brought the volume up to 1 L with dIH$_2$O. Filter sterilized.

Example 4

PEG-Mediated Protoplast Fusion Transformation of *Aspergillus niger*

A 2 cm$^2$ agar plug was inoculated from a sporulated *A. niger* plate, into 50 ml of YEG (5 g/L yeast extract plus 20 g/L glucose) broth in a 250 ml, 4-baffle shake flask. The agar plug was incubated at 30°-37° C. for 16-20 hours at 200 rpm, mycelia was harvested through a sterile Miracloth filter and washed with Solution A. Washed mycelia was aseptically transferred into 40 ml of protoplasting solution and incubated at 30° C., 200 rpm, for 1-2 hours, protoplasting progress was monitored microscopically. The protoplasting reaction was filtered through sterile Miracloth, into two 50 ml sterile disposable centrifuge tubes and the volume brought up to 45 mls each with Solution B. The protoplasts were centrifuged at 2500 rpm for 5 minutes to obtain pellets and the supernatant was discarded. The pellet was washed twice more with 20 ml volumes of Solution B. The pellet was resuspended in 10 ml Solution B and protoplasts counted using a haemocytometer. Protoplasts were again centrifuged and the supernatant discarded. Protoplasts were resuspended, in Solution B to yield ~1×10$^7$/100 μl. On ice, 100 μl protoplast solution was added to pre-chilled 15 ml tubes, one tube per transformation. 10 μg DNA was added in a volume not exceeding 10 μl. Solution C (12.5 μl) was added, mixed gently, and incubated on ice for 20 minutes.

MMS top agar (3 tubes of 10 ml each, per transformation) was melted and maintained at 55° C. Protoplasts were removed from the ice and Solution C (1 ml) and Solution B (2 ml) were added to each tube and the tubes were mixed gently. 1 ml of the protoplast mixture was added to each of the 3 top agar tubes and the top agar was poured onto MMS plates. This was repeated for each transformation and plates were incubated for 4-7 days at 30° C.

Solution A (per 500 ml)—0.44 g $K_2HPO_4$; 0.34 g $KH_2PO_4$; 48.156 g anhydrous $MgSO_4$ (FW 120.37); and $dIH_2O$ added for a final volume of 500 ml, pH 5.5. Filter sterilized and store at room temperature.

Protoplasting solution—Dissolved 180 units beta-D-glucanase (InterSpex Products, Inc) in 40 ml Solution A. Filter sterilized, 0.2 micron.

Solution B (per 500 ml)—5 ml 1M Tris, pH 7.5; 2.77 g $CaCl_2$ (FW 110.99); 109.32 g Sorbitol (FW 182.2; 1.2M); and $dIH_2O$ added for a final volume of 500 ml. Filter sterilized and store at room temperature.

Solution C (per 500 ml)—250 g PEG 4000; 2.77 g $CaCl_2$; 5 ml 1M Tris, pH 7.5; and $dIH_2O$ added for a final volume of 500 ml. Filter sterilized.

MMS Agar*—Dissolved in 1 L $dIH_2O$, 6 g/L $NaNO_3$; 0.52 g/L KCl; 1.52 g/L $KH_2PO_4$; 218.5 g/L D-Sorbitol; 1 ml/L Trace elements (see below); 10 g/L agar (low melt agarose in the top agar).

*For amdS selection, replace the nitrate in the MMS with 0.59 g/L acetamide and 3.4 g/L CsCl.

Autoclave. Post-sterilization, aseptically added 10 ml 50% glucose and 1.25 ml 20% $MgSO_4.7H_2O$.

Trace Elements Solution

Dissolve in 250 ml $dIH_2O$, 1 g/L $FeSO_4.7H_2O$ 8.8 g/L $ZnSO_4.7H_2O$ 0.4 g/L $CuSO_4.5H_2O$ 0.15 g/L $MnSO_4.4H_2O$ 0.1 g/L $Na_2B_4O_7.10H_2O$ 50 mg/L $(NH_4)6Mo_7O_{24}.4H_2O$ Mix and added 0.2 ml concentrated HCl to dissolve. Brought volume up to 1 L with $dIH_2O$. Filter sterilized.

Example 5

Fermentation of *T. reesei* Transformed with the asaA Gene and Assay of Activity in *T. reesei* Clones In general, the fermentation protocol as described in Foreman et al. (Foreman et al. (2003) *J. Biol. Chem.* 278:31988-31997) was followed. More specifically, duplicate fermentations were run for each of the strains displayed in FIG. 5A. 0.8 L of Vogels minimal medium (Davis et al., (1970) METHODS IN ENZYMOLOGY 17A, pg 79-143 and Davis, Rowland, NEUROSPORA, CONTRIBUTIONS OF A MODEL ORGANISM, Oxford University Press, (2000)) containing 5% glucose was inoculated with 1.5 ml frozen spore suspension. After 48 hours, each culture was transferred to 6.2 L of the same medium in a 14 L Biolafitte fermenter. The fermenter was run at 25° C., 750 RPM and 8 standard liters per minute airflow. One hour after the initial glucose was exhausted, a 25% (w/w) lactose feed was started and fed in a carbon limiting fashion to prevent lactose accumulation. The concentrations of glucose and lactose were monitored using a glucose oxidase assay kit or a glucose hexokinase assay kit with beta-galactosidase added to cleave lactose, respectively (Instrumentation Laboratory Co., Lexington, Mass.).

Samples were obtained at regular intervals to monitor the progress of the fermentation. Collected samples were spun in a 50 ml centrifuge tube at ¾ speed in an International Equipment Company (Needham Heights, Mass.) clinical centrifuge. Sample supernatants were run of 4-12% BIS-TRIS SDS-PAGE gels, under reducing conditions with MOPS (morpholinepropanesulfonic acid) SDS running buffer and LDS sample buffer (FIG. 5A).

In additional fermentations, sample supernatants were run as basically described above. However, different proportions of intact and truncated forms of Tr-asaA were obtained. FIG. 5B, lane 2 illustrates three major bands between 50 and 90 kD. The three bands from the gel digested using modified methods known in the art (Hellman et al., (1995) *Anal. Biochem.* 224:451-455). Peptides were extracted, separated using reverse phase HPLC and peptide mass and ms/ms fragmentation patterns determined. The resulting peptide maps confirmed that both lower MW bands were truncated. One band represented a truncated asAA in which clipping occurred between amino acid position 434 and 580 of SEQ ID NO: 3 and the second band represented a truncated asAA in which clipping took place at about amino acid position 581 of SEQ ID NO: 3. Each band exhibited alpha amylase and GSH starch hydrolyzing activity.

Example 6

Comparison of pH Stability of Native and Recombinant *A. kawachi* Acid-Stable Alpha Amylase Having GSH Activity (asaA)

Samples of recombinantly produced asaA (Tr-asaA) as described above and samples of native asaA were diluted to equal protein concentrations with 20 mM acetate buffer at pH 4.5. Reactions were run in 100 mM citrate/NaOH buffers at 50° C. for 30 minutes at pH levels 3 to 7. 1.0 mL of the reaction was added to 5 mL of 10% corn starch (Cargill Foods, MN) in 100 mM acetate, pH 4.5 in sample tubes. The tubes were shaken at 50° C. for 20 minutes. Then 0.5 mL 2.0% NaOH was added. Tubes were spun and 0.5 mL of the supernatant were assayed for reducing sugars using the Dinito Salicylic Acid (DNS) Assay (Goto et al., (1994) supra). The results are depicted in FIG. 6. The r-asaA exhibited 100% residual activity at pH 3.9. In comparison the n-asaA exhibited 100% residual activity at pH 4.5.

Example 7

Effect of Tr-asaA Concentrations During Simultaneous Saccharification and Fermentation (SSF) of Non-Cooked Whole Ground Corn Substrate Tr-asaA was evaluated at two levels of glucoamylase (GA) from a cell free culture filtrate (0.5 and 1.0 GAU/g). Thirty six percent corn flour slurry was prepared containing dry corn steep (2.5% of corn flour). The pH of the slurry was adjusted to 4.8 with dilute sulfuric acid. The total dry solids of the slurry were 33.85%. Fermentations were carried out in 125 ml flasks containing 100 gm of mash (slurry). The desired levels of enzymes were added then 3 ml of propagated yeast slurry was added to start the fermentation. The yeast inoculum was prepared by adding 0.26 gm of dry Fali yeast to 100 gm of mash containing GA activity at 0.9 GAU/g of raw material solids. This slurry was placed in a 32° C. water bath and gently mixed for about 17 hours. At various time intervals samples of the fermentation (beer) were taken for HPLC analysis. After 72 hours, the fermentations were terminated and the beer was dried at 60° C. to obtain the distillers dry grains plus soulubles (DDGS).

The starch content of the DDGS was determined and the insoluble solids of the beer after terminating the fermentation were spot checked for starch by the addition of Iodine. The enzymes used in this study were *A. niger* GA. Table 1 summarizes ethanol levels, iodine stain of the mash solids and % starch of the DDGS. The results as illustrated in Table 1 demonstrate Tr-asaA enhanced the hydrolysis of granular corn starch by glucoamylase.

TABLE 1

Effect of asaA During Conversion of Granular Corn Starch to Ethanol under Yeast Fermentation Conditions

| GA GAU/g ds | asaA SSU/g ds | % v/v EtOH 24 hr | % v/v EtOH 50 hr | % v/v EtOH 72 hr | % starch DDGS | Iodine |
|---|---|---|---|---|---|---|
| 0.5 |  | 7.7 | 11.4 | 13.7 | 27.4 | + |
| 0.5 | 0.25 | 9.2 | 14.7 | 16.9 | 7.7 | + |
| 0.5 | 0.50 | 9.6 | 15.4 | 17.0 | 5.7 | +/− |
| 0.5 | 1.0 | 10.0 | 16.2 | 17.3 | 4.1 | +/−− |
| 0.5 | 2.0 | 10.9 | 16.5 | 17.5 | 2.8 | − |
| 0.5 | 3.0 | 11.2 | 16.8 | 17.5 | 1.6 | − |
| 0.5 | 4.0 | 11.2 | 16.9 | 17.4 | 1.7 | − |
| 0.5 | 5.0 | 11.2 | 17.0 | 17.7 | 1.5 | − |
| 1.0 |  | 9.3 | 14.4 | 16.2 | 13.0 | + |
| 1.0 | 0.25 | 11.6 | 17.1 | 17.8 | 3.6 | +/−− |
| 1.0 | 0.5 | 12.1 | 16.8 | 17.9 | 2.6 | − |
| 1.0 | 1.0 | 12.7 | 17.2 | 17.7 | 2.2 | − |
| 1.0 | 2.0 | 12.7 | 17.6 | 17.8 | 1.6 | − |
| 1.0 | 3.0 | 12.9 | 17.5 | 17.8 | 1.1 | − |
| 1.0 | 4.0 | 13.2 | 17.5 | 17.9 | 0.8 | − |
| 1.0 | 5.0 | 13.3 | 17.2 | 17.9 | 1.1 | − |
| 2.0 |  | 11.2 | 15.5 | 16.9 | 9.6 | + |
| 3.0 |  | 11.4 | 15.9 | 17.2 | 5.8 | + |

Example 8

Conversion of Granular Starch Substrates by Glucoamylase and Alpha Amylases

Commercial alpha amylases from different sources were compared with Tr-asaA under the simultaneous saccharification and fermentation conditions in the presence of glucoamylase at 0.5 GAU/g of ds. The activity of the commercial alpha amylases was determined using the soluble starch substrate (SSU) method assay as described earlier.

TABLE 2

| Alpha Amylase | Microbial Strain | SSU/ml |
|---|---|---|
| Tr-asaA | *A. kawachi* asAA expressed in *T. reesei* | 90 |
| SPEZYME LT AA | *Bacillus amyloliquefaciens* | 2,759 |
| SPEZYME FRED | *Bacillus licheniformis*** | 4,842 |
| SPEZYME Ethyl | *Bacillus stearothermophilus*** | 22,082 |
| CLARASE L | *Aspergillus oryzae* | 23,087 |

**denotes a recombinant strain

Ethanol fermentation was carried out using whole ground corn as described in Example 7. Alpha amylases from the sources listed in Table 2 were added at 1.0 SSU/gram of ground corn and glucoamylase at 0.5 GAU/g. The samples were taken during the course of the fermentation and analyzed for ethanol content (FIG. 7). After the fermentation, the insoluble solids (DDGS) were separated and the residual starch content of the corn mash at pH 5.0 was determined. The results are summarized in Table 3.

TABLE 3

| | | Ave % v/v EtOH | | | |
|---|---|---|---|---|---|
| GAU/g ds | Alpha Amylase at (1.0 SSU/g ds) | 22 hr | 46 hr | 72 hr | Residual % starch in DDGS 72 hr |
| 0.5 | — | 7.77 | 11.56 | 14.44 | 29.8 |
| 0.5 | SPEZYME LT-AA | 7.72 | 11.56 | 14.78 | 30.8 |
| 0.5 | SPEZYME FRED | 7.84 | 11.77 | 14.59 | 30.8 |
| 0.5 | SPEZYME Ethyl | 7.94 | 11.82 | 14.57 | 29.1 |
| 0.5 | CLARASE L | 7.94 | 11.72 | 14.62 | 30.8 |
| 0.5 | Tr-asaA | 9.57 | 15.75 | 18.44 | 9.0 |

The results in Table 3 clearly show that Tr-asaA is very effective in aiding glucoamylase to hydrolyze granular starch under the ethanol fermentation conditions using yeast. Additionally, as observed from the table, % ethanol produced in the fermentation (18.44) is greater and % residual starch in DDGS (9.0) is significantly lower using the enzyme combination of the present invention.

Example 9

Evaluation of Whole Ground Wheat in the Ethanol Fermentation Using Tr-asaA

To a 36% slurry of whole ground wheat, dry corn steep liquor was added at 2.5% based on the weight of the whole ground wheat. The fermentations were carried out in 125 ml flasks containing 100 gm of mash. The pH of the slurry was adjusted to 4.8 with dilute sulfuric acid. The mash was diluted to a final concentration of 33.85% ds.

Glucoamylase (0.5 GAU/g ground wheat) and asaA (1.0 SSU/g whole ground wheat) were added to the mash. This was followed by adding 3.0 ml of propagated yeast to start the fermentation. Yeast inoculum was prepared by adding 0.26 gm of dry Fali yeast to 100 gm of mash. The fermentations were run in a 32° C. water bath while gently stirred. At various time intervals samples of the fermentation broth (beer) were taken, centrifuged for HPLC analysis of sugar composition and ethanol (Table 4)

TABLE 4

Whole ground wheat granular starch in the yeast fermentation for ethanol production

| GA GAU/g ds | Tr-asaA SSU/g ds | Hrs | % w/v DP > 2 | % w/v DP-2 | % w/v DP-1 | % w/v Lactic | % w/v Glycerol | % v/v Ethanol |
|---|---|---|---|---|---|---|---|---|
|  |  | 0 | 0.98 | 0.97 | 2.00 | 0.22 | 0.12 | 0.00 |
| 0 | 0 | 24 | 1.33 | 0.00 | 0.02 | 1.09 | 0.15 | 2.42 |
| 0 | 0 | 48 | 1.17 | 0.00 | 0.00 | 1.39 | 0.13 | 2.38 |
| 0 | 0 | 72 | 1.08 | 0.00 | 0.01 | 1.38 | 0.13 | 2.16 |
| 0 | 0.1 | 24 | 1.30 | 0.00 | 0.02 | 1.06 | 0.16 | 4.49 |

TABLE 4-continued

Whole ground wheat granular starch in the yeast fermentation for ethanol production

| GA GAU/g ds | Tr-asaA SSU/g ds | Hrs | % w/v DP > 2 | % w/v DP-2 | % w/v DP-1 | % w/v Lactic | % w/v Glycerol | % v/v Ethanol |
|---|---|---|---|---|---|---|---|---|
| 0 | 0.1 | 48 | 1.16 | 0.00 | 0.02 | 1.51 | 0.16 | 2.28 |
| 0 | 0.1 | 72 | 1.23 | 0.00 | 0.01 | 1.83 | 0.15 | 2.91 |
| 0 | 0.25 | 24 | 1.28 | 0.03 | 0.02 | 1.06 | 0.17 | 2.94 |
| 0 | 0.25 | 48 | 1.05 | 0.00 | 0.02 | 1.41 | 0.15 | 2.73 |
| 0 | 0.25 | 72 | 1.24 | 0.00 | 0.03 | 1.92 | 0.17 | 3.06 |
| 0 | 0.5 | 24 | 1.25 | 0.00 | 0.01 | 1.02 | 0.13 | 3.03 |
| 0 | 0.5 | 48 | 1.22 | 0.00 | 0.02 | 1.60 | 0.18 | 3.27 |
| 0 | 0.5 | 72 | 1.26 | 0.00 | 0.03 | 1.90 | 0.18 | 3.24 |
| 0 | 0.75 | 24 | 1.29 | 0.03 | 0.02 | 1.06 | 0.16 | 3.21 |
| 0 | 0.75 | 48 | 1.29 | 0.00 | 0.03 | 1.62 | 0.10 | 3.57 |
| 0 | 0.75 | 72 | 1.34 | 0.00 | 0.03 | 1.90 | 0.18 | 3.60 |
| 0 | 1.0 | 24 | 1.29 | 0.04 | 0.02 | 1.04 | 0.16 | 3.43 |
| 0 | 1.0 | 48 | 1.32 | 0.04 | 0.01 | 1.55 | 0.18 | 4.02 |
| 0 | 1.0 | 72 | 1.46 | 0.09 | 0.04 | 1.84 | 1.21 | 4.15 |
| 0.2 | 0 | 24 | 1.18 | 0.00 | 0.00 | 1.04 | 0.18 | 3.34 |
| 0.2 | 0 | 48 | 1.16 | 0.00 | 0.02 | 1.67 | 0.19 | 4.14 |
| 0.2 | 0 | 72 | 1.16 | 0.00 | 0.02 | 1.92 | 0.19 | 4.78 |
| 0.2 | 0.1 | 24 | 1.20 | 0.00 | 0.03 | 1.05 | 0.20 | 3.64 |
| 0.2 | 0.1 | 48 | 1.12 | 0.00 | 0.02 | 1.59 | 0.20 | 4.60 |
| 0.2 | 0.1 | 72 | 1.14 | 0.00 | 0.03 | 1.86 | 0.21 | 5.58 |
| 0.2 | 0.25 | 24 | 1.16 | 0.00 | 0.03 | 1.02 | 0.21 | 3.80 |
| 0.2 | 0.25 | 48 | 1.14 | 0.00 | 0.03 | 1.57 | 0.22 | 5.13 |
| 0.2 | 0.25 | 72 | 1.06 | 0.03 | 0.03 | 1.71 | 0.21 | 5.90 |
| 0.2 | 0.5 | 24 | 1.20 | 0.00 | 0.03 | 1.03 | 0.22 | 4.04 |
| 0.2 | 0.5 | 48 | 1.14 | 0.00 | 0.01 | 1.54 | 0.22 | 5.61 |
| 0.2 | 0.5 | 72 | 1.13 | 0.03 | 0.04 | 1.74 | 0.23 | 6.65 |
| 0.2 | 0.75 | 24 | 1.16 | 0.00 | 0.03 | 1.03 | 0.22 | 4.13 |
| 0.2 | 0.75 | 48 | 1.24 | 0.00 | 0.04 | 1.54 | 0.24 | 5.68 |
| 0.2 | 0.75 | 72 | 1.10 | 0.00 | 0.01 | 1.63 | 0.23 | 7.14 |
| 0.2 | 1.0 | 24 | 1.00 | 0.00 | 0.03 | 0.96 | 0.17 | 4.14 |
| 0.2 | 1.0 | 48 | 1.16 | 0.00 | 0.04 | 1.50 | 0.25 | 5.90 |
| 0.2 | 1.0 | 72 | 1.21 | 0.03 | 0.04 | 1.68 | 0.23 | 6.76 |
| 0.5 | 0 | 24 | 1.07 | 0.00 | 0.03 | 0.98 | 0.24 | 4.50 |
| 0.5 | 0 | 48 | 1.01 | 0.00 | 0.02 | 1.41 | 0.25 | 6.29 |
| 0.5 | 0 | 72 | 1.10 | 0.03 | 0.15 | 1.55 | 0.25 | 7.49 |
| 0.5 | 0.1 | 24 | 1.12 | 0.00 | 0.04 | 0.94 | 0.24 | 4.62 |
| 0.5 | 0.1 | 48 | 1.12 | 0.00 | 0.03 | 1.34 | 0.27 | 6.92 |
| 0.5 | 0.1 | 72 | 1.09 | 0.03 | 0.03 | 1.46 | 0.27 | 8.45 |
| 0.5 | 0.25 | 24 | 1.17 | 0.00 | 0.05 | 0.97 | 0.27 | 5.01 |
| 0.5 | 0.25 | 48 | 1.20 | 0.00 | 0.04 | 1.28 | 0.28 | 7.18 |
| 0.5 | 0.25 | 72 | 1.06 | 0.03 | 0.03 | 1.34 | 0.27 | 8.78 |
| 0.5 | 0.5 | 24 | 1.16 | 0.00 | 0.05 | 0.91 | 0.26 | 5.29 |
| 0.5 | 0.5 | 48 | 1.11 | 0.00 | 0.04 | 1.18 | 0.28 | 7.71 |
| 0.5 | 0.5 | 72 | 1.07 | 0.03 | 0.04 | 1.23 | 0.28 | 9.47 |
| 0.5 | 0.75 | 24 | 1.15 | 0.00 | 0.05 | 0.90 | 0.28 | 5.33 |
| 0.5 | 0.75 | 48 | 1.11 | 0.03 | 0.06 | 1.16 | 0.30 | 8.08 |
| 0.5 | 0.75 | 72 | 1.06 | 0.04 | 0.05 | 1.17 | 0.30 | 9.91 |
| 0.5 | 1.0 | 24 | 1.12 | 0.00 | 0.06 | 0.89 | 0.29 | 5.52 |
| 0.5 | 1.0 | 48 | 1.12 | 0.00 | 0.05 | 1.14 | 0.32 | 8.39 |

Example 10

Effect of Substrate Treatment on the Ethanol Yield and Composition of Distilleries Dry Grain Solids, (DDGS)

Whole ground corn substrate was subjected to a conventional dry milling process for fuel alcohol fermentation using a hammer mill to reduce particle size. Three different mashes were prepared.

Treatment 1 (Trt 1) is a high temperature treatment, which involved a batch liquefaction of a 36% ds corn flour slurry containing 0.9% dry corn steep (DCS) with 3.5 U/g SPEZYME ETHYL at pH 5.6 by jet cooking according to the prior art procedures. The slurry was place in a 90° C. bath for 1.5 hours, mixed and then cooled to 30° C. with a pH adjustment to 5.0 with dilute sulfuric acid. The slurry was further diluted with water to 32.71% ds.

Treatment 2 (Trt 2) is a low temperature treatment. The mash was prepared by incubating a 36% corn flour slurry containing 0.9% DCS with the pH adjusted to 5.0 with dilute sulfuric acid at 60° C. for three hours. Prior to incubation 0.05 GAU/g of glucoamylase was added.

Treatment 3 (Trt 3) is a room temperature treatment—a corn slurry was obtained at room temperature prior to use in the fermentation with 0.5 GAU glucoamylase/g of corn and 1.0 SSU/g corn of Tr-asaA.

Yeast fermentation was then carried out on each treatment as described in example 7.

After the fermentation, ethanol yield was determined and the insoluble solids from each treatment were separated by centrifugation, dried at 60° C. and the total carbohydrate content and nitrogen content were determined. The results are illustrated in Table 5, wherein Trt 3 is a process encompassed by the invention.

TABLE 5

Comparison of ethanol yield and the composition of DDGS of different treatments of whole ground corn substrate under ethanol fermentation using yeast

| Corn Mash Treatment | Kgs DDGS/ MT corn | % Residual starch content in DDGS | % Total Protein in DDGS | Ethanol L/MT corn |
|---|---|---|---|---|
| Trt 1 High Temperature | 326 | 4.8 | 27.5 | 402 |
| Trt 2 Low Temperature | 299 | 3.8 | 29.5 | 429 |
| Trt 3 No heat treatment GA + Tr-asaA | 274 | 3.5 | 31.6 | 438 |

As observed from the results illustrated in Table 5, the % residual starch in DDGS treated according to the process of the present invention (Trt 3) was less than the % residual starch obtained from the prior art treatment (Trt 1) or the low temperature treatment (Trt 2). The values were 3.5% (Trt 3) as opposed to 4.8% or 3.8% for Trt1 and Trt 2. The total protein content of the DDGS and the amount of ethanol produced was higher from Trt 3 according to the invention as compared to the prior art treatment (Trt 1).

Example 11

Incubation of Granular Corn Starch with Purified *Aspergillus kawachi* Alpha Amylase and Purified *Aspergillus niger* Glucoamylase Enzyme Purification:

*Aspergillus niger* glucoamylase (GA) and *Aspergillus kawachi* alpha amylase (AkAA) were both purified from culture filtrate using a preparative high pressure liquid chromatographic (HPLC) method using an AKTA (Amersham Pharmacia, Biotech., NJ). In a typical experiment, both crude enzyme samples were desalted with 10 mM MES buffer (pH 5.75) to bring down the conductivity using a spin column (Bio-Rad, CA). The samples were brought up to 2M $NH_4SO_2$. The sample was loaded on to a Q-Sepharose column (Amersham, Biosciences, NJ) and eluted with 20 mM MES buffer (pH 5.75) using a gradient of 1.5 M KCl. The fractions with corresponding activity were pooled together and concentrated for further experiments.

Incubation with Granular Corn Starch with Purified Enzymes:

The purified enzyme preparations were added to a 4.0% granular corn starch (Cargill, Minneapolis, Minn.) in 0.1 M acetate buffer (pH 4.5) as follows for Scanning Electron Microscopic (SEM) analysis.

Purified GA at 0.5 GAU/g corn starch; purified AkAA at 1.0 SSU/g starch; and GA and AkAA combined were incubated at 32° C. with gentle stirring. Aliquot samples (0.75 ml) were taken at intervals of 2, 4 and 8 hours, centrifuged and the soluble sugar determined by the method described in the examples above. The pellet was resuspended in distilled water (5 ml) and centrifuged. The pellet was suspended again in 5 ml of absolute ethanol (99%), stirred for uniform mixing and centrifuged. The alcohol treated pellet was air-dried in the tube and used for SEM analysis.

SEM Analysis:

Approximately 200 µl dry volume was transferred to a 1.5 ml Ependorf tube and 0.8 ml absolute ethanol was added. The components were vortexed to make a suspension of starch particles. A few drops of suspension was placed on a freshly cleaned glass cover slip and allowed to air dry. The cover slip was mounted on specimen stubs with carbon adhesive tabs, painted around the circumference with colloidal silver adhesive (Electron Microscopy Sciences, Ft. Washington, Pa.) and coated with a thin layer of gold in a ScanCoat Six Sputter Coater (Edwards High Vacuum Intl. Crawley, UK). Scanning electron microscopy was done at 5 kv in the secondary electron imaging mode using a Quanta 200 FEG scanning electron microscope (FEI Inc., Hillsboro, Oreg.) at instrumental magnification of 1,000 and 5,000×. Eight to ten images were made from different areas on each sample stub. The effect of individual and combined enzyme treatments on the granular corn starch is illustrated in FIGS. 8 and 9.

Hydrolysis and Microscopic Examination:

Reducing sugar (mg/ml reducing equivalents), measured as glucose released after 4 hours as a result of granular starch hydrolysis by AkAA and GA is illustrated in FIG. 8. Degradation of granular starch with glucoamylase alone was 4.9 mg/ml; degradation of granular starch with AkAA alone was only 0.3 mg/ml. However, degradation of granular starch with the combination of GA and AkAA was 12.1 mg/ml. The degradation value for the enzymes combined illustrates a synergistic interaction, which is significantly greater than the additive value of the enzymes.

The starch granules treated as described in this example were observed with a scanning electron microscope. As shown in FIG. 9, corn starch granules incubated with purified AkAA did show minor surface modification. These were observed as small pin prick holes. Corn starch granules incubated with purified GA showed many small defined deep holes. Significantly, corn starch granules incubated with the combination of GA and AkAA showed numerous wide and deep penetrating cavities. Additionally, surface erosion, which exposed the layered structure of the granular center, was observed in the granules incubated with the combination of GA and AkAA.

Example 12

Effect of % Dry Solids Content (ds) of a Granular Corn Starch Slurry on Ethanol Yield Corn flour was slurried with water to obtain a 36% ds mash. A small amount of corn steep (0.2% of the slurry) was added along with 400 ppm (0.04%) urea to the mash prior to adjusting the pH to 4.5 with sulfuric acid. The dry solids content of the slurry was adjusted from 20 to 36% ds. The fermentations were carried out in 125 ml flasks containing a total of 100 g mash. The enzymes were diluted so that a constant volume of 0.5 ml was used for each enzyme. Each flask was inoculated with 3 ml of yeast that was propagated 17 hours prior to use. The yeast propagation procedure involved adding 0.5% dry Fali yeast to 25% ds mash containing 0.5 GAU/g of GA and 1.5 SSU/g AkAA and incubating while gently mixing in a 32° C. water bath. At approximately 24 hour time intervals samples of beer were dried at 60° C. to obtain DDGS.

TABLE 6

Effect of DS Content on the Ethanol Production and Residual Starch in DDGS at 75 hours

| | GA (0.5 GAU/g ds) | | AkAA (1.5 SSU/g ds) + GA (0.5 GAU/g ds) | |
|---|---|---|---|---|
| % DS | % v/v EtOH | DDGS % residual starch | % v/v EtOH | DDGS % residual starch |
| 20 | 9.86 | 2.28 | 10.15 | 1.37 |
| 24 | 11.75 | 5.79 | 12.51 | 1.00 |
| 28 | 13.51 | 13.07 | 14.80 | 1.83 |
| 32 | 15.38 | 18.06 | 17.47 | 3.78 |
| 36 | 16.39 | 29.37 | 18.07 | 13.36 |

Almost all of the glucose (DP-1) generated during the fermentation was converted to ethanol except at the high solids (data not shown). For each % DS tested, the AkAA increased the rate and amount of ethanol produced. In all instances the % starch in the DDGS is decreased when the AkAA is used in combination with the GA and further the % starch found in DDGS from a corn starch substrate having a % ds as high as 36% is reduced by half when compared to the % starch in a DDGS without the addition of AkAA. FIG. 10 shows as the % ds in the corn slurry increases, the influence of AkAA on ethanol production increases. These results demonstrate the positive effect AkAA has on hydrolyzing granular starch and particularly at high solids %.

Example 13

A 33% slurry of corn flour (Azure Standard Farms) was prepared in DI $H_2O$ to which 400 ppm urea was added. The pH was adjusted to 5.0. Fermentation were conducted in 125 ml flasks containing 100 g mash and the following treatments
A. *A. niger* GA blended with AkAA at 1.0 GAU/g and 3.0 SSU/g ds
B. HGA-GSHE at 1.0 GAU/g ds;
C. HGA-GSHE at 1.0 GAU/g and AkAA at 3.0 SSU/g ds;
D. HGA-GSHE at 2.0 GAU/g ds and
E. HGA-GSHE at 2.0 GAU/g and AkAA at 3.0 SSU/g ds.

The enzymes were diluted so that 0.5 ml was added to each flask. A 3% slurry of Fali dry yeast in water was prepared and mixed with a 32° C. water bath one hour prior to inoculating the fermenters by adding 1.0 ml of the yeast slurry. The flasks were placed in a 32° C. water bath and the mash mix gently. During the fermentations samples were removed for HPLC analysis. The fermentations were terminated after 72 hours and the beer dried at 62° C. to obtain the DDGS. The starch content of the DDGS was determined by the dual enzyme method.

TABLE 7

| Treatment | Sampled Hr | % w/v Lactic Acid | % v/v Ethanol | Total % v/v Ethanol | % Starch DDGS |
|---|---|---|---|---|---|
| A | 22 | 0.07 | 10.69 | 10.77 | |
| A | 46 | 0.08 | 18.02 | 18.07 | |
| A | 72 | 0.00 | 18.35 | 18.45 | 3.73 |
| B | 22 | 0.07 | 7.61 | 7.63 | |
| B | 46 | 0.10 | 11.27 | 11.30 | |
| B | 72 | 0.00 | 13.19 | 13.19 | 44.66 |
| C | 22 | 0.05 | 10.22 | 10.24 | |
| C | 46 | 0.06 | 17.48 | 17.53 | |
| C | 72 | 0.00 | 18.37 | 18.37 | 5.44 |

TABLE 7-continued

| Treatment | Sampled Hr | % w/v Lactic Acid | % v/v Ethanol | Total % v/v Ethanol | % Starch DDGS |
|---|---|---|---|---|---|
| D | 22 | 0.06 | 8.23 | 8.27 | |
| D | 46 | 0.08 | 12.39 | 12.42 | |
| D | 72 | 0.00 | 14.10 | 14.10 | 39.91 |
| E | 22 | 0.04 | 12.85 | 12.92 | |
| E | 46 | 0.06 | 18.02 | 18.13 | |
| E | 72 | 0.00 | 18.41 | 18.41 | 4.51 |

Example 14

A 33% slurry of corn flour (Azure Standard Farms) was prepared in DI $H_2O$ to which 400 ppm urea was added. The pH was adjusted to 4.5 with 5N $H_2SO_4$. Fermentation was conducted in 125 ml flasks containing 100 g mash. Enzymes as indicated below were diluted so that 0.5 ml was added to each flask. A 3% slurry of Fali dry yeast in water was prepared and mixed with a 32° C. water bath one hour prior to inoculating the fermenters by adding 1.0 ml of the yeast slurry. The flasks were placed in a 32° C. water bath and the mash mix gently. During the fermentations samples were removed for HPLC analysis. The fermentations were terminated after 72 hours and the beer dried at 62° C. to obtain the DDGS. The starch content of the DDGS was determined For table 8 below the enzyme treatments were 2.25 SSU AkAA and 0.75 GAU/g ds of *Aspergillus niger* GA as DISTILLASE (AkAA/AnGA); 2.25 SSU AkAA and 0.72 GAU/g of HGA (AkAA/HGA) and 2.25 SSU AkAA and 1.6 GAU/g of TrGA (AkAA/TrGA)

TABLE 8

| Sample Time (hrs) | % (v/v) Ethanol AkAA/AnGA | % (v/v) Ethanol AkAA/TrGA | % (v/v) Ethanol AkAA/HGA |
|---|---|---|---|
| 17 | 7.28 | 8.2 | 7.84 |
| 24 | 9.01 | 10.2 | 9.73 |
| 48 | 14.07 | 14.89 | 14.28 |
| 72 | 15.85 | 16.39 | 16.11 |

Example 15

A 33% slurry of corn flour (Azure Standard Farms) was prepared in DI $H_2O$ to which 400 ppm urea was added. The pH was adjusted to 4.5 with 5N $H_2SO_4$. Fermentation was conducted in 125 ml flasks containing 10 g mash. Enzymes as indicated below were diluted so that 0.5 ml was added to each flask. A 3% slurry of Fali dry yeast in water was prepared and mixed with a 32° C. water bath one hour prior to inoculating the fermenters by adding 1.0 ml of the yeast slurry. The flasks were placed in a 32° C. water bath and the mash mix gently. During the fermentations samples were removed for HPLC analysis at 22.5, 46 and 71 hours. The fermentations were terminated after 71 hours. *Aspergillus niger* glucoamylase was added to all flasks at 0.5 GAU/g. In addition, AkAA enzyme treatments including a) intact AkAA and b) the truncated AkAA enzymes of FIG. 5B, which were pooled together (see Example 5) were tested at different ratios of intact to truncated at a fixed AkAA dosage level of 1.5 SSU/g ds.

Increasing the ratio of intact to truncated AkAA gave increased ethanol production. At the end of the fermentation (71 hrs) the difference in ethanol production was less pronounced than at 22.5 or 46 hours. As observed in FIG. 11, at 71 hours higher ethanol production occurred with truncated AkAA as opposed to the control without AkAA. Further increasing the amount of intact AkAA from 0 to 50% of the total leads to increased ethanol production.

Example 16

Ethanol Production from Pullulanase in Combination with Glucoamylase and AkAA

A 36% corn flour slurry was prepared to which dry corn steep was added at 2.5% of the corn weight. The pH of the slurry was adjusted to 4.8. The slurry was used for fermentation without any further treatment by placing 100 gm of mash in 125 ml flasks. The desired amount of enzymes were added to each flask as shown in Table 1, and the flasks were then inoculated with 3 ml of yeast that was propagated in the mash for 17 hour. Each condition was run in duplicate.

The enzymes used were *A. niger* glucoamylase (GA) from a cell free culture filtrate concentrated to 683 GAU/gm of enzyme by evaporation in a rotary evaporator, AkAA at 5540 SSU/ml of enzyme, and pullulanase provided as Optimax L-1000

The flasks were placed in a 30° C. water bath and gently stirred with a magnetic stir bar. At various times, samples of the beer were removed for HPLC analysis.

The fermentations were terminated after 72 hours. A portion of the beer was dried at 60° C. to obtain the DDGS. The starch content of the DDGSs was then determined.

TABLE 9

| GA - GAU/g | AkAA SSU/g | Pullulanase ASPU/g | Ethanol % v/v 22 hrs | Ethanol % v/v 46 hrs | Ethanol % v/v 72 hrs | % starch DDGS at 72 hrs |
|---|---|---|---|---|---|---|
| 0.5 | 1.0 | 0.0 | 10.73 | 16.80 | 19.16 | 4.02 |
| 0.5 | 1.0 | 0.5 | 11.15 | 17.52 | 19.20 | 3.53 |
| 0.5 | 1.0 | 1.0 | 11.38 | 17.63 | 19.10 | 4.67 |
| 0.5 | 1.0 | 2.0 | 11.63 | 18.15 | 19.46 | 4.15 |

As observed from Table 9, pullulanase increased the fermentation rate and gave a slight increase in ethanol. However, pullulanase did not appear to influence the final ethanol yield. In addition % w/v was measured for DP>2, DP-2, DP-1, lactic acid and glycerol data not shown.

It is claimed:

1. An enzyme composition comprising: a) an isolated acid stable alpha amylase (asAA) having the sequence of SEQ ID NO: 3 and b) a glucoamylase.

2. The enzyme composition of claim 1, wherein the glucoamylase is obtained from a filamentous fungus.

3. The enzyme composition of claim 2, wherein the filamentous fungus is *Aspergilus, Trichoderma, Humicola* or *Rhizopus*.

4. The enzyme composition of claim 3, wherein the *Aspergillus* is *A. niger*.

5. The enzyme composition of claim 3, wherein the filamentous fungus is a *Trichoderma*.

6. The enzyme composition of claim 1, wherein the glucoamylase has granular starch hydrolyzing activity.

7. The enzyme composition of claim 1, wherein the ratio of asAA to glucoamylase activity (SSU:GAU) in the enzyme composition is 10:1 to 1:10.

8. The enzyme composition of claim 1 further comprising an enzyme selected from proteases, cellulases, pullulanases, alpha amylases and combinations thereof.

9. The enzyme composition of claim 1, wherein the asAA is obtained from heterologous expression in a host cell.

10. The enzyme composition of claim 9, wherein the host cell is a filamentous fungal host cell.

11. The enzyme composition of claim 10, wherein the filamentous fungal host cell is a *Trichoderma* cell.

12. The enzyme composition of claim 1 wherein the asAA has granular starch hydrolyzing (GSH) activity.

13. An enzyme composition comprising an acid stable alpha amylase (asAA) having the sequence of SEQ ID NO: 3.

14. A method of hydrolyzing granular starch comprising contacting a substrate containing granular starch with the enzyme composition of claim 1 at a temperature below the gelatinization temperature of the granular starch in the substrate and obtaining hydrolyzed starch, wherein at least 60% of the dry solids of the substrate are hydrolyzed.

15. The method according to claim 14, wherein the substrate is obtained from corn, wheat, sorghum, barley, rye or a combination thereof.

16. The method according to claim 15, wherein the substrate is corn.

17. The method according to claim 14, wherein the temperature is between 35 and 65° C.

* * * * *